(12) United States Patent
Nishioka

(10) Patent No.: US 7,369,327 B1
(45) Date of Patent: May 6, 2008

(54) VARIABLE OPTICAL-PROPERTY ELEMENT AND OPTICAL APPARATUS INCLUDING THE SAME

(75) Inventor: Kimihiko Nishioka, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 09/327,713

(22) Filed: Jun. 8, 1999

(30) Foreign Application Priority Data

| Jun. 9, 1998 | (JP) | ................................ 10-161198 |
| Jun. 30, 1998 | (JP) | ................................ 10-198073 |
| Jun. 30, 1998 | (JP) | ................................ 10-198080 |
| Jun. 30, 1998 | (JP) | ................................ 10-198155 |
| Jun. 30, 1998 | (JP) | ................................ 10-198164 |
| Oct. 8, 1998 | (JP) | ................................ 10-300296 |
| Oct. 8, 1998 | (JP) | ................................ 10-300299 |
| Nov. 25, 1998 | (JP) | ................................ 10-349311 |

(51) Int. Cl.
*G02B 17/00* (2006.01)
*G02B 15/14* (2006.01)
*G02B 3/02* (2006.01)

(52) U.S. Cl. ...................... 359/726; 359/676; 359/720; 359/727

(58) Field of Classification Search ................ 359/291, 359/846, 290, 630, 676, 678, 720, 726, 727, 359/728, 729; 349/193, 11, 13
See application file for complete search history.

(56) References Cited

U.S. PATENT DOCUMENTS

| 3,666,881 A | * | 5/1972 | Stein | ........................... 348/791 |
| 3,923,370 A | * | 12/1975 | Mostrom | ..................... 359/630 |
| 3,950,079 A | * | 4/1976 | Rambauske | .................. 359/226 |
| 4,196,973 A | * | 4/1980 | Hochstrate | .................... 349/68 |
| 4,872,743 A | * | 10/1989 | Baba et al. | .................. 359/298 |
| 4,919,520 A | | 4/1990 | Okada et al. | |
| 4,932,768 A | * | 6/1990 | Gobeli | ........................ 359/849 |
| 4,948,234 A | * | 8/1990 | Mihara | ........................ 359/688 |
| 5,004,319 A | * | 4/1991 | Smither | ....................... 359/570 |
| 5,014,121 A | * | 5/1991 | Hasegawa et al. | ............ 348/70 |
| 5,020,903 A | * | 6/1991 | Sakai et al. | .................... 356/28 |
| 5,046,824 A | * | 9/1991 | Pepper | ......................... 349/17 |
| 5,097,352 A | * | 3/1992 | Takahashi et al. | ........... 349/57 |
| 5,177,605 A | * | 1/1993 | Takahashi et al. | ........... 348/65 |
| 5,198,653 A | * | 3/1993 | Shen et al. | .............. 250/201.9 |
| 5,214,685 A | * | 5/1993 | Howells | ....................... 378/34 |
| 5,223,971 A | * | 6/1993 | Magel | ......................... 359/295 |
| 5,406,412 A | * | 4/1995 | Zehnpfennig et al. | ...... 359/399 |

(Continued)

FOREIGN PATENT DOCUMENTS

EP     785 457 A2     7/1997

(Continued)

*Primary Examiner*—David N. Spector
(74) *Attorney, Agent, or Firm*—Pillsbury Winthrop Shaw Pittman LLP

(57) ABSTRACT

A variable optical-property element includes a liquid crystal the pitch of twist is less than 60 times the wavelength of light used, so that a spatially uneven electric or magnetic field or temperature is applied to the liquid crystal to thereby form an index distribution, and the electric or magnetic field or the temperature is changed to thereby alter the index distribution. In this way, the variable optical-property element is capable of changing its optical properties as a liquid crystal lens and is used in an optical apparatus.

17 Claims, 37 Drawing Sheets

U.S. PATENT DOCUMENTS

| | | | | |
|---|---|---|---|---|
| 5,428,444 | A * | 6/1995 | Haddock et al. | 356/458 |
| 5,513,041 | A * | 4/1996 | Togino | 359/631 |
| 5,557,477 | A * | 9/1996 | Sawicki | 359/846 |
| 5,594,549 | A * | 1/1997 | Mori et al. | 356/401 |
| 5,641,958 | A * | 6/1997 | Rudeen | 250/235 |
| 5,770,847 | A * | 6/1998 | Olmstead | 235/462.35 |
| 5,793,473 | A * | 8/1998 | Koyama et al. | 355/55 |
| 5,805,367 | A * | 9/1998 | Kanazawa | 359/868 |
| 6,025,866 | A * | 2/2000 | Tsuchiya et al. | 347/256 |
| 6,073,851 | A * | 6/2000 | Olmstead et al. | 235/462.45 |
| 6,147,789 | A * | 11/2000 | Gelbart | 359/231 |
| 6,166,866 | A * | 12/2000 | Kimura et al. | 359/729 |
| 6,191,829 | B1 * | 2/2001 | Hashimoto | 349/17 |
| 6,211,944 | B1 * | 4/2001 | Shiraishi | 355/53 |
| 6,437,925 | B1 * | 8/2002 | Nishioka | 359/726 |
| 6,464,363 | B1 * | 10/2002 | Nishioka et al. | 359/846 |
| 6,522,475 | B2 * | 2/2003 | Akiyama et al. | 359/676 |
| 6,618,209 | B2 * | 9/2003 | Nishioka et al. | 359/676 |
| 6,658,208 | B2 * | 12/2003 | Watanabe et al. | 396/89 |
| 6,738,199 | B2 * | 5/2004 | Nishioka | 359/726 |
| 6,833,966 | B2 * | 12/2004 | Nishioka et al. | 359/726 |
| 6,865,009 | B2 * | 3/2005 | Nishioka | 359/295 |
| 6,888,590 | B1 * | 5/2005 | Nishioka et al. | 349/57 |
| 6,950,245 | B2 * | 9/2005 | Nishioka et al. | 359/721 |
| 7,025,468 | B2 * | 4/2006 | Nishioka et al. | 359/846 |
| 7,031,071 | B2 * | 4/2006 | Nishioka | 359/676 |
| 7,054,053 | B2 * | 5/2006 | Nishioka | 359/291 |
| 7,054,075 | B2 * | 5/2006 | Nishioka et al. | 359/726 |
| 7,170,665 | B2 * | 1/2007 | Kaneko et al. | 359/290 |
| 7,190,500 | B2 * | 3/2007 | Ide et al. | 359/224 |
| 7,209,295 | B2 * | 4/2007 | Nishioka et al. | 359/676 |

FOREIGN PATENT DOCUMENTS

| | | |
|---|---|---|
| JP | 04-345124 A | 12/1992 |
| JP | 05-034656 A | 2/1993 |
| JP | 09-243806 | 9/1997 |

* cited by examiner

LIGHT →

P

VARIABLE OPTICAL-PROPERTY ELEMENT AND OPTICAL APPARATUS INCLUDING THE SAME

This application relies for priority upon Japanese Patent Application Nos. 10-161198 filed Jun. 9, 1998, 10-198073 filed on Jun. 30, 1998, 10-198080 filed on Jun. 30, 1998, 10-198155 filed on Jun. 30, 1998, 10-198164 filed on Jun. 30, 1998, 10-300296 filed on Oct. 8, 1998, 10-300299 filed on Oct. 8, 1998, and 10-349311 filed Nov. 25, 1998, the contents of all of which are incorporated by reference herein.

BACKGROUND OF THE INVENTION

1. Field of the Invention

This invention relates to a variable optical-property element capable of changing optical properties, such as a variable focal-length lens, variable focal-length diffraction optical element, variable deflection-angle prism, or variable focal-length mirror, and in particular, to an optical apparatus including the variable optical-property element.

2. Description of Related Art

The focusing operation of a zoom lens system or an imaging device is usually performed by mechanically moving lenses. However, for an electronic endoscope which is required to be subminiature or the eye of a micromachine, it is impossible to move the whole or a part of a lens system. Moreover, it is desirable that a TV camera, an electronic still camera, or a silver halide film camera is capable of performing zooming and focusing operations without moving the lens system in order to achieve its compactness and reduction in cost.

As means for performing the zooming and focusing operations without moving the lens system, variable focal-length lenses have been proposed, for example, in Japanese Patent Preliminary Publication Nos. Hei 5-34656 and Hei 4-345124.

FIG. 1 shows a liquid crystal lens which is an example of this type of variable focal-length lens. In this figure, reference numeral 1 represents a nematic liquid crystal with molecules obliquely oriented which is hermetically sealed by a seal member 2 and sandwiched between a pair of transparent substrates 4 and 5, each having a doughnut-shaped electrode 3. Reference numeral 6 denotes orientation films provided on surfaces inside the transparent substrates 4 and 5; 7 denotes a polarizing plate placed on the front (left) side of the substrate 4, transmitting only light vibrating in the plane of the paper; and 8 denotes an AC power supply connected to the electrodes 3 through a switch 9 and a variable resistor 10.

In this liquid crystal lens, when the switch 9 is turned off, the molecules of the liquid crystal 1, as shown in the figure, are obliquely oriented so that light rays L travel in straight lines. In contrast to this, when the switch 9 is turned on to apply voltages to the electrodes 3, the direction of an electric field becomes uneven because the electrodes 3 are doughnut-shaped, and the molecules of the liquid crystal 1 are oriented as shown in FIG. 2. Specifically, the molecules of the liquid crystal 1 maintain an oblique orientation in the vicinity of the center of the liquid crystal lens in which the strength of the electric field is diminished. However, since the strength of the electric field is increased progressively in approaching the electrodes 3, the molecules of the liquid crystal 1 are oriented perpendicular to the substrates 4 and 5. Hence, for polarized light transmitted through the polarizing plate 7, the refractive index of the liquid crystal 1 becomes high in going from the periphery to the center of the liquid crystal lens so as to have an index distribution in a radial (y) direction of the liquid crystal lens. In this way, the liquid crystal lens becomes an inhomogeneous lens having the function of a positive lens, and thus the light rays L of incidence converge.

However, this conventional liquid crystal lens, which needs the polarizing plate 7, has the drawback that the amount of transmitted light is so small that a transmittance is as low as 30-40%, and applicable products are highly limited.

Furthermore, a conventional variable focal-length lens has a mechanically complicated structure that because a lens made by grinding glass is used and the focal length cannot be changed by the lens itself, a part of a lens unit must be moved along the optical axis as in the zoom lens of a camera to change the focal length.

In order to obviate such a defect, it is necessary to change the focal length of the lens itself, and as shown in FIG. 3, an optical system using a polarizing plate 11 and a liquid crystal lens 12 is proposed. The liquid crystal lens 12 used in this optical system has lenses 13a and 13b and a liquid crystal layer 15 sandwiched through transparent electrodes 14a and 14b between the lenses 13a and 13b. The liquid crystal lens 12 is designed so that an AC power supply 17 is connected through a switch 16 between the transparent electrodes 14a and 14b to selectively apply the electric field to the liquid crystal layer 15, and thereby the refractive index of the liquid crystal layer 15 is changed.

In the optical system including the polarizing plate 11 and the liquid crystal lens 12 as shown in FIG. 3, for example, when natural light is rendered incident on the optical system, only a predetermined linearly polarized light component is transmitted through the polarizing plate 11 and enters the liquid crystal lens 12.

Here, as show in FIG. 3, when the switch 16 is turned off and the electric field is not applied to the liquid crystal layer 15 of the liquid crystal lens 12, the major axes of liquid crystal molecules 15a point in the same direction as in the linearly polarized light component, and thus the refractive index of the liquid crystal layer 15 is increased. Consequently, the focal length of the liquid crystal lens 12 is diminished.

In contrast to this, as shown in FIG. 4, when the switch 16 is turned on and the electric field is applied to the liquid crystal layer 15, the liquid crystal molecules 15a is such that since their major axes become parallel to the optical axis, the refractive index of the liquid crystal layer 15 is lowered and the focal length of the liquid crystal 12 is increased.

In this way, the optical system shown in FIGS. 3 and 4 is constructed so that the electric field is selectively applied to the liquid crystal lens 12 and thereby the focal length is changed.

However, this optical system requires that the polarizing plate 11 is placed on the front side of the liquid crystal lens 12 to render only the predetermined linearly polarized light component incident on the liquid crystal lens 12. Hence, the optical system has the disadvantage that the amount of light transmitted through the polarizing plate 11 to enter the liquid crystal lens 12 is reduced and the efficiency of use of light is impaired. Consequently, there is an additional disadvantage that products to which the optical system is applicable are limited and its versatility is lost. Furthermore, there is another disadvantage that much time is required to change the focal length.

On the other hand, the variable optical-property element, such as a liquid crystal lens, has the advantage that optical properties such as a focal length, can be changed by a single optical element. However, the use of only the variable optical-property element, which causes spherical aberration, distortion, and chromatic aberration, is unfavorable.

In addition, the variable optical-property element has the drawback that when its optical properties, for example, the focal length is changed, aberration fluctuates or flare-increases.

In the optical system of the variable optical-property element, a free-formed surface optical element may be used. The free-formed surface of the free-formed surface optical element refers to a curved surface composed of an irrotational symmetric surface, which may or may not include one symmetric surface. A surface in which a rotational symmetric surface is decentered also comes under the class of the free-formed surface. An optical system using the optical element with the free-formed surface (irrotational symmetric surface) utilizes the reflection of the free-formed surface, and thus has the merit that chromatic aberration is not produced. This optical system, however, has the disadvantage that the shape of the curved surface is abnormal, and thus when the optical element is moved for the zooming and focusing operations, a mechanical structure such as a moving mechanism becomes complicated.

SUMMARY OF THE INVENTION

It is, therefore, an object of the present invention to provide a variable optical-property element in which its structure is simple, there is essentially no loss in the amount of light, operation can be performed at a low voltage, and optical properties can be changed.

It is another object of the present invention to provide a variable optical-property element, such as a variable focal-length lens, variable focal-length diffraction optical element, or variable deflection-angle prism, which is constructed to raise the efficiency of use of light and to reduce time required to change optical properties such as a focal length, is effectively applicable to various optical products, and has exceptional versatility.

It is another object of the present invention to provide an imaging device having a small-sized optical system in which optical properties can be changed and aberrations are favorably corrected by adding a curved surface to a variable optical-property element.

It is another object of the present invention to provide an imaging device which has a variable optical-property element and is designed to correct the fluctuations of aberration and flare caused when optical properties are changed.

It is another object of the present invention to provide an optical system which includes an optical element having free-formed surfaces and a variable optical-property reflecting mirror.

It is another object of the present invention to provide an imaging device which has the optical system and an image sensor.

It is another object of the present invention to provide an imaging device or an optical finder which has the optical system and a display.

The variable optical-property element of the present invention includes a liquid crystal in which the pitch of twist is less than 60 times the wavelength of light used, so that a spatially uneven electric or magnetic field or temperature is applied to the liquid crystal to thereby form an index distribution, and so that the electric or magnetic field or the temperature is changed to thereby alter the index distribution.

The variable optical-property element of the present invention includes a macromolecular dispersed liquid crystal, so that a spatially uneven electric or magnetic field or temperature is applied to the liquid crystal to thereby form an index distribution, and so that the electric or magnetic field or the temperature is changed to thereby alter the index distribution.

The variable optical-property element of the present invention includes a combination of at least two liquid crystal lenses with positive and negative powers.

The variable optical-property element of the present invention uses a liquid crystal in which the anisotropy of refractive index is negative, so that its optical properties are changed by altering an electric or magnetic field or temperature applied to the liquid crystal.

The variable optical-property element of the present invention uses a liquid crystal in which the anisotropy of refractive index is negative, so that an electric field is applied to the liquid crystal and thereby the refractive index is changed. In this way, the focal length of the variable optical-property element is changed.

The variable optical-property element of the present invention uses a liquid crystal in which, for example, the anisotropy of refractive index is not negative but positive, so that an electric field is applied to the liquid crystal and thereby the refractive index is changed.

The variable optical-property element of the present invention is such that a magnetic field is applied to a liquid crystal and thereby its refractive index is changed.

The variable optical-property element of the present invention uses a substance possessing an electrooptical effect such that the orientation of liquid crystal molecules in a plane nearly perpendicular to the optical axis of incidence is almost uniform.

The variable optical-property element of the present invention can be used in an imaging device and others.

The imaging device of the present invention is provided with an optical system comprising a stop, a front lens unit including a variable optical-property element possessing the function of a negative lens, placed close to the stop, and a rear lens unit including at least one concave surface and one convex surface, placed behind (on the image side of) the front lens unit.

The imaging device of the present invention has a variable optical-property element and is constructed to correct the fluctuation of aberration caused when the optical properties of the variable optical-property element are changed, either by altering the MTF characteristics of an electronic circuit or by changing an image processing technique.

The imaging device of the present invention is provided with an optical element having irrotational symmetric surfaces, a variable optical-property reflecting mirror, and an image sensor so that the reflecting mirror and the image sensor are placed on the same substrate, and all or a part of the reflecting mirror and the optical element having the irrotational symmetric surfaces constitutes an optical system.

The imaging device of the present invention is provided with an optical element having irrotational symmetric surfaces and a variable optical-property reflecting mirror, which is placed close to one of the surfaces of the optical element.

These and other objects as well as the features and advantages of the present invention will become apparent from the following detailed description of the preferred embodiments when taken in conjunction with the accompanying drawings.

DETAILED DESCRIPTION OF THE PREFERRED EMBODIMENTS

Before undertaking the description of the embodiments, it will be expedient to explain the definitions of terms employed in the present invention. An optical apparatus used in the present invention refers to an apparatus including an optical system or optical elements, or a part of this apparatus. The optical apparatus need not necessarily function by itself. That is, it is may be thought of as a part of an apparatus or a unit.

The optical apparatus includes an imaging device, an observation device, a display device, an illumination device, and a signal processing device. The imaging device refers to, for example, a film camera, a digital camera, a TV camera, a VTR camera, or an electronic endoscope. The observation device refers to, for example, a microscope, a telescope, spectacles, binoculars, a magnifier, a fiber scope, or a finder. The display device includes, for example, a liquid crystal display, a viewfinder, a head mounted display, or a PDA (personal digital assistant). The illumination device includes, for example, a stroboscopic lamp for cameras, a headlight for cars, a light source for endoscopes, or a light source for microscopes. Finally, the signal processing device refers to, for example, a read/writ device for optical disks, a bar-code reader, a bar-code scanner, or a computer for optical calculators.

The variable optical-property element can be used in the optical apparatus, and its compact and lightweight design, and function improvement are achieved.

Figure 1:
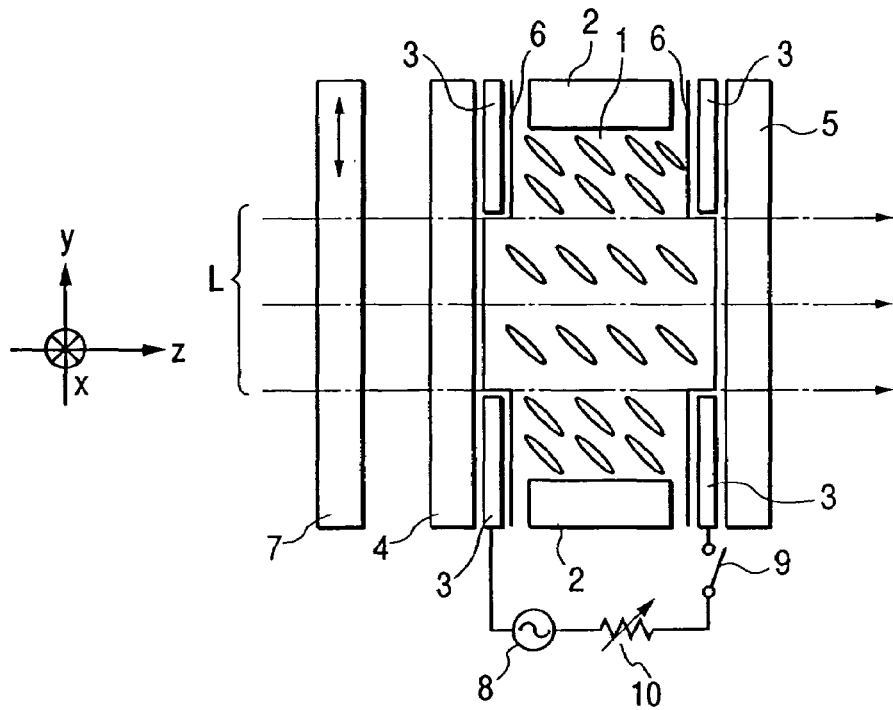
FIG. 1 is a view showing the fundamental structure of a conventional liquid crystal lens.
Figure 2:
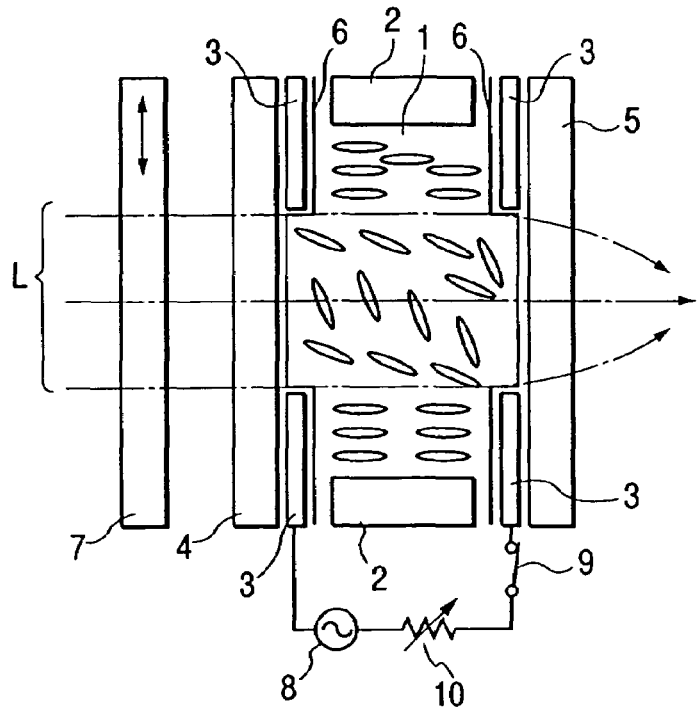
FIG. 2 is a view showing the orientation of the molecules of a liquid crystal where an electric field is applied to the liquid crystal lens of FIG. 1.
Figure 3:
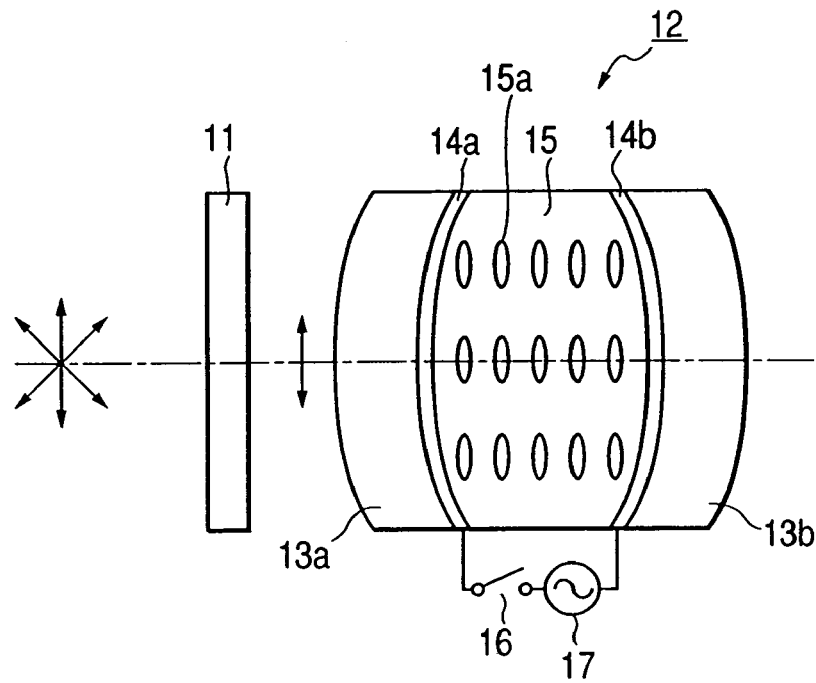
FIG. 3 is a view showing the fundamental structure of another conventional liquid crystal lens.
Figure 4:
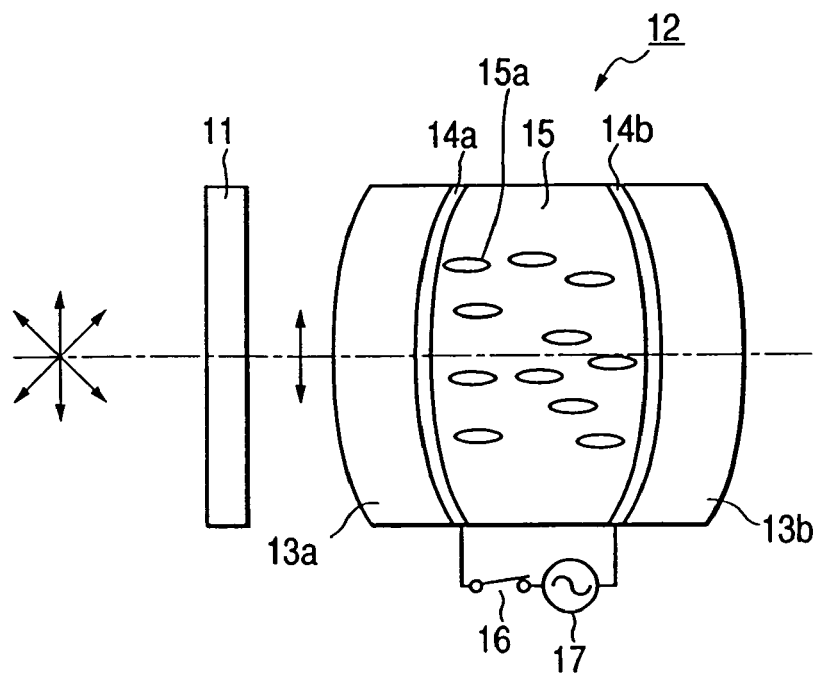
FIG. 4 is a view showing the orientation of the molecules of a liquid crystal where an electric field is applied to the liquid crystal lens of FIG. 3.
Figure 5:
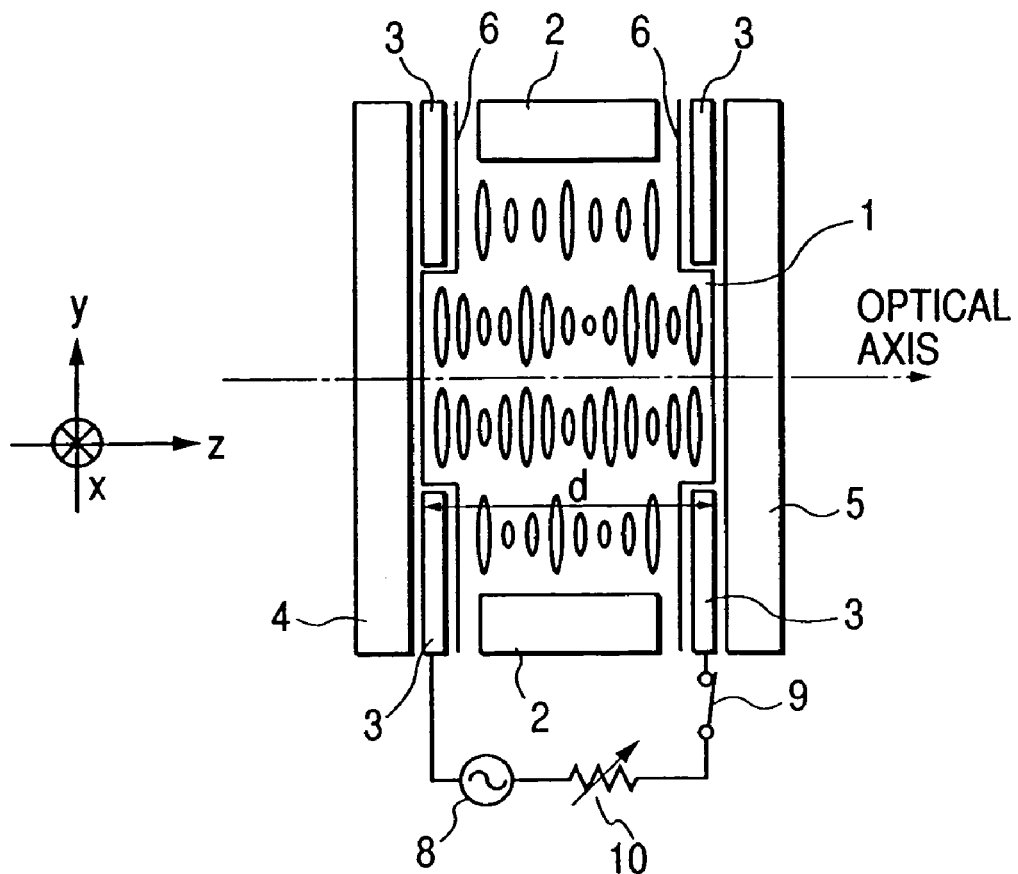
FIG. 5 is a view showing the fundamental structure of one example of the variable optical-property element according to the present invention.

In accordance with the embodiments shown in the drawings, the aspects of the present invention will be described below. FIG. 5 shows a variable focal-length lens as one embodiment of the variable optical-property element of the present invention. In this figure, like numerals are used for like members with respect to the description of the prior art. The variable focal-length lens has a basic structure that the nematic liquid crystal 1 is sandwiched through the orientation films 6 between the substrates 4 and 5 depositing the doughnut-shaped electrodes 3 inside them and is hermetically sealed with the seal member 2. Here, it is assumed that a pitch P of twist (FIG. 6) of the nematic liquid crystal 1 is much smaller than a wavelength λ of light used. That is, $$P \ll \lambda \tag{1}$$

Figure 7:
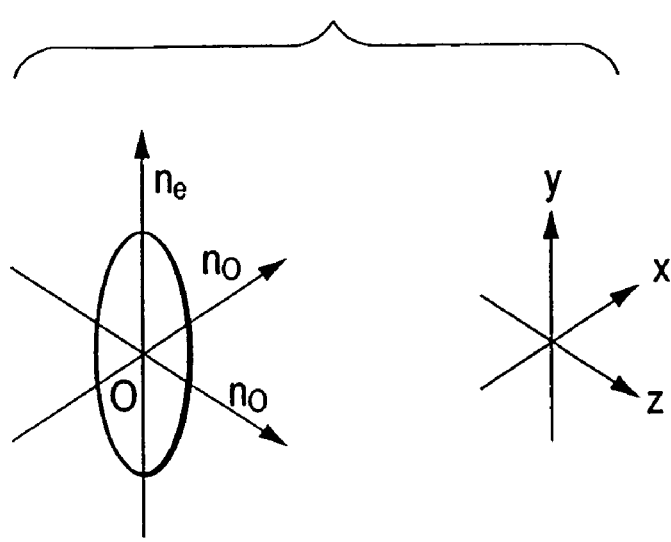
FIG. 7 is a view showing an index ellipsoid relative to a molecule on the entrance side of the nematic liquid crystal.

When the pitch P is much smaller than the wavelength λ of light as mentioned above, the variable focal-length lens does not rely on the polarization of incident light and functions as a medium with a refractive index n':

$$n' = (n_e + n_0)/2 \tag{2}$$

where $n_e$ is a refractive index relative to polarized light in the direction of the major axis of a liquid crystal molecule and $n_0$ is a a refractive index relative to polarized light in the direction of the minor axis of the liquid crystal molecule. FIG. 7 shows an index ellipsoid relative to the liquid crystal molecule on the entrance side of the nematic liquid crystal 1. Here, x and z axes stand for the directions of the minor axes of the liquid crystal molecule and a y axis stands for the direction of the major axis of the liquid crystal molecule. Also, it is assumed that $n_e > n_0$.

Subsequently, in accordance with the Jones' vector and matrix, a description will be given of the reason why the nematic liquid crystal 1 behaves effectively as an isotropic medium with the refractive index n'.

According to Eqs. 3.10, 3.110, and 3.126 discussed by K. Yoshino and M. Okazaki, "Fundamentals of Liquid Crystals and Display Applications", Corona, pp. 85-92, a Jones' matrix $W_t$ relative to the nematic liquid crystal 1 with a thickness d, shown in FIG. 5, including an absolute phase change exp (–ia), is given by $$W_t = e^{-ia} R(-\Phi) \begin{pmatrix} \cos X - i\frac{\Gamma}{2}\frac{\sin X}{X} & \Phi\frac{\sin X}{X} \\ -\Phi\frac{\sin X}{X} & \cos X + i\frac{\Gamma}{2}\frac{\sin X}{X} \end{pmatrix} \tag{3}$$

where $$\Phi = 2\pi d/P \tag{4}$$

$$\Gamma = 2\pi(n_e - n_0)d/\lambda \tag{5}$$

$$\alpha = 2\pi\{(n_e + n_0)/2\}d/\lambda \tag{6}$$

$$X = (\Phi^2 + \Gamma^2/2)^{1/2} \tag{7}$$

$$R(-\Phi) = \begin{pmatrix} \cos\Phi & -\sin\Phi \\ \sin\Phi & \cos\Phi \end{pmatrix} \tag{8}$$

Here, when ordinary light is defined as polarized light in the direction of the minor axis of the liquid crystal molecule and extraordinary light is defined as polarized light in the direction of the major axis of the liquid crystal molecule or in the direction in which the major axis is projected on a plane parallel to the optical axis, $\Gamma$ stands for a phase difference between the ordinary light and the extraordinary light, due to the nematic liquid crystal 1.

Also, $\Phi$ is the angle of twist of the liquid crystal molecules of the nematic liquid crystal 1 in radian. It is assumed that the coordinates of Equations (3) and (8) are as x, y, and z axes shown in FIG. 5. Specifically, the x axis extends from the front side toward the back side of the plane of the figure and the y axis is the direction of the major axis of the liquid crystal molecule at the entrance surface of the nematic liquid crystal 1.

Subsequently, consider how the Jones' matrix $W_t$ of Equation (3) changes under Condition (1). Condition (1) can be rewritten as $$0 < P/\lambda \ll 1 \tag{9}$$

Here, when $P/\lambda$ approaches zero, find an ultimate value $W_{tL}$ of the Jones' matrix $W_t$ of Equation (3).

$$\Gamma/\Phi = (ne-n_0)P/\lambda \tag{10}$$

and thus, when $P/\lambda \ll 1$, $$|\Gamma/\Phi| \ll 1 \tag{11}$$

and when $P/\lambda$ approaches zero, $|\Gamma/\Phi|$ also approaches zero.

Under Condition (11), the following approximations are accomplished:

$$X = \Phi\sqrt{\left(1 + \frac{\Gamma^2}{2\Phi^2}\right)} \doteq \Phi + \frac{\Gamma^2}{4\Phi} \tag{12}$$

$$\cos X \doteq \cos\left(\Phi + \frac{\Gamma^2}{4\Phi}\right) \tag{13}$$

$$\frac{\Gamma}{2}\frac{\sin X}{X} \doteq \frac{\Gamma}{2}\frac{\sin\left(\Phi + \frac{\Gamma^2}{4\Phi}\right)}{\Phi + \frac{\Gamma^2}{4\Phi}} \tag{14}$$

$$\Phi\frac{\sin X}{X} \doteq \frac{\sin\left(\Phi + \frac{\Gamma^2}{4\Phi^2}\right)}{1 + \frac{\Gamma^2}{4\Phi^2}} \tag{15}$$

When $P/\lambda$ approaches zero, the following equations are obtained:

$$X \to \Phi \tag{16}$$

$$\cos X \to \cos \Phi \tag{17}$$

$$\frac{\Gamma}{2}\frac{\sin X}{X} \to 0 \tag{18}$$

$$\Phi\frac{\sin X}{X} \to \sin\Phi \tag{19}$$

and thus, when $P/\lambda$ approaches zero, the following equation is obtained:

$$W_{tL} \to e^{-i\alpha}R(-\Phi)\begin{pmatrix} \cos\Phi & \sin\Phi \\ -\sin\Phi & \cos\Phi \end{pmatrix} = e^{-i\alpha}\begin{pmatrix} 1 & 0 \\ 0 & 1 \end{pmatrix} \tag{20}$$

This is indeed the Jones' matrix of a medium which has the refractive index $n' = (ne+n_0)/2$ and the thickness d and is isotropic along the optical axis. Thus, since $P/\lambda \ll 1$, the variable focal-length lens shown in FIG. 5 functions as the medium with the refractive index n'.

Figure 6:
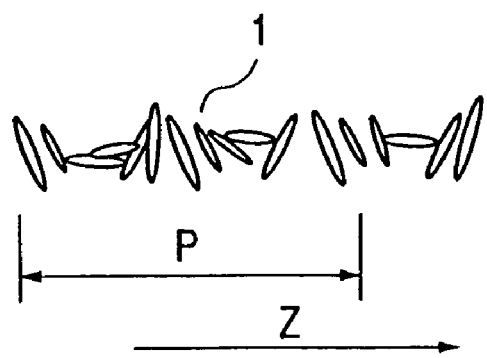
FIG. 6 is a view for explaining a state of the twist of a nematic liquid crystal shown in FIG. 5.
Figure 8:
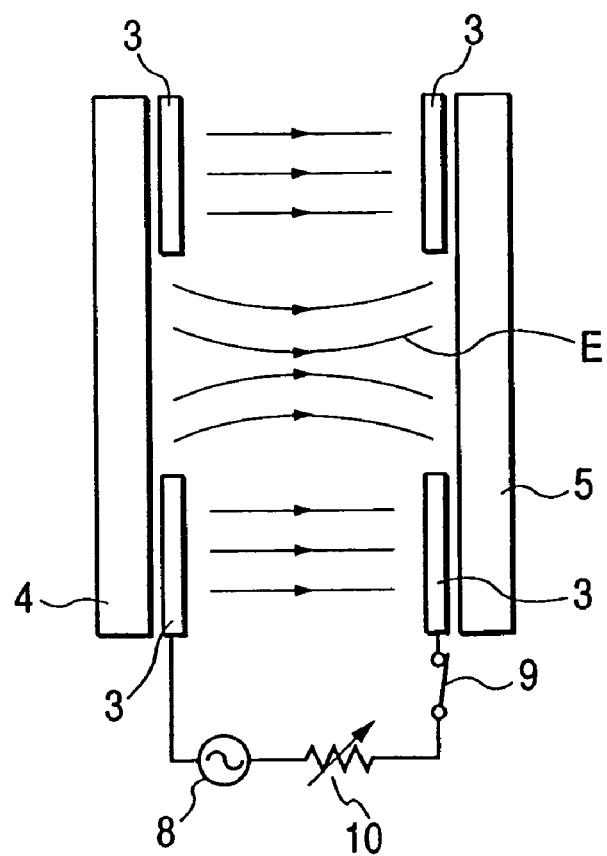
FIG. 8 is a view showing a state of an electric field applied to the variable optical-property element of FIG. 5.
Figure 9:
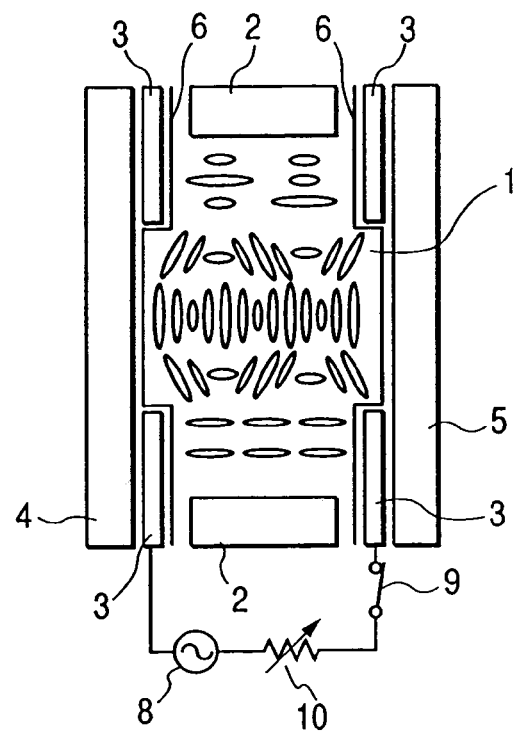
FIG. 9 is a view showing a state of the orientation of the molecules of a liquid crystal where an electric field is applied to the variable optical-property element of FIG. 5.

When the switch 9 is turned on in a state of FIG. 5, an electric field E such as that shown in FIG. 8 is applied to the liquid crystal 1, and hence the molecular orientation of the liquid crystal 1 is shifted as shown in FIG. 9. Specifically, a nearly helical orientation remains in the vicinity of the optical axis of the liquid crystal lens, and the liquid crystal molecules tend to be oriented perpendicular to the substrates 4 and 5 progressively in separating from the optical axis, so that molecules sandwiched between the electrodes 3 are oriented nearly perpendicular to the substrates 4 and 5. FIG. 6 shows the molecular orientation of the liquid crystal 1 at some distance from the optical axis. Since the liquid crystal molecules are oriented in this way, the liquid crystal has the refractive index n' in the vicinity of the optical axis and the refractive index $n_0$ in the periphery to function as an inhomogeneous lens. Equations and Conditions (3)-(20) are applicable to a minute portion of the liquid crystal 1. In this way, a bright, variable focal-length lens with no polarizing plate is obtained.

Next, reference is made to a specific example of the variable focal-length lens mentioned above. The variable focal-length lens, as shown in FIG. 5, is designed so that the voltage can be continuously changed by the variable resistor 10 and the liquid crystal molecules can be arranged in a state of a compromise between FIGS. 5 and 9. Consequently, a liquid crystal lens in which the focal length is continuously changed can be realized.

Figure 10:
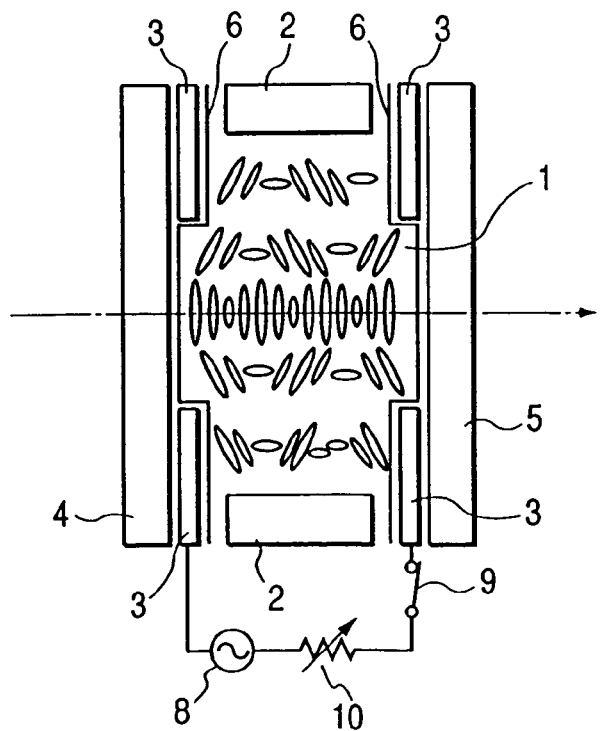
FIG. 10 is a view showing another state of the orientation of the molecules of a liquid crystal where an electric field is applied to the variable optical-property element of FIG. 5.

Even in the case of a compromise arrangement of the liquid crystal molecules shown in FIG. 10, the value of the refractive index ne is replaced by a certain value between the refractive indices ne and $n_0$, namely a refractive index ne' of extraordinary light, and thereby Equations and Conditions (3)-(20) are satisfied.

Also, by constructing the variable focal-length lens as shown in FIG. 5, not only is the voltage applied to be continuously changeable, but also an applied voltage can be chosen from among some discrete voltage values.

Here, an actual example of the variable focal-length lens constructed as in FIG. 5 will be described in detail. Although the limit where $P/\lambda$ approaches zero is given by Equation (20), the value of this limit may not necessarily hold for an actual liquid crystal lens or variable focal-length lens. Thus, consider the approximation of Equation (3) to be introduced. The following equations are established even in the case where $P/\lambda \geq 1$.

When Equation (3) is approximated, taking account of the first order of $P/\lambda$, the following results are obtained. Specifically, when the first order of $P/\lambda$ remains in Equations (12)-(14), that is, the first order of $\Gamma/\Phi$ remains in Equation (10) to neglect higher orders of $P/\lambda$ and $\Gamma/\Phi$, the following approximations are obtained:

$$\cos X - i\frac{\Gamma}{2}\frac{\sin X}{X} \doteq \cos\left(\Phi + \frac{\Gamma}{4}\frac{\Gamma}{\Phi}\right) - i\frac{\Gamma}{2\Phi}\sin\left(\Phi + \frac{\Gamma}{4}\frac{\Gamma}{\Phi}\right) \quad (21)$$

$$\Phi\frac{\sin X}{X} \doteq \sin\left(\Phi + \frac{\Gamma}{4}\frac{\Gamma}{\Phi}\right) \quad (22)$$

$$W_t \doteq \quad (23)$$

$$e^{-i\alpha}R(-\Phi)\begin{pmatrix} \cos\left(\Phi + \frac{\Gamma}{4}\frac{\Gamma}{\Phi}\right) - i\frac{\Gamma}{2\Phi}\sin\left(\Phi + \frac{\Gamma}{4}\frac{\Gamma}{\Phi}\right) & \sin\left(\Phi + \frac{\Gamma}{4}\frac{\Gamma}{\Phi}\right) \\ -\sin\left(\Phi + \frac{\Gamma}{4}\frac{\Gamma}{\Phi}\right) & \cos\left(\Phi + \frac{\Gamma}{4}\frac{\Gamma}{\Phi}\right) + i\frac{\Gamma}{2\Phi}\sin\left(\Phi + \frac{\Gamma}{4}\frac{\Gamma}{\Phi}\right) \end{pmatrix}$$

$$\equiv W_{tN} \quad (23)$$

Hence, In order that the value of $W_{tN}$ can be thought of as nearly equal to the Jones' matrix of the Isotropic medium, it is only necessary to make the value of $|i\Gamma/2\Phi|$ close to zero. In this case, $W_{tN}$ approaches the following matrix:

$$e^{-i\alpha}\begin{pmatrix} \cos\left(\frac{\Gamma}{4}\frac{\Gamma}{\Phi}\right) & \sin\left(\frac{\Gamma}{4}\frac{\Gamma}{\Phi}\right) \\ -\sin\left(\frac{\Gamma}{4}\frac{\Gamma}{\Phi}\right) & \cos\left(\frac{\Gamma}{4}\frac{\Gamma}{\Phi}\right) \end{pmatrix}$$

This equation means that the liquid crystal 1 rotates incident light by $\Gamma/4\cdot\Gamma/\Phi$ for polarization, but can be thought of as the isotropic medium.

$$\left|i\frac{\Gamma}{2\Phi}\right| \doteq 0 \quad (25)$$

that is, if $$\left|\frac{\Gamma}{2\Phi}\right| \ll 1 \quad (26)$$

a variable focal-length lens which does not cause the blurring of an image will be obtained. From Equation (10), the following equation is derived:

$$\frac{\Gamma}{2\Phi} = \frac{1}{2}(n_e - n_0)\frac{P}{\lambda} \quad (27)$$

When the variable focal-length lens of the present invention is used for each of lenses employed in relatively low-cost products of actual photographing apparatuses with lenses, such as electronic cameras, VTR cameras, and electronic endoscopes, a high resolution may not necessarily be required. Hence, Condition (26) can be moderated as follows:

$$|\Gamma/2\Phi|<1 \quad (28)$$

Since the high resolution is required for lenses of an electronic photographing apparatus with a large number of pixels and a product with high image quality, such as a film camera or a microscope, it is only necessary to satisfy the following condition:

$$|\Gamma/2\Phi|<\pi/6 \quad (29)$$

In the case of a lens which is not used for image formation as in an optical disc, or an electronic photographing apparatus with a small number of pixels, the condition is further moderated as follows:

$$|\Gamma/2\Phi|<\pi \quad (30)$$

As is true of any embodiment, when the liquid crystal 1 has a helical arrangement or when the major axes of the liquid crystal molecules are not perpendicular to the optical axis, namely oblique, it is only necessary to replace the refractive index ne corresponding to Equations and Conditions (1) and (26)-(30) with the refractive index ne'.

Some design examples are cited below. If the thickness d of the liquid crystal 1 is too small, the power of the lens will be reduced and the liquid crystal will be of no use as the lens. If it is too large, light will be scattered and flare will be caused. Therefore, the following condition is moderate:

$$2\mu<d<300\mu \quad (31)$$

When visible light is considered as an example of the wavelength $\lambda$ of light, it is only necessary to satisfy the following condition:

$$0.35\mu<\lambda<0.7\mu \quad (32)$$

Although the value of $(n_e-n_0)$ is governed by the physical properties of the liquid crystal, most substances satisfy the following condition:

$$0.01<|n_e-n_0|<0.4 \quad (33)$$

Thus, as the first design example, when respective parameters are set as follows:
 d=15μ
 λ=0.5μ
 $n_e-n_0$=0.2
 P=0.05μ
 φ=60μ (the effective diameter of the variable focal-length lens)
then $$\Gamma/2\Phi=1/2\cdot 0.2\times 0.05/0.5=0.01$$

This satisfies Conditions (26) and (28)-(30).

As the second design example, when the respective parameters are set as follows:
 d=30μ
 λ=0.6μ
 $n_e-n_0$=0.25
 P=0.3μ
 φ=180μ
then $$\Gamma/2\Phi=1/2\cdot 0.3\times 0.25/0.6=0.0625$$

This satisfies Conditions (26) and (28)-(30).

As the third design example, when the respective parameters are set as follows:
 d=50μ
 λ=0.55μ
 $n_e-n_0$=0.2
 P=5=
 φ=150μ
then $$\Gamma/2\Phi=1/2\cdot 0.2\times 5.0/0.55=0.909$$

This satisfies Conditions (28) and (30).

Further, when a variable focal-length lens for near infrared light is considered as the fourth design example and the respective parameters are set as follows:

d=200μ
λ=0.95μ
ne−n₀=0.2
P=4=μ
φ=2000μ then

Γ/2Φ=1/2·0.2×4/0.95=0.42

This satisfies Conditions (26) and (28)-(30).

In each of the design examples mentioned above, the nematic liquid crystal is used as an example. In order to make the pitch of twist of the nematic liquid crystal smaller than the wavelength of light used, it is good practice to mix a chiral dopant with the liquid crystal.

As the chiral dopants, cholesteric liquid crystals or optically active, synthetic compounds are used. The examples of the nematic liquid crystals are shown in chemical formulas (a) and (b) described below and the examples of the chiral dopants are shown in chemical formulas (c) and (d).

(a)
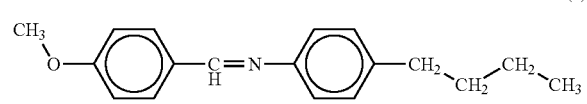
N-(4-methoxybenzylidene)-4'-n-butylaniline
(MBBA, 22~47° C.)

(b)
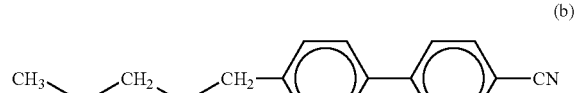
4-cyano-4'-n-pentylbiphenyl
(CB-5, 22.5~35° C.)

(c)
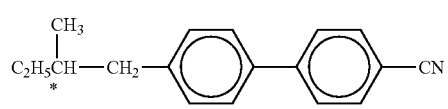
(BDH, CB-15)

(d)
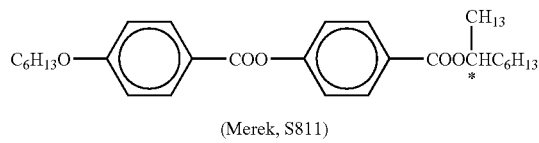
(Merek, S811)

Figure 11:
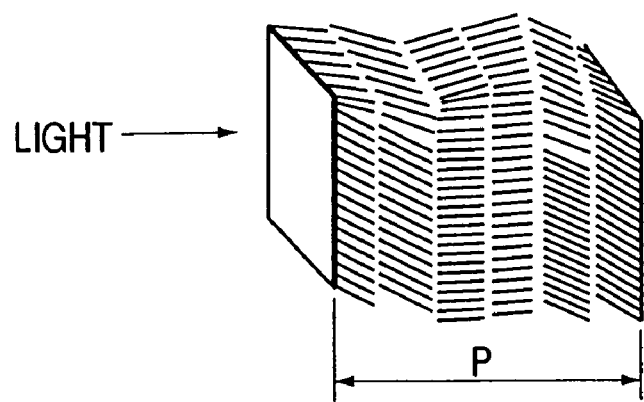
FIG. 11 is a schematic view showing a smectic liquid crystal.

Although in the above description the liquid crystal 1 used in the variable focal-length lens is employed as the nematic liquid crystal, the present invention is not limited to this, and can also use a smectic liquid crystal, such as that illustrated in FIG. 11, as a modification example of the variable focal-length lens. This figure shows the molecular arrangement of the liquid crystal of a smectic C phase. The structure of a variable focal-length lens using this liquid crystal is shown in FIG. 12.

Figure 12:
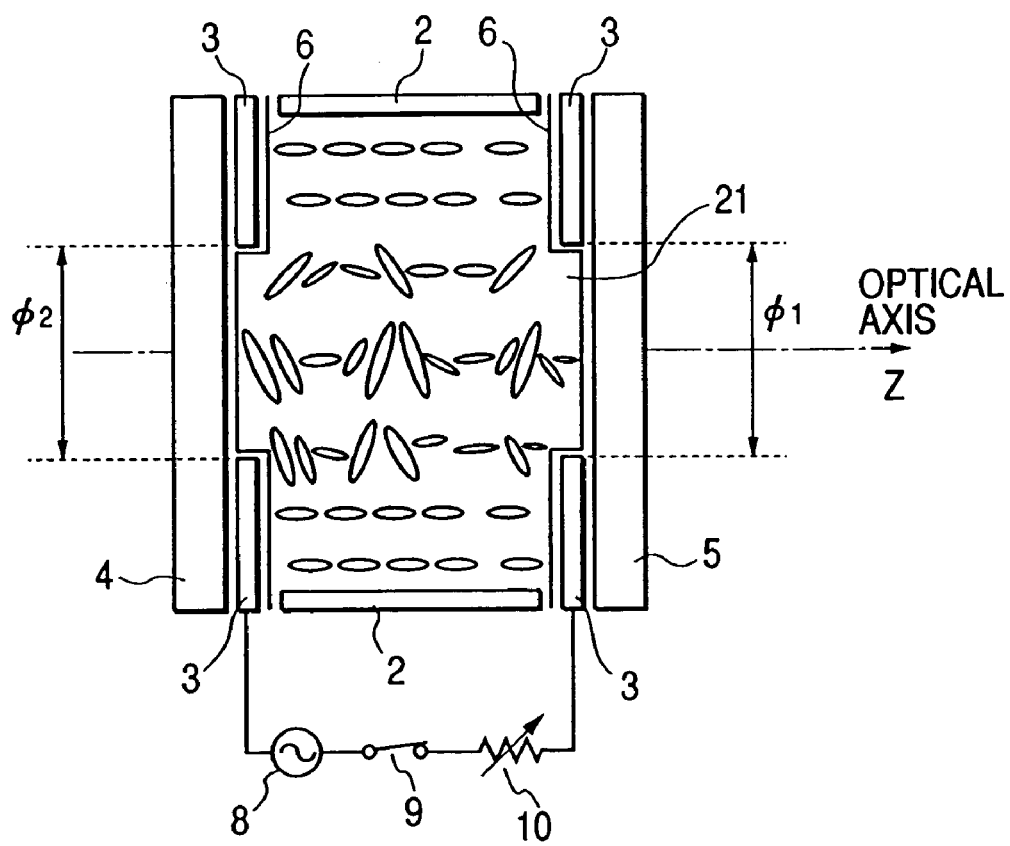
FIG. 12 is a view showing a state of a molecular orientation where an electric field is applied to a variable optical-property element using the smectic liquid crystal.

When a voltage is applied to the liquid crystal, the liquid crystal molecules of individual layers sandwiched between a pair of electrodes 3, as shown in FIG. 12, are oriented in the direction of the z coordinate axis. In this way, the refractive index of a smectic liquid crystal 21 is reduced from the refractive index n' on the optical axis to the refractive index n₀ on the periphery, so that the focal length of the variable focal-length lens is changed.

Equations and Conditions (1)-(30) also hold for the modification example shown in FIGS. 11 and 12, and in particular, if Conditions (26) and (28)-(30) are satisfied, a variable focal-length lens which produces an image with little blurring is obtained. Even with the construction of FIG. 12, the voltage applied to the smectic liquid crystal 21 can be continuously changed, and the focal length is also continuously changed at the same time.

In addition, as shown in FIG. 12, the pair of electrodes 3 have center holes φ₁ and φ₂ which are different from each other, and thereby the refractive index of the smectic liquid crystal 21 can be changed so that aberration is reduced to a minimum. This is applicable to the variable focal-length lenses shown in FIGS. 5 and 13.

Here, a design example of the variable focal-length lens using the smectic liquid crystal 21 is shown. When respective parameters are set as follows:

d 25μ
λ=0.55μ
ne−n₀=0.3
P=1.0μ
φ₁=50μ
φ₂=70μ then

Γ/2Φ=1/2·0.3×1.0/0.55=0.2725

This satisfies Conditions (26) and (28)-(30).

Also, as an example of the molecular structure of the smectic liquid crystal 21, the chemical formula of 4-(n-hexyloxy)phenyloxy-4"-(2-methylbutyl) biphenyl-4'-carboxylate is shown below. The pitch P is about 0.2μ.

(e)
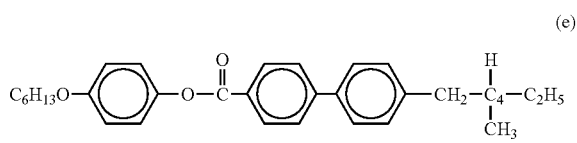

Figure 13:
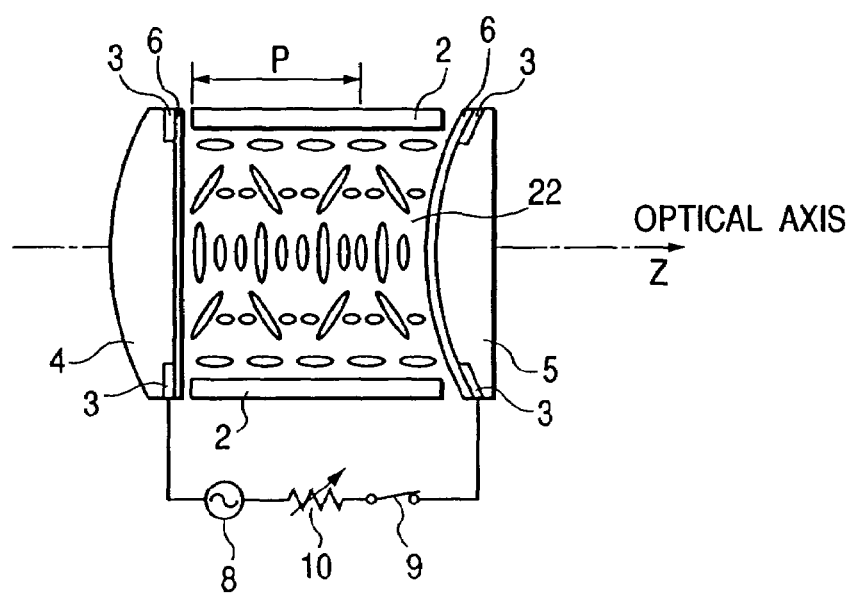
FIG. 13 is a schematic view showing a variable optical-property element using a cholesteric liquid crystal.

As another modification example of the variable focal-length lens, as shown in FIG. 13, a variable focal-length lens using a cholesteric liquid crystal 22 can be constructed. In the case of the cholesteric liquid crystal 22, its liquid crystal molecules are oriented nearly parallel to the lens surface in individual layers, and the angle of orientation is changed in helical fashion along the direction of the z axis at the period P. Equations and Conditions (1)-(30) apply to this state. When the voltage is applied, the liquid crystal molecules cease to be helically oriented in going from the optical axis to the periphery, and the function of a positive lens is produced. Furthermore, in the variable focal-length lens of this example, the inside surface of the substrate 5 is shaped into a positive lens form so that a lens effect caused by the configuration of the cholesteric liquid crystal 22 is also brought about. The inside surface of the substrate 5 may be shaped into a Fresnel lens form.

Figure 14:
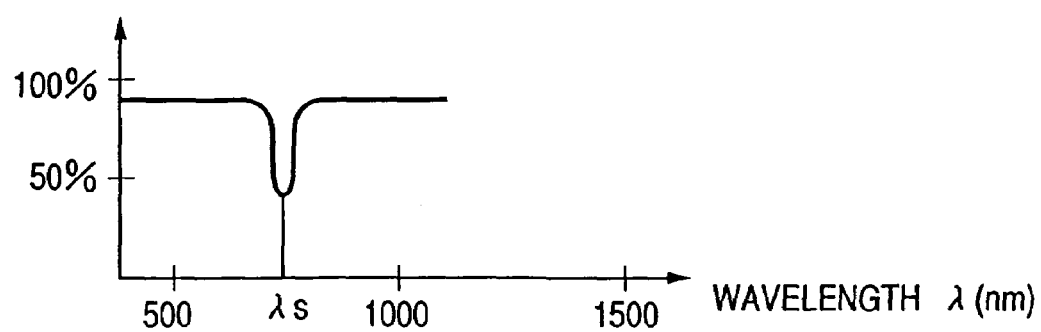
FIG. 14 is a diagram of a characteristic curve showing the actual measured value of the reflectance of the cholesteric liquid crystal against the wavelength.

The cholesteric liquid crystal 22 has the property of selective reflection and totally reflects right- or left-handed circularly polarized light practically having a wavelength λs=P·n'. FIG. 14 shows a graph of the actual measured value of the reflectance of the cholesteric liquid crystal against naturally polarized light.

As such, it is desirable that the wavelength $\lambda s$ is outside the range of wavelengths of light used in the variable focal-length lens. That is, in order to obtain a liquid crystal which is higher in transmittance and colorless, it is necessary that the value of $P \cdot n'$ is outside the wavelength region of light used in the variable focal-length lens. If the light is visible light, it is necessary to satisfy the following condition:

$$P \cdot n' < 0.4\mu \text{ or } P \cdot n' > 0.7\mu \quad (34)$$

Also, even with the liquid crystal of the smectic C phase shown in FIG. 11 or the nematic liquid crystal having the structure of the period P or a helical orientation, the selective reflection sometimes occurs, and for the above reason, Condition (34) is also applicable to the case shown in FIG. 11 or any liquid crystal having the structure of the period P or the helical orientation.

A design example of the variable focal-length lens using the cholesteric liquid crystal 22 is shown below. When respective parameters are set as follows:

$d=15\mu$
$\lambda=0.45\mu$
$ne-n_0=0.4$
$P=0.01\mu$
$n'=1.7$
$\phi=300\mu$ then $$\Gamma/2\Phi = 1/2 \cdot 0.4 \times 0.01/0.45 = 0.00445$$

This satisfies Conditions (26) and (28)-(30). Since $P \cdot n'=0.017\mu$, Condition (34) is also satisfied.

The following is the chemical formula of cholesteryl benzoate shown as an example of the cholesteric liquid crystal 22.

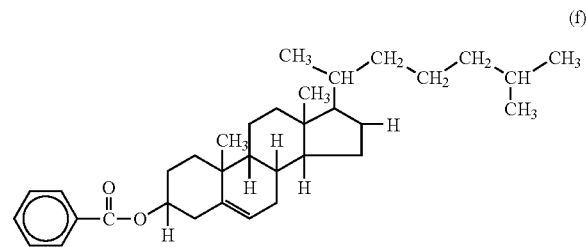

(f)

As an example of the variable focal-length lens, a discotic liquid crystal may be used instead of the cholesteric liquid crystal 22.

As is true of any of the embodiments described above and later, it is desirable that the helical pitch P is smaller than the wavelength $\lambda$ of light used or less than about 20 times the wavelength in order to obtain a variable focal-length lens which produces an image with little blurring. For example, in an optical apparatus using visible light under the condition of $0.4\mu < \lambda < 0.7\mu$, it is desirable to satisfy the following condition:

$$0.001\mu < P < 14\mu \quad (35)$$

In order to completely reduce the blurring of the image, it is necessary to satisfy the following condition:

$$0.001\mu < P \leq 5\mu \quad (36)$$

The lower limit of the pitch P is determined by the size of the liquid crystal molecule itself.

Figure 15:
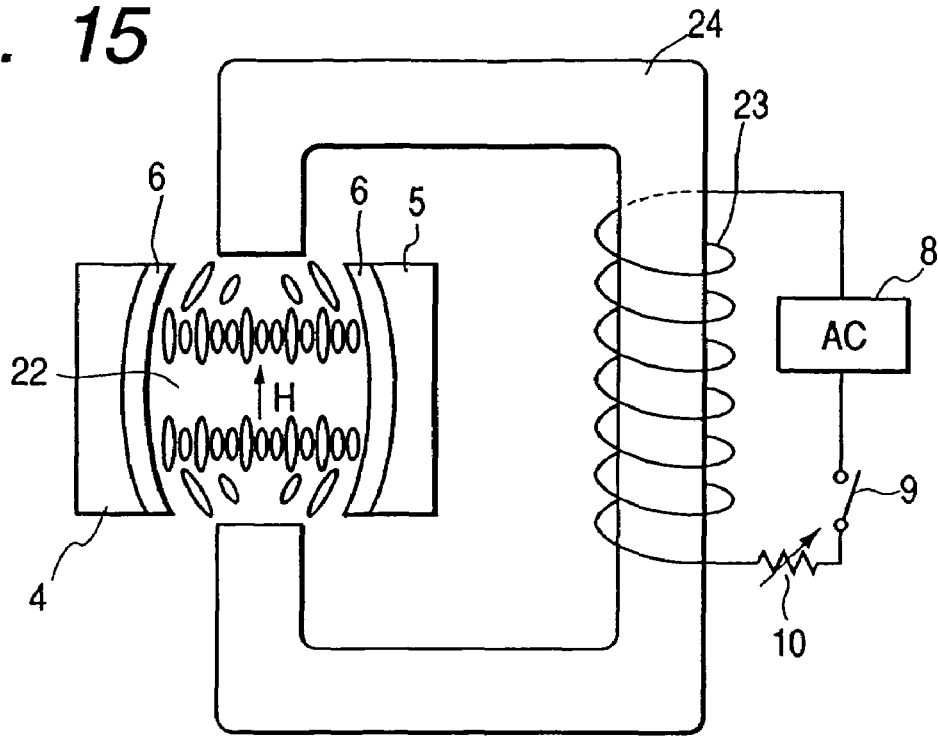
FIG. 15 is a schematic view showing a variable optical-property element constructed so that a magnetic field is applied to the cholesteric liquid crystal to change the refractive index.

Although each of the embodiment and the modification examples mentioned above uses the electric field to change the orientation of the liquid crystal, the present invention is not limited to this, and as shown n FIG. 15, a coil 23 and an iron core 24 may be used, for example, to apply a magnetic field H to the cholesteric liquid crystal 22 so that the orientation of the liquid crystal molecules is shifted by spatial unevenness of the magnetic field and the refractive index is changed. Also, although the liquid crystal lens shown in FIG. 15 is an example of the variable focal-length lens including the cholesteric liquid crystal 22, it may be used as the variable focal-length lens including the nematic liquid crystal 1 or the smectic liquid crystal 21.

Figure 16:
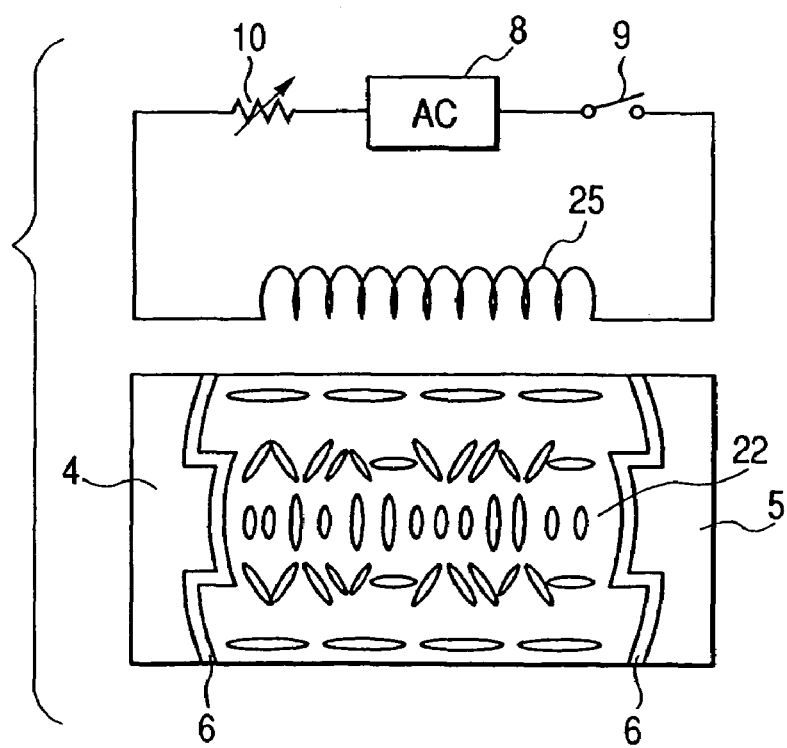
FIG. 16 is a schematic view showing a variable optical-property element constructed so that heat is applied to the cholesteric liquid crystal to change the refractive index.

To change the orientation of the liquid crystal molecules, as shown in FIG. 16, a heater 25 may be used so that, for example, the orientation of the cholesteric liquid crystal 22 is shifted in accordance with a change in temperature. This is also applicable to each of the variable focal-length lenses using other liquid crystals so far discussed, such as the nematic liquid crystal 1 and the smectic liquid crystal 21. The construction in FIG. 16 is such that the change of temperature causes a phase transition to the liquid crystal and thereby the focal length of the lens is changed. Each of the substrates 4 and 5 may be shaped into a Fresnel lens form.

In the above description, it is favorable that the pitch P in the liquid crystal is much smaller than the wavelength $\lambda$. Actually, however, cases sometimes occur in which the pitch P 10-50 times larger than the wavelength $\lambda$ is usable. Now, consider such a case using Equation (10) and Condition (30). That is, $$|1/2(ne-n_0)P/\lambda| < \pi$$

Here, when $\lambda=0.5\mu$ and $ne-n_0=0.2$, the following condition is obtained:

$$P < 10\pi\lambda = 31.4\mu \quad (37)$$

Although Conditions (28)-(30) refer to the liquid crystal in the vicinity of the optical axis in FIG. 9, a part of the liquid crystal which lies at some distance away from the optical axis includes molecules obliquely oriented, and thus an effective value of $ne-n_0$ is smaller than that in the vicinity of the optical axis. Therefore, Condition (37) can be made easier in view of the entire liquid crystal lens, and it is only necessary to satisfy the following condition:

$$P < 60\mu \quad (38)$$

In an optical system with a somewhat high degree of accuracy, similarly from Condition (28), it is only necessary to satisfy the following condition:

$$P < 20\mu \quad (39)$$

Where the value of the pitch P varies with the place of the liquid crystal, it is common practice to take the average of pitches derived from individual places.

Figure 17:
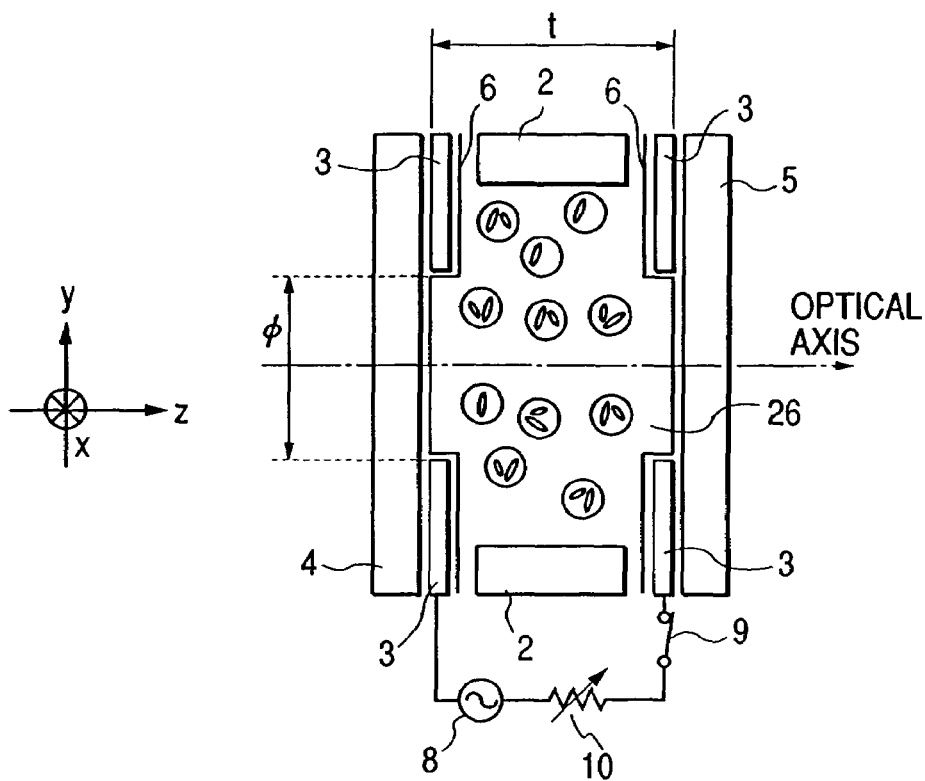
FIG. 17 is a schematic view showing a variable optical-property element using a macromolecular dispersed liquid crystal layer.
Figure 18:
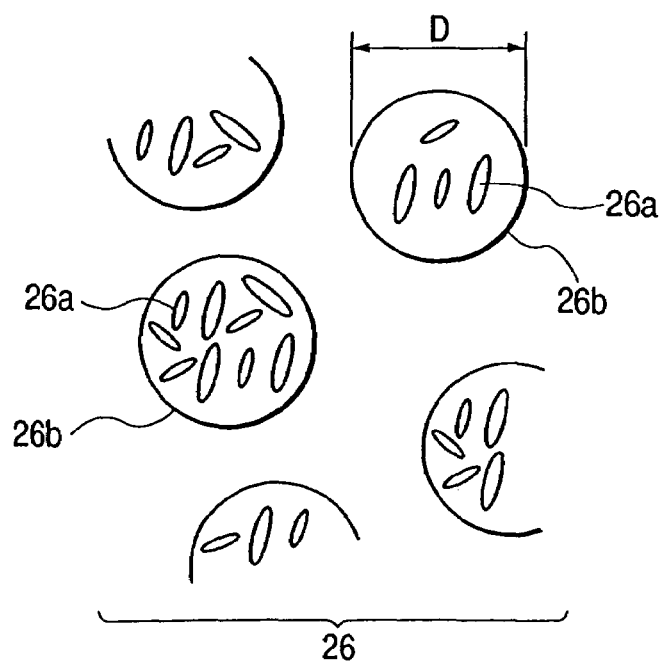
FIG. 18 is a partially enlarged view showing the macromolecular dispersed liquid crystal layer in FIG. 17.

FIG. 17 shows another modification example of the variable focal-length lens of the present invention, using a macromolecular dispersed liquid crystal layer 27. Specifically, in this variable focal-length lens, the macromolecular dispersed liquid crystal layer 26 is interposed between the pair of substrates 4 and 5 so that when the switch 9 is turned on, the electric field is applied to the macromolecular dispersed liquid crystal layer 26 through the electrodes 3. The macromolecular dispersed liquid crystal layer 26, as illustrated in FIG. 18, is composed of a great number of minute macromolecular cells 26b of any shape, such as a sphere or polyhedron, each including liquid crystal molecules 26a.

Here, for the size of each of the macromolecular cells 26b, when an average diameter, for example, in the case of the sphere, is denoted by D and the wavelength of light used is denoted by λ, for example, the average diameter D is chosen so as to satisfy, for example, the following condition:

$$2 \text{ nm} \leq D \leq \lambda/5 \qquad (40)$$

That is, the size of each of the liquid crystal molecules 26a is at least about 2 nm and thus the lower limit of the diameter D is set to be at least 2 nm. The upper limit of the diameter D depends on a thickness t of the macromolecular dispersed liquid crystal layer 26 in the direction of the optical axis of the variable focal-length lens. However, if the diameter D is larger than the wavelength λ, a difference between the refractive indices of the macromolecules and the liquid crystal molecules 26a will cause light to be scattered at the interfaces of the macromolecular cells 26b and will render the liquid crystal layer 26 opaque. Hence, the upper limit of the diameter D should be below the wavelength λ, or preferably λ/5 or less, as mentioned later. Also, the transparency of the liquid crystal layer 26 deteriorates with increasing thickness t.

Figure 19:
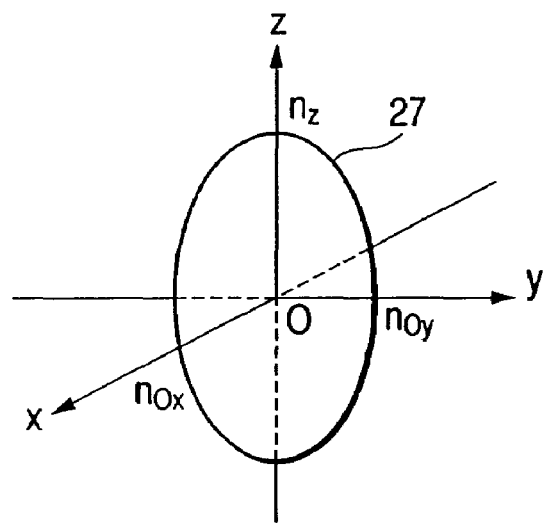
FIG. 19 is a view showing the index ellipsoid of a uniaxial nematic liquid crystal molecule in FIG. 17.

For the liquid crystal molecules 26a, uniaxial nematic liquid crystal molecules are used. The index ellipsoid of each of the liquid crystal molecules 26a is as shown in FIG. 19. That is, $$n_{ox} = n_{oy} = n_0 \qquad (41)$$

where $n_{ox}$ and $n_{oy}$ are refractive indices in directions perpendicular to each other in a plane including ordinary rays.

Figure 20:
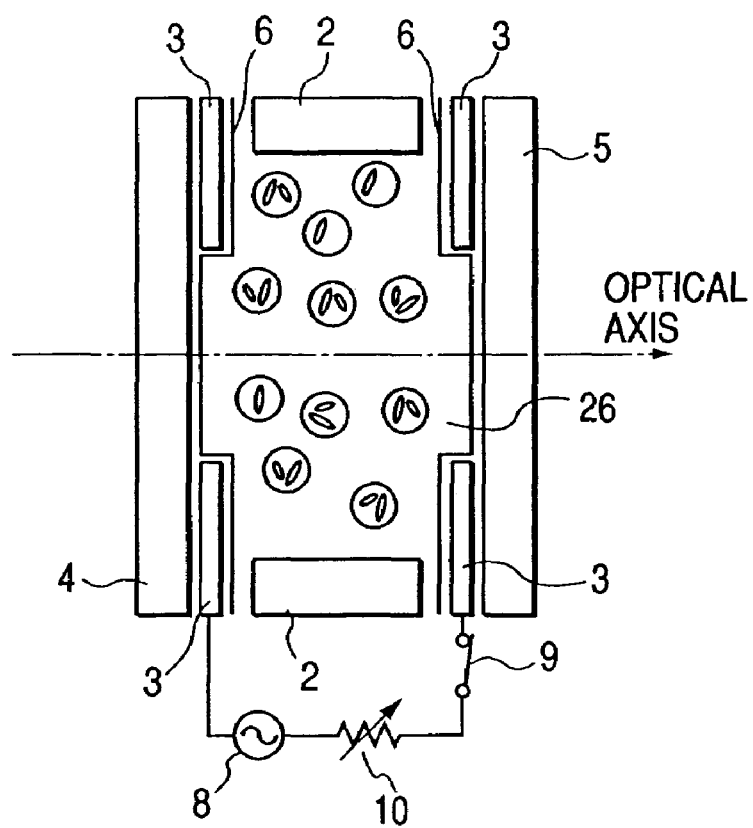
FIG. 20 is a view showing a state of the orientation of liquid crystal molecules where an electric field is applied to the variable optical-property element of FIG. 17.

Here, in the case where the switch 9, as shown in FIG. 17, is turned off, that is, the electric field is not applied to the liquid crystal layer 26, the liquid crystal molecules 26a are oriented in various directions, and thus the variable focal-length lens becomes equivalent to a plane-parallel plate and fails to function as a lens. When the focal length of the variable focal-length lens in this case is represented by $f_1$, $f_1 = \infty$. In contrast to this, when the switch 9, as shown in FIG. 20, is turned on, a portion sandwiched between the pair of electrodes 3 shows a tendency that the liquid crystal molecules 26a are oriented perpendicular to the substrates 4 and 5. Subsequently, the liquid crystal molecules 26a are oriented to become oblique with respect to the optical axis in going from the periphery to the optical axis, and are randomly oriented in the vicinity of the optical axis. Consequently, the molecular orientation of the liquid crystal in the vicinity of the optical axis is almost the same as in FIG. 17. In this way, the refractive index of the liquid crystal 26 is high in the vicinity of the optical axis, but reduces progressively in going from the optical axis to the periphery. The variable focal-length lens thus behaves as an inhomogeneous lens possessing the function of a positive lens.

If the number of macromolecules is increased, the macromolecular dispersed liquid crystal layer 26 approaches a solid. In this case, at least one of the substrates 4 and 5 may be eliminated. This is applicable to the variable focal-length lenses shown in FIGS. 22 and 23 described later.

The voltage applied to the macromolecular dispersed liquid crystal layer 26, as shown in FIG. 17, can also be changed gradually or continuously by the variable resistor 10. By doing so, the liquid crystal molecules 26a are oriented so that their major axes progressively become parallel with the optical axis of the variable focal-length lens as the applied voltage is increased. Hence, the refractive index can be changed gradually or continuously.

Here, in the case of FIG. 17, that is, where the electric field is not applied to the liquid crystal layer 26, when the refractive index in the direction of the major axis of the index ellipsoid, as shown in FIG. 19, is denoted by $n_z$, an average refractive index $n_{LC}'$ of the liquid crystal molecules 26a is roughly given by $$(n_{ox} + n_{oy} + n_z)/3 \equiv n_{LC}' \qquad (42)$$

Also, when the refractive index $n_z$ is expressed as the refractive index ne of an extraordinary ray, an average refractive index $n_{LC}$ where Equation (41) is established is given by $$(2n_0 + ne)/3 \equiv n_{LC} \qquad (43)$$

In this case, when the refractive index of each of the macromolecules constituting the macromolecular cells 26b is represented by $n_P$ and the ratio of volume between the liquid crystal layer 26 and the liquid crystal molecules 26a is represented by ff, a refractive index $n_A$ of the liquid crystal layer 26 is given from the Maxwell-Garnet's law as $$n_A = ff \cdot n_{LC}' + (1-ff)n_P \qquad (44)$$

When the average refractive index of extraordinary rays is expressed as $$(n_{ox} + n_{oy})/2 = n_0' \qquad (45)$$

a refractive index $n_B$ of the liquid crystal layer 26 between the electrodes 3 in the case of FIG. 20, that is, where the electric field is applied to the liquid crystal layer 26, is given by $$n_B = ff \cdot n_0' + (1-ff)n_P \qquad (46)$$

Assuming that in the case of FIG. 20 the refractive index of the liquid crystal layer 26 varies as the square of a distance y from the optical axis, attempt to find a focal length $f_2$ of the variable focal-length lens. When an index coefficient is denoted by $n_{02}$, a refractive index n(y) of the liquid crystal layer 26 at the distance y is expressed as $$n(y) = n_0 + n_{02}y^2 \qquad (47)$$

In this case, the following equation is approximately established:

$$f_2^{-1} \approx -2n_{02}t \qquad (48)$$

Equation (47) is rewritten as follows:

$$n(y) - n_0 = n_{02}y^2 \qquad (49)$$

Since $n(y) = n_B$ and $n_0 = n_A$ in the periphery of the lens, the following equations are obtained:

$$n_B - n_A = n_{02}y^2 \qquad (50)$$

$$f_2 = -y^2/\{2(n_B - n_A)t\} \qquad (51)$$

To bring about a great change of the focal length by the macromolecular dispersed liquid crystal layer 26, it is only necessary to increase the value of $|n_B - n_A|$ in Equation (51). Here, $$n_B - n_A = ff(n_0' - n_{LC}') \qquad (52)$$

Thus, if the value of $|n_0'-n_{LC}'|$ is increased, a change rate can be raised. Practically, the refractive index $n_B$ is about 1.3-2, and thus the value of $|n_0'-n_{LC}'|$ is chosen so as to satisfy the following condition:

$$0.01 \leq |n_0'-n_{LC}'| \leq 10 \tag{53}$$

In this way, when ff=0.5, the focal length obtained by the liquid crystal layer 26 can be changed by at least 0.5%, and hence an effective variable focal-length lens can be derived. Also, the value of $|n_0'-n_{LC}'|$ cannot exceed 10 because of restrictions on liquid crystal substances.

Subsequently, a description will be given of grounds for the upper limit of Condition (40). The variation of a transmittance τ where the size of the cells of a macromolecular dispersed liquid crystal is changed is described in "Transmission variation using scattering/transparent switching films" on pages 197-214 of "Solar Energy Materials and Solar Cells", by Wilson and Eck, Vol. 31, Elesvier Science Publisher B. v., 1933. In FIG. 6 on page 206 of this publication, it is shown that when the radius of the macromolecular dispersed is denoted by r, t=300 μm, ff=0.5, $n_P$=1.45, $n_{LC}$=1.585, and λ=500 nm, the theoretical value of the transmittance τ is about 90%0 if r=5 nm (D=λ/50, and D·t=λ·6 μm, where D and λ are expressed in nanometers), and is about 50% if r=25 nm (D=λ/10).

Here, assuming that t=150 μm and the transmittance τ varies as the exponential function of the thickness t, consider the transmittance τ in this case. When r=25 nm (D=λ/10, and D·t=λ·15 μm), the transmittance τ becomes nearly 71%. Similarly, in the case where t=75 μm, when r=25 nm (D=λ/10, and D·t=λ·7.5 μm), the transmittance τ becomes nearly 80%.

From these results, the transmittance τ becomes at least 70-80% and the liquid crystal lens can be actually used as a lens if the following condition is satisfied:

$$D \cdot t \leq \lambda \cdot 15 \, \mu m \tag{54}$$

Hence, for example, in the case where t=75 μm, if D≤λ/5, a satisfactory transmittance can be obtained.

The transmittance of the macromolecular dispersed liquid crystal layer 26 is raised as the value of the refractive index $n_P$ approaches the value of the refractive index $n_{LC}'$. On the other hand, if the values of the refractive indices $n_0'$ and $n_P$ are different from each other, the transmittance of the liquid crystal layer 26 will be impaired. In FIGS. 17 and 20, the transmittance of the liquid crystal layer 26 is improved on an average when the liquid crystal layer 26 practically satisfies the following equation:

$$n_P = (n_0' + n_{LC}')/2 \tag{55}$$

The variable focal-length lens is used as a lens, and thus, in both FIGS. 17 and 20, it is desirable that the transmittances are almost the same and high. For this, although there is a limit to the substances of the macromolecules constituting the macromolecular cells 26b and the liquid crystal molecules 26a, it is only necessary, in practical use, to satisfy the following condition:

$$n_0' \leq n_P \leq n_{LC}' \tag{56}$$

When Equation (55) is practically satisfied, Condition (54) is moderated to the following condition:

$$D \cdot t \leq \lambda \cdot 60 \, \mu m \tag{57}$$

It is for this reason that, according to the Fresnel's law of reflection, the reflectance is proportional to the square of the difference of the refractive index, and thus the reflection of light at the interface between the macromolecules constituting the macromolecular cells 26b and the liquid crystal molecules 26a, that is, a reduction in the transmittance of the liquid crystal layer 26, is roughly proportional to the square of the difference in refractive index between the macromolecules and the liquid crystal molecules 26a. In Condition (57), if t=75 μm, then D≤0.8λ, and it is only necessary to practically satisfy the condition: D≤λ.

In the above description, reference has been made to the case where $n_0' \approx 1.45$ and $n_{LC}' \approx 1.585$, but in a general formulation, the following condition is satisfactory:

$$D \cdot t \leq \lambda \cdot 15 \, \mu m \cdot (1.585-1.45)^2/(n_u-n_P)^2 \tag{58}$$

where $(n_u-n_P)^2$ is a value when one of $(n_{LC}'-n_P)^2$ and $(n^{ot}-n_P)^2$ is larger than the other.

In order to largely change the focal length of the variable focal-length lens, it is favorable that the ratio ff is as high as possible, but in the case of (ff=1), the volume of the macromolecules becomes zero and the macromolecular cells 26b cease to be formed. Thus, it is necessary to satisfy the following condition:

$$0.1 \leq ff \leq 0.999 \tag{59}$$

On the other hand, the transmittance τ improves as the ratio ff becomes low, and thus Condition (58) may be moderated, preferably, as follows:

$$4 \times 10^{-6} [\mu m]^2 \leq D \cdot t \leq \lambda \cdot 45 \, \mu m \cdot (1.585-1.45)^2/(n_u-n_P)^2 \tag{60}$$

Also, the lower limit of the thickness t, as is obvious from FIG. 17, corresponds to the diameter D, which is at least 2 nm as described above, and hence the lower limit of D·t becomes $(2 \times 10^{-3} \, \mu m)^2$, namely $4 \times 10^{-6} \, [\mu m]^2$.

In the above description, reference has been made to the case where a fairly good value is required for the scattering of light caused by the variable focal-length lens and the transmittance thereof. However, for a low-cost optical system and the illumination signal processing system of an imaging device, such values are not necessarily required, and Condition (60) can be further moderated as follows:

$$4 \times 10^{-6} [\mu m]^2 \leq D \cdot t \leq \lambda \cdot 450 \, \mu m \cdot (1.585-1.45)^2/(n_u-n_P)^2 \tag{61}$$

An approximation that the optical property of substance is represented by the refractive index is established when the diameter D is 5-10 nm or more, as set forth on page 58 of "Iwanami Science Library 8, Asteroids are coming", by T. Mukai, Iwanami Shoten, 1994. If the value of the diameter D exceeds 500λ, the scattering of light will be changed geometrically, and the scattering of light at the interface between the macromolecules constituting the macromolecular cells 26b and the liquid crystal molecules 26a is increased in accordance with the Fresnel's formula of reflection. As such, in practical use, the diameter D must be chosen so as to satisfy the following condition:

$$7 \, nm \leq D \leq 500\lambda \tag{62}$$

In the construction shown in FIG. 17, the values of individual parameters of the above equations and the effective diameter ϕ are specifically set as follows:

$n_{ox}=n_{oy}=n_0=1.5$
$n_z=ne=1.75$
$n_P=1.54$
ff=0.5
D=50 nm
t=125 μm
λ=500 nm
$n_{LC}'=n_{LC}=1.5833$
$n_A=1.5617$ $n_B=1.52$
$f_1=\infty$
$f_2=599.5$ mm
$\phi=5$ mm Consequently, the right side of Condition (60) is as follows:

$$\lambda \cdot 45 \ \mu m \cdot (1.585-1.45)^2/(n_u-n_P)^2$$

$$=500 \ nm \cdot 45 \ \mu m \cdot (0.135)^2/(0.0433)^2 \approx 218712 \ nm \cdot \mu m$$

The value of D·t is $$D \cdot t = 50 \ nm \cdot 125 \ \mu m = 6250 \ nm \cdot \mu m$$

This indeed satisfies Condition (60). In the above specific examples, the substrates 4 and 5 can be configured to have curved surfaces as in ordinary lenses.

Figure 21:
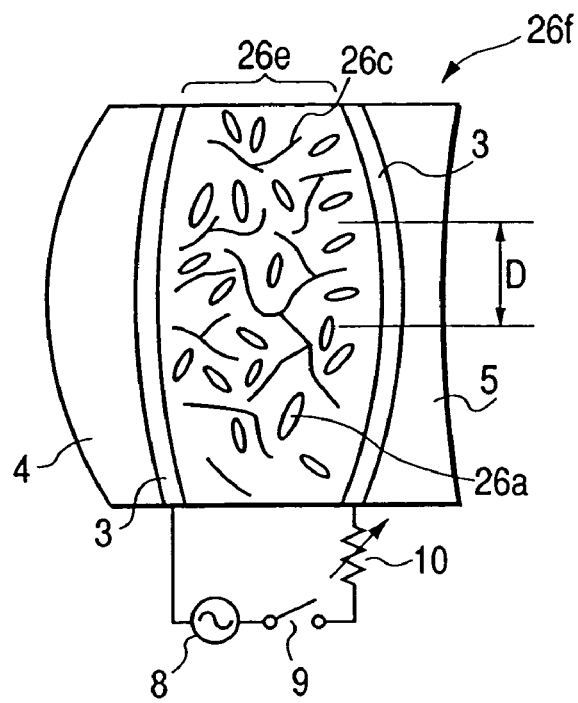
FIG. 21 is a view showing a variable optical-property element using a macromolecular stabilized liquid crystal.

In the disclosure so far, reference has been made to the variable focal-length lens using the macromolecular dispersed liquid crystal. However, in FIG. 21, the conditions relating to the parameters, such as D, t, ff, and respective n's, also hold for the case of a variable focal-length lens 26f using a macromolecular stabilized liquid crystal 26e. The macromolecular stabilized liquid crystal refers to a liquid crystal in which network macromolecules 26c are mixed with liquid crystal molecules 26a and are interposed between the liquid crystal molecules at the distance D on an average, although the liquid crystal is not clearly separated into cell structures. The definitions of the parameters, such as t, ff, $n_u$, and $n_A$, are the same as the case of the macromolecular dispersed liquid crystal.

The macromolecular stabilized liquid crystal includes a variable refractive-index substance, which causes the refractive index to have a spatially uneven distribution and thereby the index distribution is changed. A substance in which the refractive index is changed periodically in one direction can be used as the variable refractive-index substance. Moreover, the variable refractive-index substance can also be used in such a way that the frequency of the electric or magnetic field is changed to control the orientation of liquid crystal molecules.

In order to make a member for controlling the direction of the arrangement or the orientation of the molecules of the variable refractive-index substance, photoresist exposure and etching or lithographic technology is used. In addition, the variable refractive-index substance may have a structure such that the electric or magnetic field is applied in a direction nearly perpendicular to the optical axis.

Figure 22:
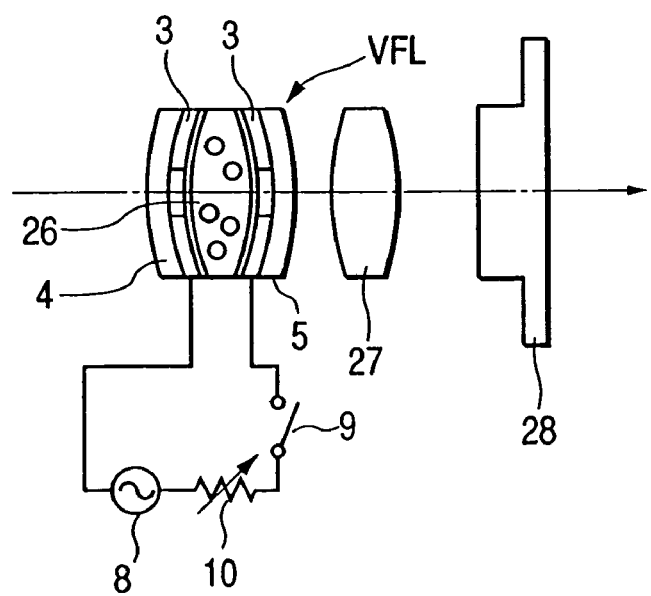
FIG. 22 is a view showing an imaging optical system for digital cameras, using the variable optical-property element of FIG. 17.

FIG. 22 shows an imaging optical system for digital cameras using the variable focal-length lens in FIG. 17. In this imaging optical system, an image of an object (not shown) is formed, through a variable focal-length lens VFL and a lens 27, on a solid-state image sensor 28 including a CCD, for instance. Also, the liquid crystal molecules 26a are not shown in FIG. 22. The electrodes 3 are also used as the stops of this optical system, and the substrates 4 and 5 have curved surfaces.

According to the imaging optical system in the foregoing, an AC voltage applied to the macromolecular dispersed liquid crystal layer 26 of the variable focal-length lens VFL is controlled by the variable resistor 10, and thereby the focal length of the variable focal-length lens VFL is changed. In this way, it becomes possible to continuously perform a focusing operation with respect to an object distance, for example, from infinity to 600 mm, without moving the variable focal-length lens VFL and the lens 27 along the optical axis.

Figure 23:
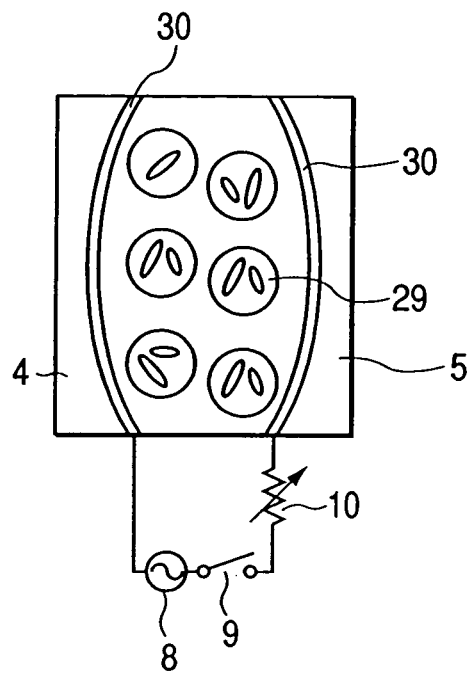
FIG. 23 is a schematic view showing a variable optical-property element using a ferroelectric liquid crystal.

FIG. 23 shows a modification example of the variable focal-length lens using a ferroelectric liquid crystal 29. In this figure, reference numeral 30 designates transparent electrodes. Since at least one of the substrates 4 and 5 has a curved surface, this variable focal-length lens possesses a lens function even though the electric field applied is uniform. The lens function can be varied by the variable resistor 10. Instead of the ferroelectric liquid crystal 29, antiferroelectric liquid crystal may be employed. In either case, this liquid crystal, in contrast with the nematic liquid crystal, has the advantage that its response time is quick. Even with the macromolecular dispersed liquid crystal lens using either the ferroelectric liquid crystal or the antiferroelectric liquid crystal, Conditions and Equations (40)-(46) and (52)-(62) are applicable.

As is true of all the liquid crystals in the present invention, the Abbe's number (usually represented by $v_d$) of the liquid crystal is small and about 10-40 in most cases. The liquid crystal, therefore, produces considerable chromatic aberration. In order to correct this aberration, it is desirable that at least one of the substrates 4 and 5 is shaped into a lens form and its material has an Abbe's number of 50 or less. For example, heavy flint glass corresponds to this material. It is good practice that if the liquid crystal has a positive function, at least one of the substrates is used as a negative lens, while if it has a negative function, at least one of the substrates is used as a positive lens.

Figure 24:
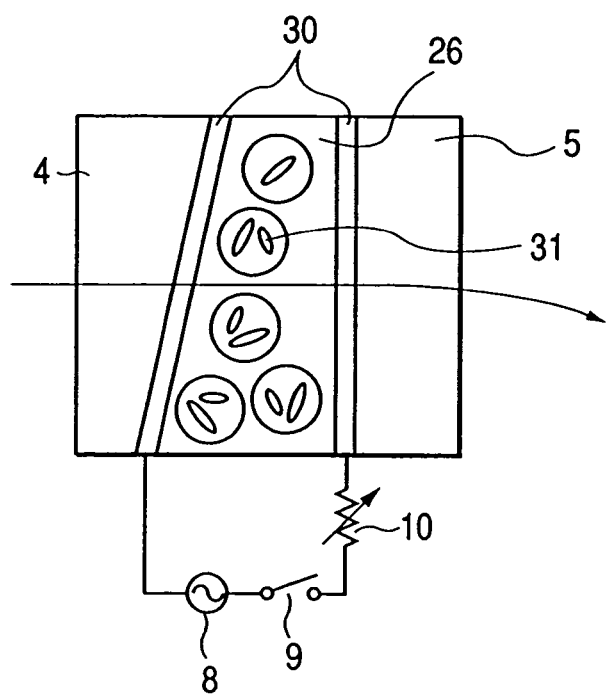
FIG. 24 is a view showing an example using a variable deflection-angle prism as the variable optical-property element according to the present invention.

FIG. 24 shows a variable deflection-angle prism used as the variable optical-property element. In this embodiment, the macromolecular dispersed liquid crystal layer 26 is sandwiched between the two substrates 4 and 5 so that light can be deflected by changing the voltage. In this case also, it is desirable that the glass material with an Abbe's number of 50 or less is used for the substrate 4. A liquid crystal 31 used here may be the nematic, ferroelectric, or antiferroelectric liquid crystal.

Figure 25:
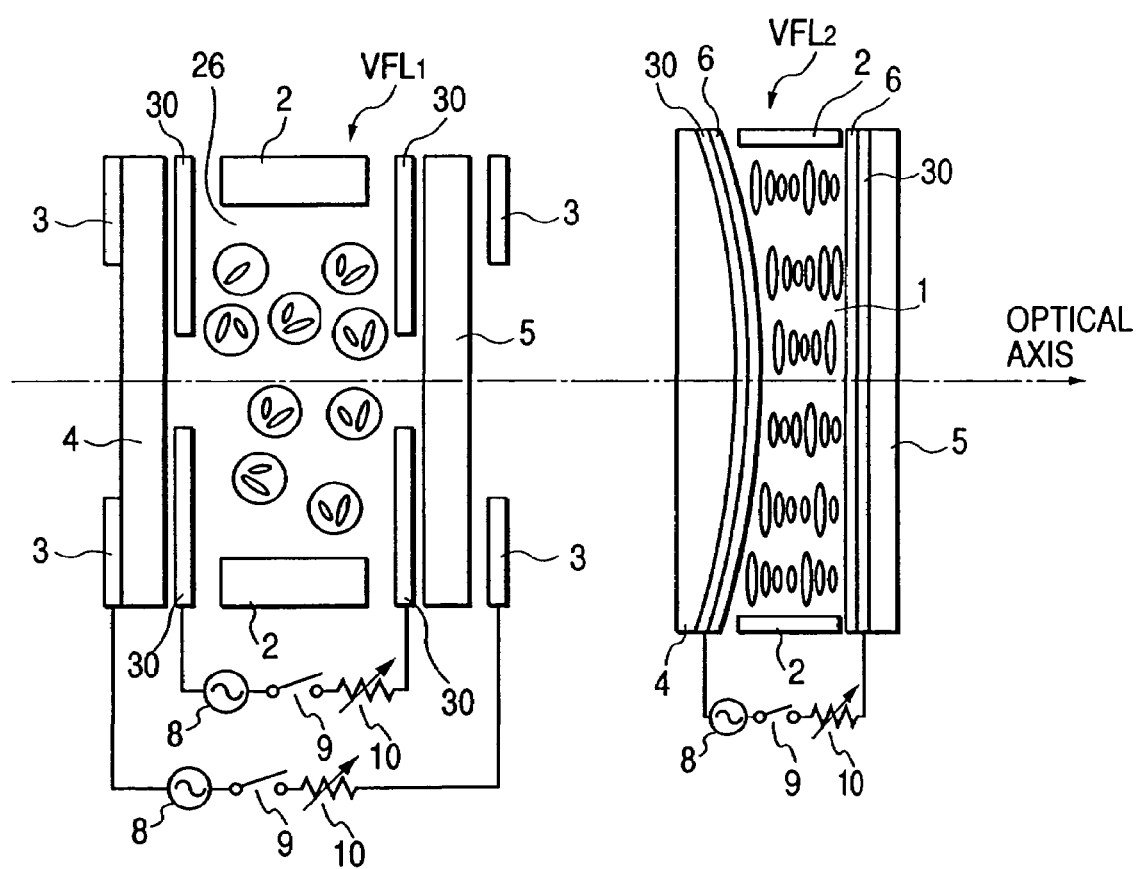
FIG. 25 is a view showing an example using two variable focal-length lens as the variable optical-property element according to the present invention.

FIG. 25 shows a combination of two variable focal-length liquid crystal lenses $VFL_1$ and $VFL_2$. The variable focal-length liquid crystal lens $VFL_1$ includes the macromolecular dispersed liquid crystal layer 26 sandwiched between respective pairs of the doughnut-shaped electrodes 3 and the substrates 4 and 5 having doughnut-shaped transparent electrodes 30. The variable resistors 10 are adjusted individually to properly choose the voltage applied across the electrodes so that the distribution of the refractive index is changed and aberration can be controlled. The variable focal-length liquid crystal lens $VFL_1$ acts as a positive variable focal-length lens. On the other hand, the variable focal-length liquid crystal lens $VFL_2$ is constructed with the substrates 4 and 5, each having a transparent electrode 30, between which the nematic liquid crystal 1 is interposed through the orientation films 6, and functions as a negative variable focal-length lens. In this way, when the two variable focal-length liquid crystal lenses $VFL_1$ and $VFL_2$ are used, the Abbe's number becomes small because both the lenses use liquid crystals, and correction for chromatic aberration is facilitated. It is required for correction for chromatic aberration that one of the lenses has a positive power and the other has a negative power.

Figure 26:
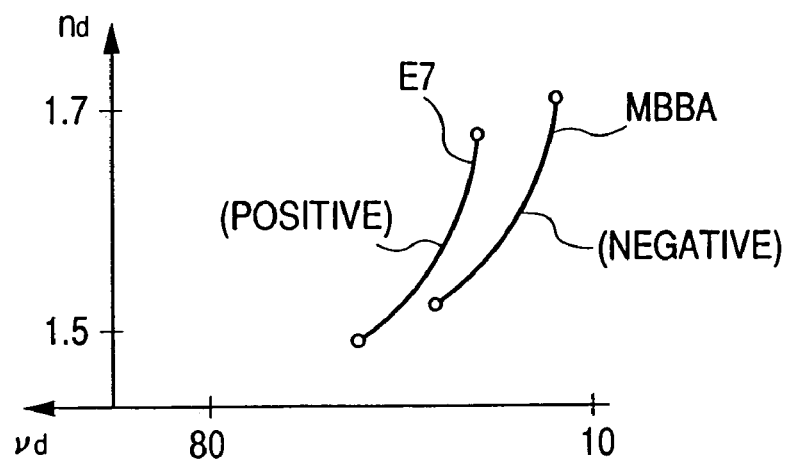
FIG. 26 is a diagram of characteristic curves showing changes in Abbe's number caused by changes in refractive index of the liquid crystal.

FIG. 26 shows characteristic curves showing the changes of the refractive index $n_d$ of the liquid crystal against the Abbe's number $v_d$. In this diagram, $n_d$-$v_d$ characteristic curves of two kinds of liquid crystals are represented. In general, there is a tendency that as the refractive index increases, the Abbe's number reduces.

Thus, where the refractive index of a lens system including the variable focal-length liquid crystal lenses $VFL_1$ and VFL$_2$ is changed, it is desirable that, in order to diminish the fluctuation of chromatic aberration, when the Abbe's number v$_d$ of one of the variable focal-length liquid crystal lenses VFL$_1$ and VFL$_2$ is relatively large, the Abbe's number v$_d$ of the other is also large. Conversely, it is favorable that when the Abbe's number v$_d$ of the one is relatively small, the Abbe's number v$_d$ of the other is also small. In order to cause this lens system to function as a positive lens system with minimum chromatic aberration, it is good practice that the Abbe's number v$_d$ of the liquid crystal lens constituting the positive lens is made large, while that of the liquid crystal lens constituting the negative lens is selected to be smaller. In the case of FIG. 26, it is desirable that a liquid crystal having characteristics represented by the left-hand curve is used for the positive lens, while a liquid crystal having characteristics represented by the right-hand curve is used for the negative lens. Also, labeled E7 and MBBA in FIG. 26 are the names of liquid crystals. The characteristic curves of the liquid crystals used for the positive and negative lenses may cross at the position where the refractive index n$_d$ is low. In short, it is only necessary that the characteristic curve of the liquid crystal for the negative lens is situated on the right side of that for the positive lens within a certain range of refractive indices. In order to eliminate chromatic aberration, it is desirable that the Abbe's number v$_d$ does not exceed 50. With reference to FIG. 25, when the focal length of the lens VFL$_1$ is denoted by F$_1$ and the focal length of the lens VFL$_2$ is denoted by F$_2$, it is desirable to satisfy the following condition in order to eliminate chromatic aberration:

$$1/2 < |F_1/F_2| < 2 \qquad (63)$$

It is for this reason that, in the case of FIG. 25, if the value of |F$_1$/F$_2$| exceeds the upper limit of Condition (63), chromatic aberration will be overcorrected, while below the lower limits chromatic aberration will be undercorrected.

As is true of the whole of the variable optical-property element of the present invention, when a tolan-base liquid crystal is used as the liquid crystal, the refractive index is considerably changed the viscosity becomes low. This reduces the response time of the liquid crystal, which is advantageous. As an example of the tolan-base liquid crystal, the chemical formula of 4-alkylcyclohexyl-4'-alkyltran is shown below.

(g)

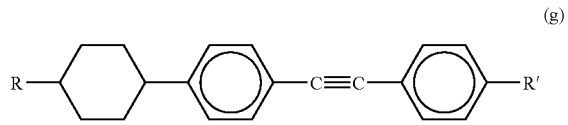

where R is an alkyl group and R' is an alkoxy group. In order to reduce the response time of the liquid crystal, it is good practice to continuously apply a low voltage to the liquid crystal. It is only necessary that this voltage is almost the same as a phase transition voltage or lower.

As is true of the whole of the variable optical-property element of the present invention, a substance having an electrooptical effect, a magnetooptical effect, or a thermooptical effect (that the refractive index is change by temperature) or a ferroelectric substance may be used instead of the liquid crystal. As an example of the substance having the electrooptical effect, barium titanate (BaTiO$_3$) is cited; as the magnetooptical effect, lead glass or quartz crystal; and as the thermooptical effect, water. The ferroelectric substance refers to, for example, barium titanate or Rochelle salt.

Figure 27:
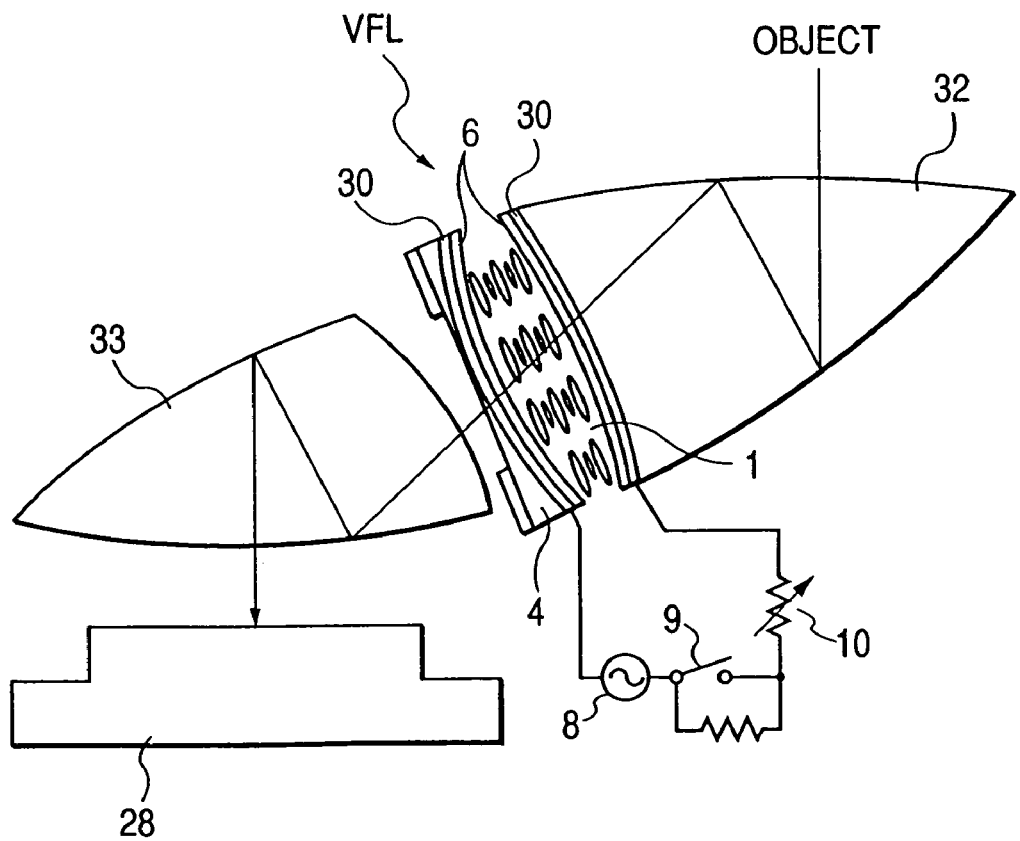
FIG. 27 is a view showing an imaging device for digital cameras in which the variable optical-property element of the present invention is combined with a free-formed surface optical element.

FIG. 27 illustrates an application example of a variable focal-length liquid crystal lens VFL in an imaging device for digital cameras using free-formed surface optical elements 32 and 33. The free-formed surface optical elements 32 and 33 have the shapes such that those described in connection with the prior art and performs an imaging function by means of reflections and refractions of decentered aspherical surfaces. They are constructed of plastic or glass, and has the disadvantage that their shapes are asymmetrical and thus when the focusing operation is performed, a mechanical structure for changing a distance to a solid-state image sensor 28 becomes complicated. In the present invention, therefore, the variable focal-length liquid crystal lens VFL is placed close to a stop between the two free-formed surface optical elements and its refracting power is changed so that the focusing operation is performed. In this case, since the focusing operation can be performed without mechanically moving the free-formed surface optical elements 32 and 33, the structure becomes simple, which is advantageous. According to this construction, one of the substrates of the variable focal-length liquid crystal lens VFL is substituted by the outer surface of the free-formed surface optical element 32, and hence cost is reduced, which is advantageous.

The optical system of the imaging device can be used in a film camera if the image sensor 28 is replaced with a film. Furthermore, by combining the free-formed surface optical elements with the variable optical-property element of the present invention, an imaging device with zoom lenses or an optical apparatus may be constructed. Instead of the free-formed surface optical elements, diffraction optical elements or aspherical lenses may also be used in combination with the variable optical-property element to construct a variable focal-length imaging device or an optical apparatus. In this case, the optical apparatus includes, for example, a pickup device for optical disks or an microscope.

The variable optical-property element according to the present invention, if, for example, it is constructed as the variable focal-length lens, can be used in an electronic camera, a TV camera, an autofocus device for electronic endoscopes, and a zoom lens system. Moreover, it can also be used in binoculars, a finder for cameras, or a diopter adjusting device or a variable magnification device of an optical instrument such as an eyepiece for microscopes. It may also be used in variable focal-length spectacles.

Figure 28:
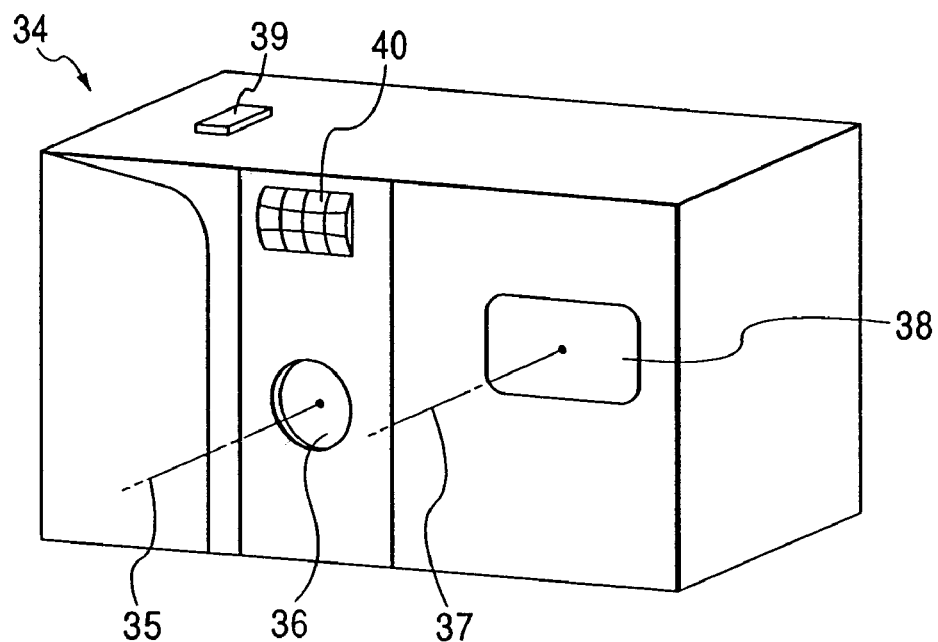
FIG. 28 is a front perspective view showing an electronic camera in which the variable optical-property element of the present invention is incorporated in a finder optical system.
Figure 29:
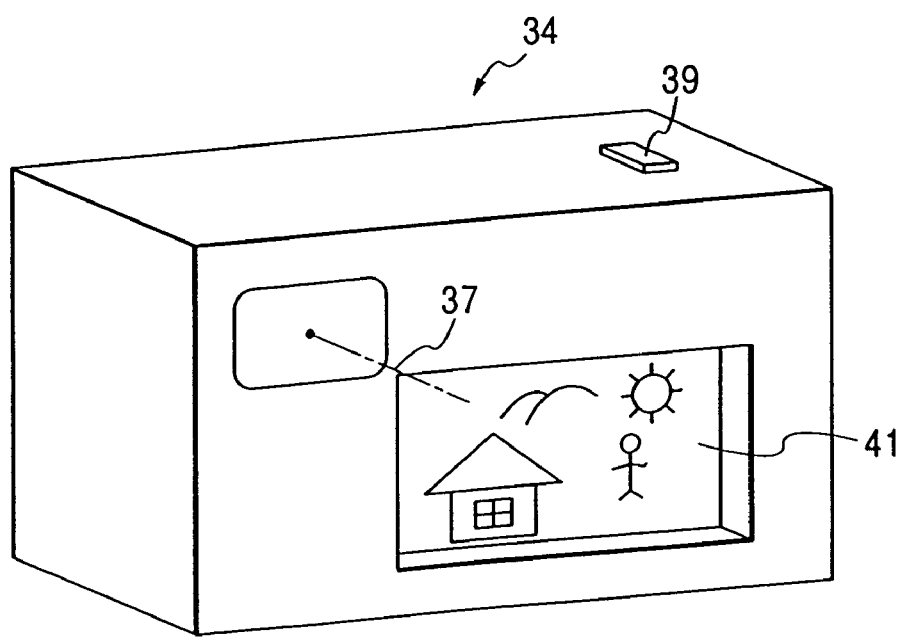
FIG. 29 is a rear perspective view showing the electronic camera of FIG. 28.
Figure 30:
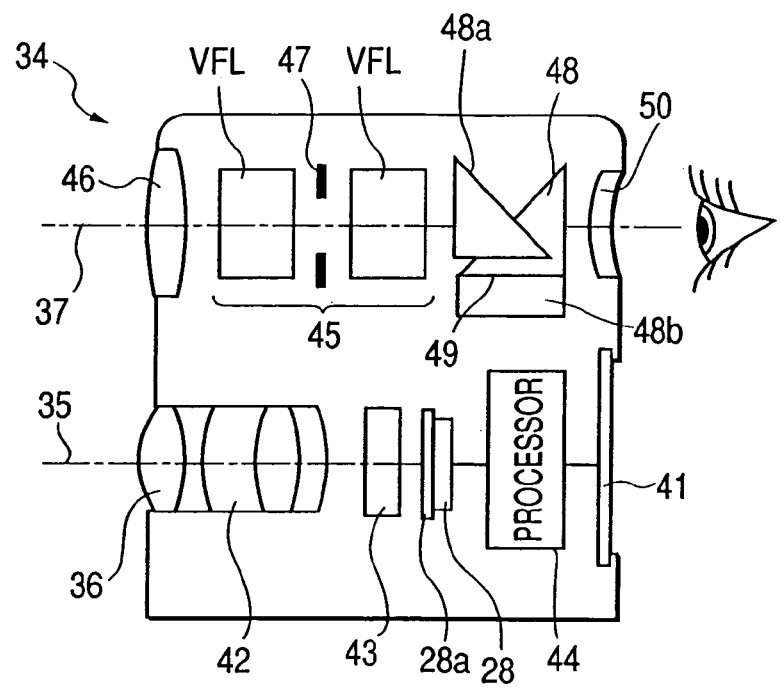
FIG. 30 is a sectional view schematically showing the interior arrangement of the electronic camera of FIG. 28.

In FIGS. 28-30, an electronic camera 34 includes a photographing optical system 36 having a photographing optical path 35, a finder optical system 38 having a finder optical path 37, a release 39, a flash lamp 40, and a liquid crystal display monitor 41. When the release 39 provided on the upper side of the camera 34 is pushed, photography is performed through a photographing objective optical system 42 in association with the operation of the release 39. An object image formed by the objective optical system 42 falls on an imaging surface 28a of a CCD 28 through a filter 43 such as a low-pass filter or an infrared cutoff filter. The object image received by the CCD 28 is displayed as an electronic image, through a processing means 44, on the liquid crystal display monitor 41 provided on the back side of the camera 34. The processing means 44 has a memory and is also capable of recording the electronic image photographed. Also, this memory may be provided to be independent of the processing means 44 or may be designed to electronically execute record/write with a floppy disk. The camera may be constructed as a silver halide film camera provided with a silver halide film instead of the CCD 28.

Moreover, on the finder optical path 37, an imaging optical system provided with the variable optical-property elements VFL is placed as a finder objective optical system 45. A cover lens 46 with positive power is provided as a cover member to enlarge an angle of view. The cover lens 46 and the variable optical-property element VFL situated on the object side of a stop 47 of the imaging optical system constitute the front lens unit of the finder objective optical system 45, while the variable optical-property element VFL situated on the image side of the stop 47 constitutes the rear lens unit thereof. The variable optical-property elements VFL are arranged respectively in the front and rear lens units, and voltages applied to their liquid crystals are controlled. In this way, zooming and focusing operations are performed. By the processing means 44, this voltage control is made in association with the zooming and focusing operations of the photographing objective optical system 42. An object image formed by the finder objective optical system 45 is placed on a field frame 49 of a Porro prism 48 which is an image erecting member. The field frame 49 separates a first reflecting surface 48a of the Porro prism 48 from a second reflecting surface 48b, and is interposed between them. An eyepiece optical system 50 which introduces an erect image into an observer's eye is placed behind the Porro prism 48. In the camera 34 designed as mentioned above, the finder objective optical system 45 can be constructed with a small number of optical members, and high performance and compactness are achieved.

Figure 31:
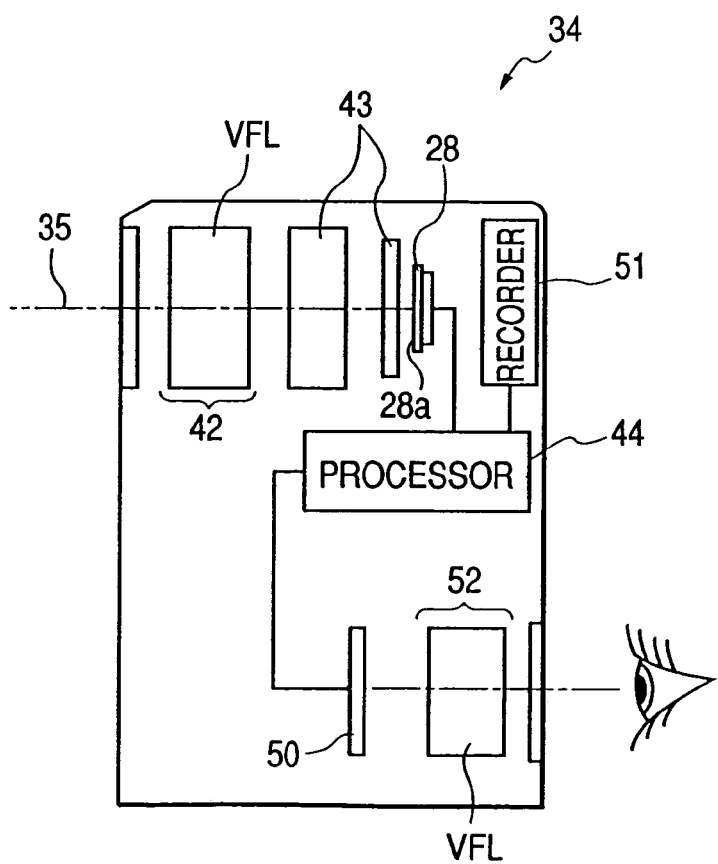
FIG. 31 is a schematic view showing an electronic camera in which the variable optical-property element of the present invention is incorporated in an objective optical system for photography.

In FIG. 31, the photographing objective optical system 42 situated on the photographing optical path 35 employs the variable optical-property element VFL. An object image formed by the photographing objective optical system 42 falls on the imaging surface 28a of the CCD 28 through the filters 43 such as a low-pass filer and an infrared cutoff filter. The object image received by the CCD 28 is displayed as an electronic image, through the processing means 44, on a liquid crystal display (LCD) 50. The processing means 44 also controls a recording means 51 which records the object image obtained by the CCD 28 as electronic information. The object image displayed on the LCD 50 is introduced through an eyepiece optical system 52 into the observer's eye. The eyepiece optical system 52 includes the variable optical-property element VFL which has the same characteristics as that used in the objective optical system 42. By controlling a voltage applied to the liquid crystal of the element VFL, the depth of a virtual image in the LCD 50 can be adjusted in accordance with the diopter of the observer. In the camera 34 designed as mentioned above, the finder objective optical system 45 can be constructed with a small number of optical members, and high performance and compactness are achieved.

Figure 32:
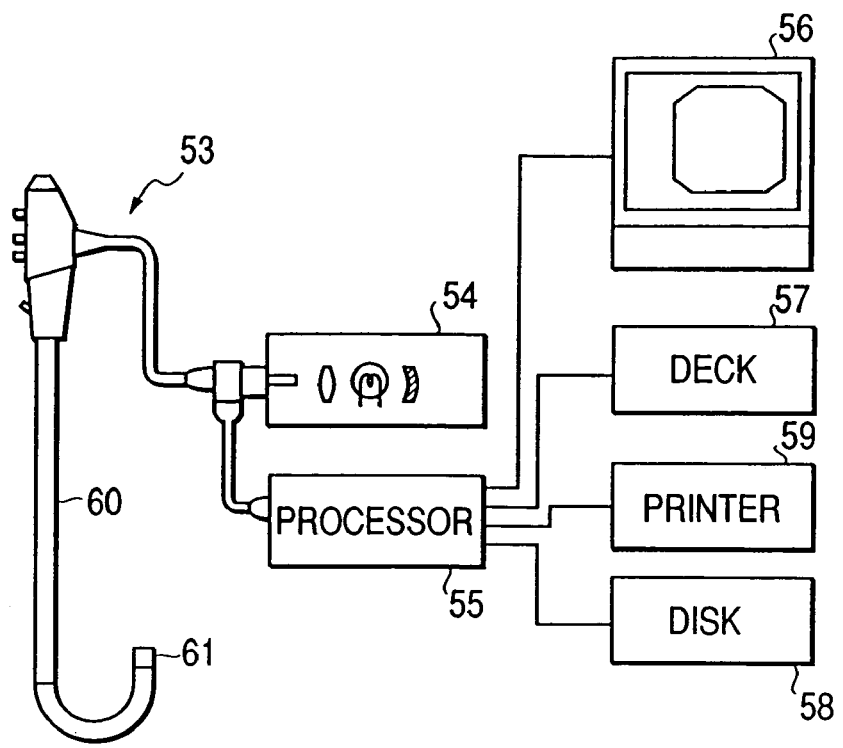
FIG. 32 is a view showing the entire system of an electronic endoscope apparatus in which the variable optical-property element of the present invention is incorporated in an objective optical system for observation.
Figure 33:
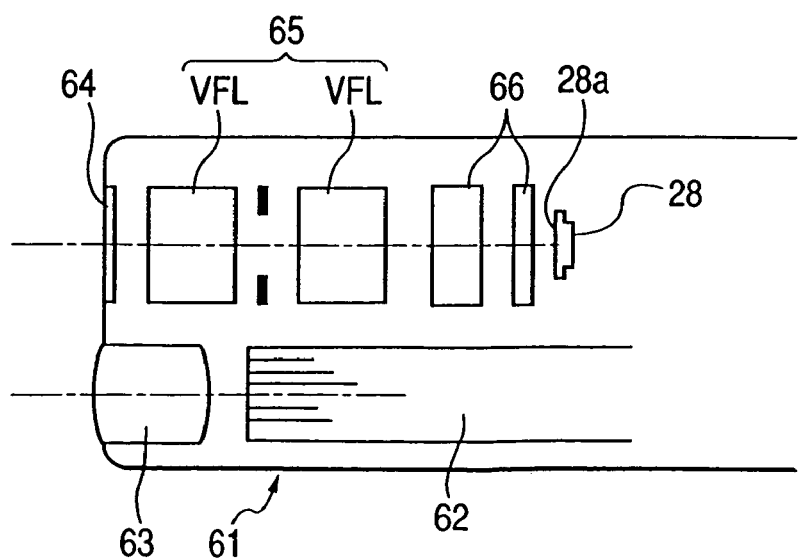
FIG. 33 is a view showing one interior arrangement of the distal end of the endoscope in FIG. 32.

In FIGS. 32 and 33, an objective optical system 65 of an observation system also uses the variable optical-property elements to perform the zooming and focusing operations. An electronic endoscope system, as shown in FIG. 32, includes an electronic endoscope 53; a light source device 54 for supplying illumination light; a video processor 55 for processing a signal with respect to the electronic endoscope 53; a monitor 56 for displaying an image signal output from the video processor 55; a VTR deck 57 and a video disk 58 for recording the image signal, each connected to the video processor 55; and a video printer 59 for printing out the image signal as an image. A distal end 61 of an inserting section 60 of the electronic endoscope 53 is constructed as shown in FIG. 33. An illumination light beam from the light source device 54 passes through a light guide fiber bundle 62 and illuminates a part to be observed, through an objective optical system 63 for illumination. Light from the part to be observed is such that an object image is formed through a cover member 64 by the objective optical system 65 for observation. The object image falls on the imaging surface 28a of the CCD 28 through filters 66 such as a low-pass filter and an infrared cutoff filter. Subsequently, the object image is converted into an image signal by the CCD 28. This image signal is displayed directly on the monitor 56 by the video processor 55 shown in FIG. 32, and is recorded in the VTR deck 57 and the video disk 58 and printed out as an image by the video printer 59. The endoscope designed in this way can be constructed with a small number of optical members, irrespective of the fact that zooming and focusing functions are retained, and is capable of achieving high performance and compactness.

Figure 34:
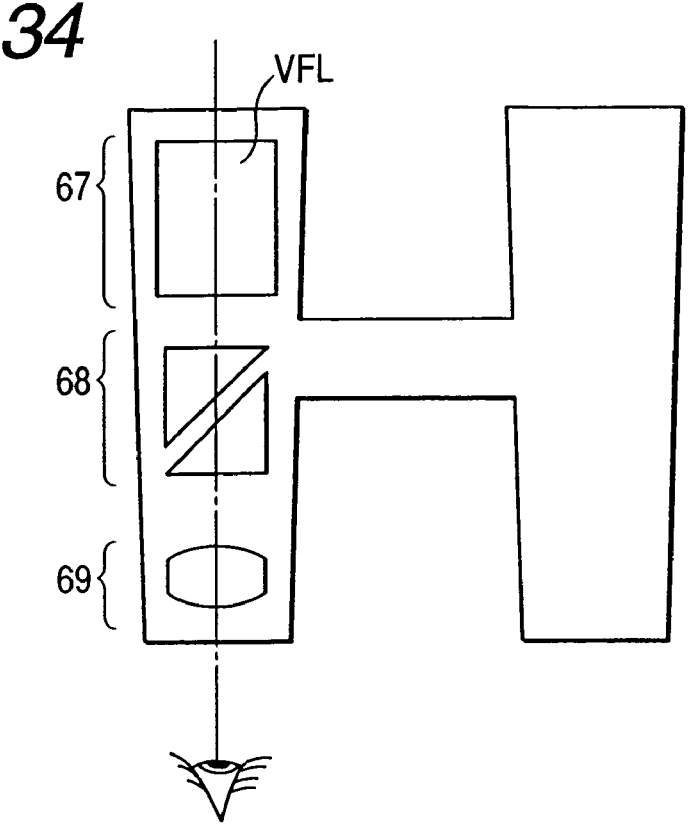
FIG. 34 is a schematic view showing binoculars using the variable optical-property elements of the present invention.

Even in the case of FIG. 34, showing the construction where the variable optical-property element of the present invention is incorporated in the optical system of binoculars, the variable optical-property element VFL is used in an objective optical system 67. A Pechan prism 68 is placed as an image erecting optical system behind the objective optical system 67, and an eyepiece optical system 69 for introducing an erect image into the observer's eye is located behind the Pechan prism 68. The objective optical system 67 includes the variable optical-property element VFL having the same characteristics as in the above embodiments, and by controlling the voltage applied to the liquid crystal, the focal length of the objective optical system 67 can be adjusted. In this way, the zooming and focusing operations are performed. Also, although, in this figure, only the structure of one side of the binoculars is shown, the same structure is provided on the other side. The binoculars designed in this way can be constructed with a small number of optical members, irrespective of the fact that zooming and focusing functions are retained, and is capable of achieving high performance and compactness.

Figure 35:
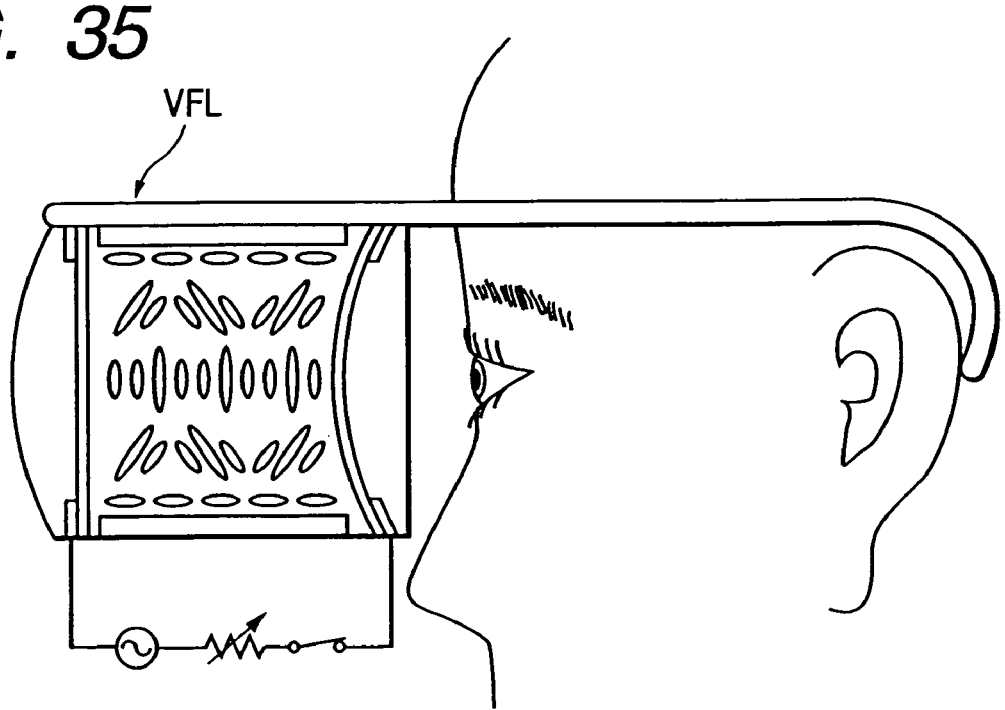
FIG. 35 is a schematic view showing spectacles in which the variable optical-property elements are incorporated in an optical system.

In FIG. 35, the variable optical-property elements VFL are used for the lenses of spectacles. In such spectacles, the voltages applied to the liquid crystals are controlled and thereby the diopter of the entire spectacles can be adjusted.

Figure 36:
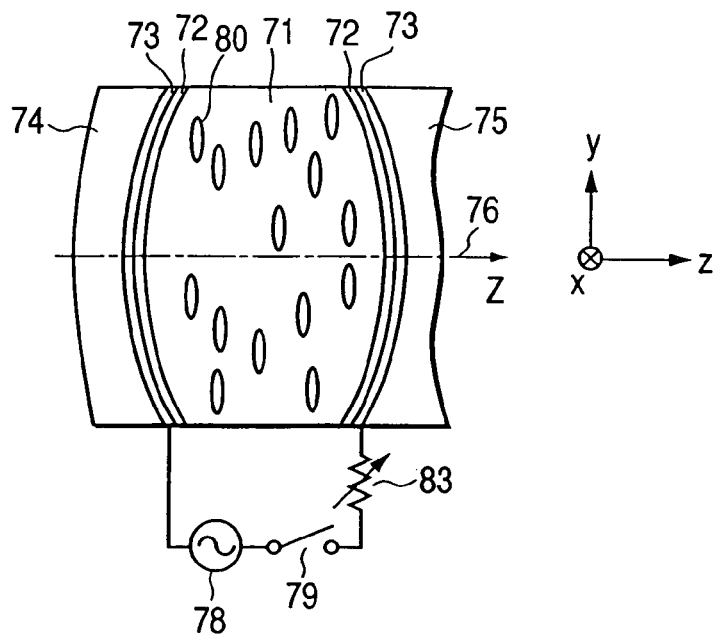
FIG. 36 is a view showing an optical system using a liquid crystal in which the anisotropy of refractive index is negative.

The variable focal-length lens used as the variable optical-property element of the present invention has a structure shown in FIG. 36, for instance. In this figure, reference numeral 71 represents a liquid crystal in which the anisotropy of refractive index is negative, 72 represents orientation films, and 73 represents transparent electrodes which are provided on transparent substrates 74 and 75, respectively.

Figure 37:
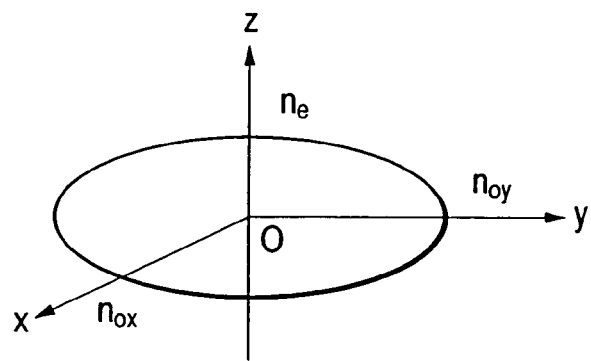
FIG. 37 is a view showing the index ellipsoid of the liquid crystal of FIG. 36.

In the optical element thus constructed, the liquid crystal 71 in which the anisotropy of refractive index is negative has the shape of an index ellipsoid such as that shown in FIG. 37, and satisfies the following conditions:

$$n_e < n_{ox}, \; n_e < n_{oy} \tag{64}$$

The liquid crystal 71 also satisfies the following condition:

$$n_{ox} = n_{oy} = n_0 \tag{65}$$

In such a variable focal-length optical element including the liquid crystal in which the anisotropy of refractive index is negative, the orientation films 72 are constructed so that when the voltage is not applied to the liquid crystal 71, the molecules of the liquid crystal 71 in the z direction are oriented in the direction of an optical axis 76, that is, in a Z direction. In this case, the refractive index of the liquid crystal relative to the incident light is $n_0$, and the optical element functions as a positive lens.

Figure 38:
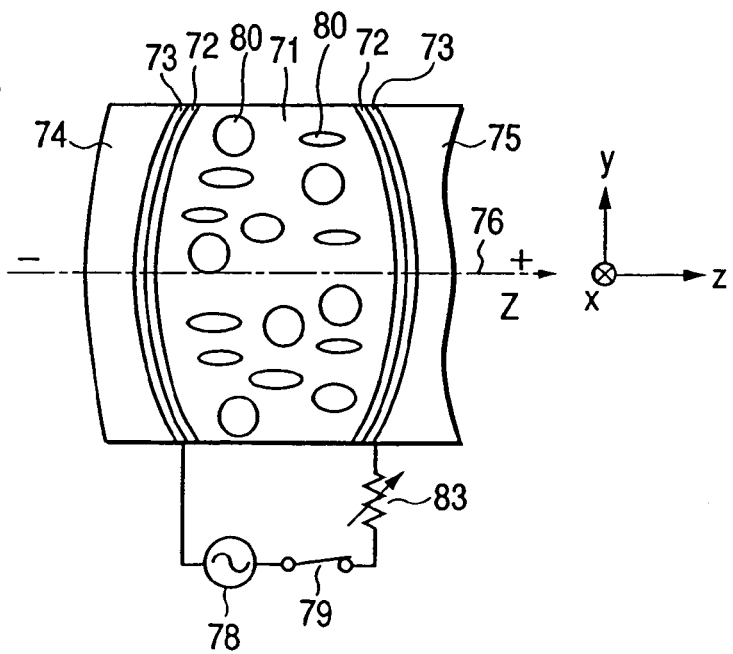
FIG. 38 is a view showing a state where an electric field is applied to the liquid crystal of FIG. 36.

In FIG. 36, when a switch 79 is turned on through an AC power supply 78, the orientation of liquid crystal molecules 80 is shifted as shown in FIG. 38 and thus the refractive index n relative to the incident light is lowered as expressed by the following equation:

$$n=(ne+n_0)/2 \tag{66}$$

Due to such a reduction of the refractive index, the optical element diminishes its refracting power as the positive lens to increase the focal length, and behaves as the variable focal-length lens. Moreover, the resistance of a variable resistor 83 is changed, and thereby the refractive index is continuously changed. Consequently, the focal length of the optical element can be continuously changed.

Figure 39:
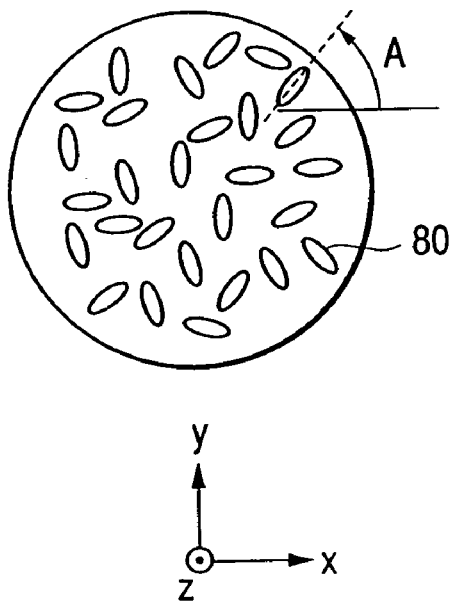
FIG. 39 is a view showing a state of the orientation of liquid crystal molecules.

The orientation films 72 are prepared so that the liquid crystal molecules 80 are oriented in a vertical direction, and as shown in FIG. 39, orientation angles A of the liquid crystal molecules 80 become random in an x-y plane. Therefore, even through any polarized light is incident on the optical element, the optical element acts as the variable focal-length which has the same focal length. Also, the liquid crystal 71 has an original nature that produces a homeotropic orientation such as that shown in FIG. 36, and thus the orientation films 72 need not necessarily be used. In order to change the orientation of the liquid crystal molecules 80, the frequency of the electric field, the magnetic field or the temperature, instead of the voltage, may be changed.

Figure 40:
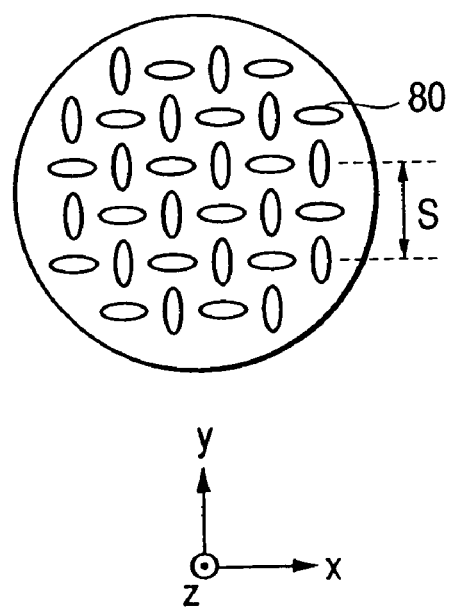
FIG. 40 is a view showing another state of the orientation of the liquid crystal molecules.

Even when the liquid crystal molecules 80, as shown in FIG. 40, are regularly oriented nearly perpendicular to one another, the same effect as in FIG. 39 is secured. In this case, it is desirable that a period S of the orientation of the liquid crystal molecules 80 is less than the wavelength $\lambda$ of light used, so as to satisfy the following condition:

$$0.5 \text{ nm}<S<\lambda \tag{67}$$

This is because the scattering of light is minimized and flare is reduced.

Here, the wavelength $\lambda$ is in the range of 350-700 nm for visible light. That is, in the case of the visible light, the condition of the period S is as follows:

$$0.5 \text{ nm}<S<700 \text{ nm}$$

In the case of near-infrared light, the wavelength $\lambda$ is in the range of 650-1200 nm, and thus Condition (67) can be expressed as follows:

$$0.5 \text{ nm}<S<1200 \text{ nm}$$

Figure 41:
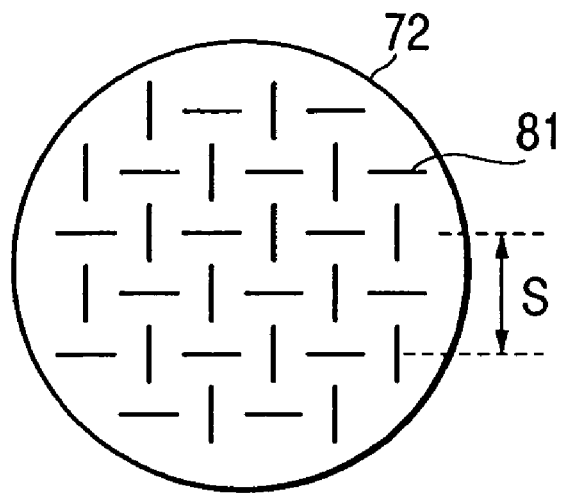
FIG. 41 is a view showing a pattern formed on an orientation film.

In order to orient the liquid crystal molecules 80 as shown in FIG. 40, it is only necessary, as shown in FIG. 41, to regularly provide each of the orientation films 72 with fine grooves 81 of the pitch S. The grooves 81 have depths ranging from 0.1 nm to several tens of nanometers and can be made by photoresist exposure and etching as set forth, for example, in Kikuta and Iwata, "Light control by grating structure smaller than wavelength", Optics, Vol. 27, No. 1, pp. 12-17, 1998. A model in which the grooves are formed by etching may be made and used to transfer the grooves to plastic.

Figure 42:
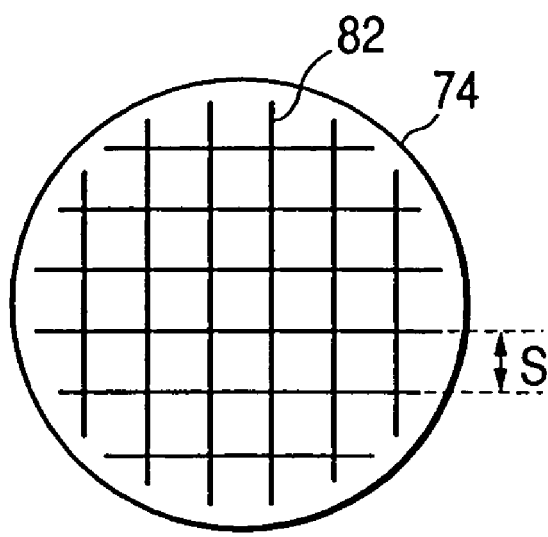
FIG. 42 is a view showing another pattern formed on the orientation film.

Instead of a pattern shown in FIG. 41, a convexity or concavity 82 of a grating pattern such as that shown in FIG. 42 may be used if the orientation of the liquid crystal molecules 80 is uniform, looking at in the x-y plane, that is, unless the refractive index of the liquid crystal 71 varies with the orientation. This grating pattern may be formed not on the surfaces of the orientation films 72, but on the surface of the transparent substrates 74 or 75. In this instance, the orientation films 72 can be dispensed with, as the case may be. The fine grooves 81 may be configured not as depressions but as projections. The optical element may also be designed so that the liquid crystal in which the anisotropy of refractive index is negative is used, and so that, as in FIG. 38, the voltage is applied and the liquid crystal has the periodical structure of the pitch P, for example, the helical structure. In this case, the liquid crystal satisfies at least one of Conditions (26), (28)-(31), (38), and (39), and (69)-(77) which will be described later. In this case, the orientation films 72 may be eliminated.

As mentioned above, a liquid crystal lens in which the orientation of the liquid crystal molecules 80 is uniformed in the x-y plane to be independent of polarization and to bring about a sharp focus can be used as the variable optical-property element having the same structure as in FIG. 36 not only when the anisotropy of refractive index of the liquid crystal is negative, but also when a positive nematic liquid crystal is used to satisfy the following condition:

$$ne>n_0 \tag{68}$$

Substances having electrooptical effects and magnetrooptical effects of macromolecular dispersed liquid crystals, chiral smectic liquid crystals, chiral cholesteric liquid crystals, ferroelectric liquid crystals, antiferroelectric liquid crystals, and ferroelectrics are also applicable to the present invention. Besides the above embodiment, these respective substances are applicable to embodiments which will be described later.

Figure 43:
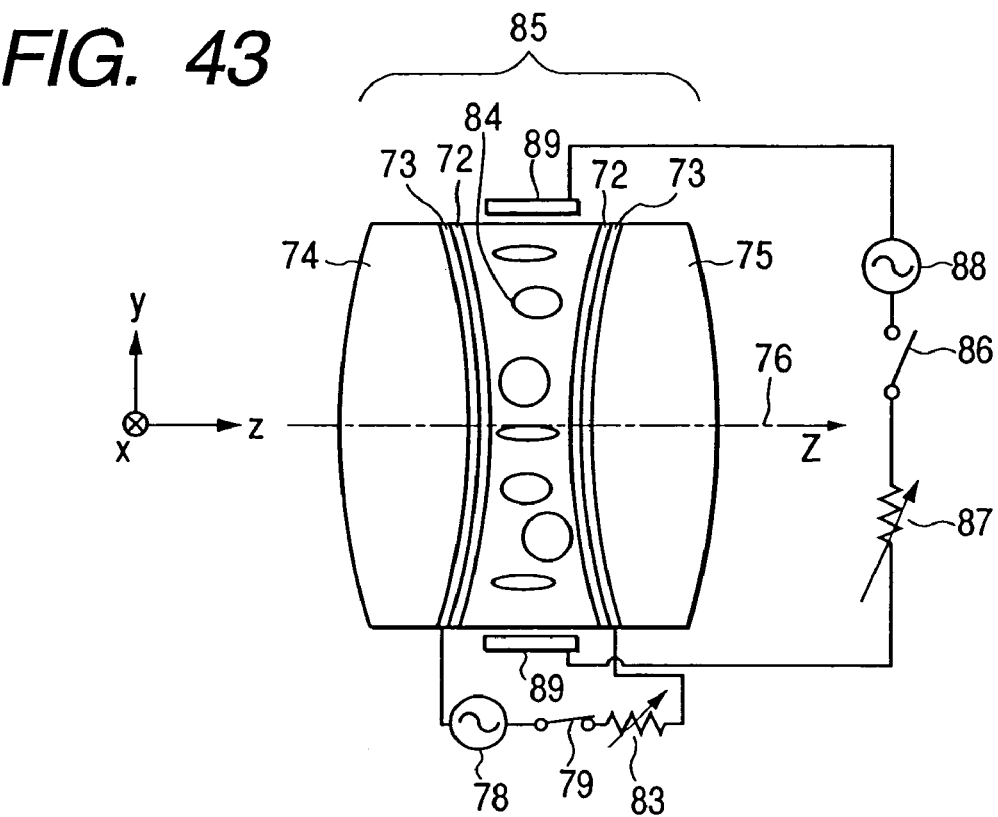
FIG. 43 is a view showing a liquid crystal lens in which the orientation of the molecules of a liquid crystal is changed with a high speed.

FIG. 43 illustrates a liquid crystal lens in which the electric field is applied in the direction of the optical axis and a direction perpendicular thereto, and thereby the orientation of the molecules of a liquid crystal 84 is shifted with high speed. The liquid crystal 84 in this figure, like that shown in FIG. 36, is constructed so that the anisotropy of refractive index is negative. This embodiment shows an variable optical-property element (variable focal-length lens) provided with members for applying one electric field, composed of the electrodes 73, the AC power supply 78 connected thereto, the switch 79, and the variable resistor 83, such as those shown in FIG. 36, and members for applying another electric field, composed of electrodes 89 placed opposite to each other, sandwiching the optical axis 76 between them, an AC power supply 88 connected thereto, a switch 86, and a variable resistor 87. In this variable focal-length lens, that is, a liquid crystal lens 85, FIG. 43 is in a state where the switch 79 is turned on and the switch 86 is off.

Figure 44:
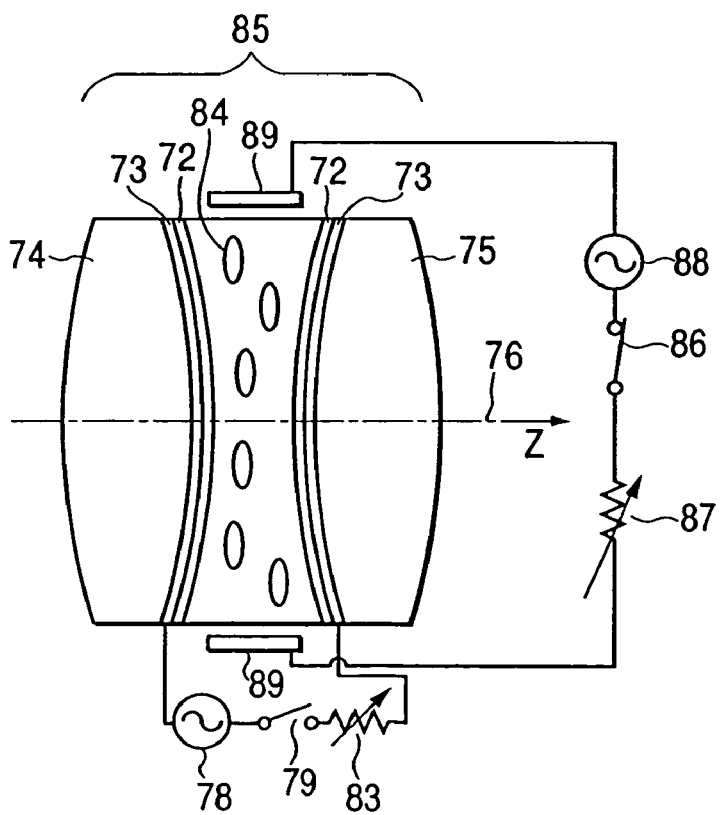
FIG. 44 is a view showing a state where an electric field is applied to the liquid crystal of FIG. 43.

In order to change the focal length of the liquid crystal lens 85, as shown in FIG. 44, the switch 79 is turned off and at almost the same time, the switch 86 is turned on. In this way, the electric field is applied through the electrodes 89 to the liquid crystal 84, and the molecules of the liquid crystal 84 change their z direction to be parallel to the optical axis. Hence, the refractive index of the liquid crystal lens is increased and the function as a negative lens is improved, thereby changing the focal length.

Figure 45:
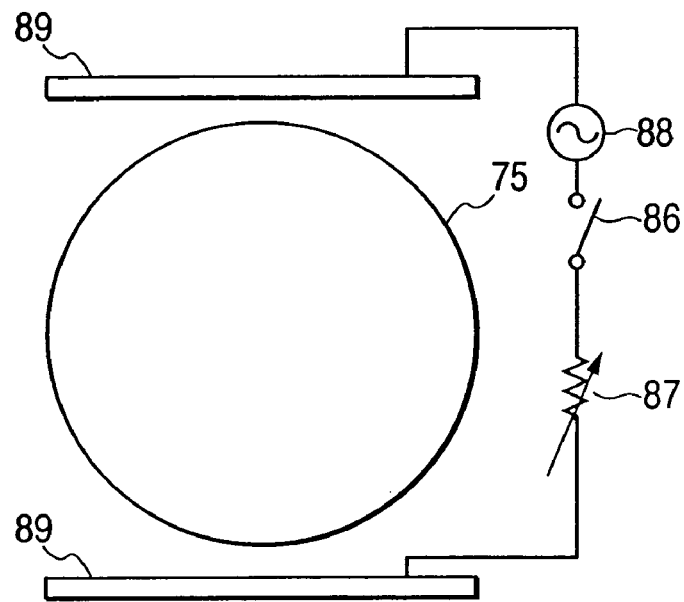
FIG. 45 is a view showing the liquid crystal lens looking at along the direction of a z axis in FIG. 43.

FIG. 45 shows the positions and shapes of the electrodes 89, looking at the liquid crystal lens 85 from a +Z direction.

Figure 46A:
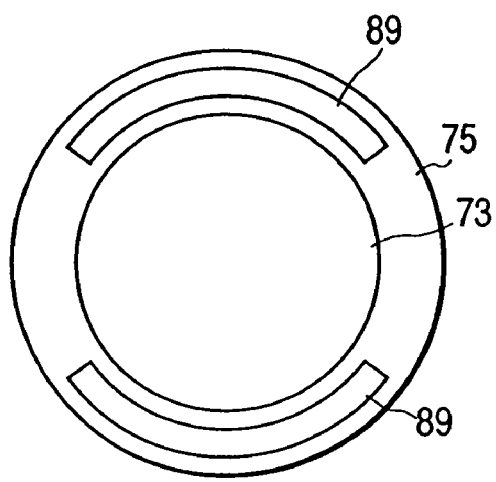
FIGS. 46A and 46B are views showing a modification example of the liquid crystal lens of FIG. 43, looking at along the directions of z and x axes, respectively.
Figure 46B:
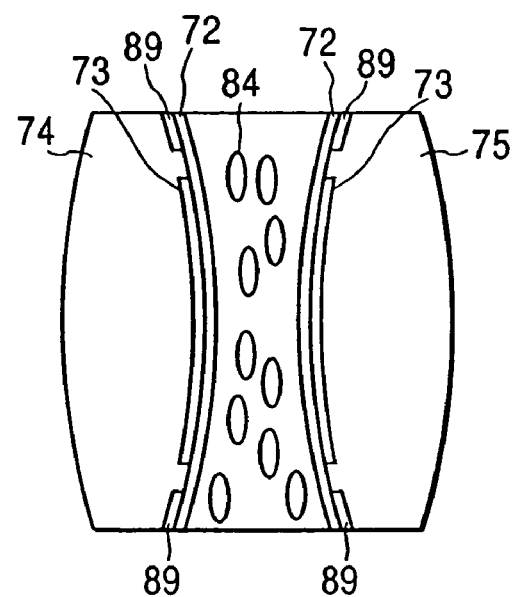

FIGS. 46A and 46B show a modification example of the liquid crystal lens of FIG. 43, from which the electrodes 89 are different in position and shape. The electrodes 89, as shown in FIG. 46A, are provided in a state of insulation from the transparent electrode 73 on the periphery of at least one of the transparent substrates 74 and 75 shown in FIG. 46B, and bring about almost the same effect as those shown in FIG. 45.

The liquid crystal lens 85 depicted in FIG. 43 has the feature that where the z axis of each of the liquid crystal molecules 84 is made parallel to the optical axis 76, a response speed is faster than in the liquid crystal lens shown in FIG. 38. Whether the focal length of the liquid crystal lens 85 is long or short, the electric field is applied to the liquid crystal molecules 84, and thus the liquid crystal lens 85 excels in minimizing the variation of the orientation of the liquid crystal molecules and the scattering of light.

In addition, the variable resistors 83 and 87 are properly adjusted, and thereby the focal length of the liquid crystal lens 85 can be continuously changed. The orientation of the liquid crystal molecules 84 lies in a state of a compromise between FIG. 43 in which the switch 79 is on and the switch 86 is off and FIG. 44 in which the switch 79 is off and the switch 86 is on.

In the disclosure so far, reference has been made to a liquid crystal that a dielectric anisotropy relative to the driving AC frequency of the liquid crystal molecules 80 or 84 is also negative as in the anisotropy of refractive index. As an example of such a liquid crystal, a discotic liquid crystal is cited.

Figure 47:
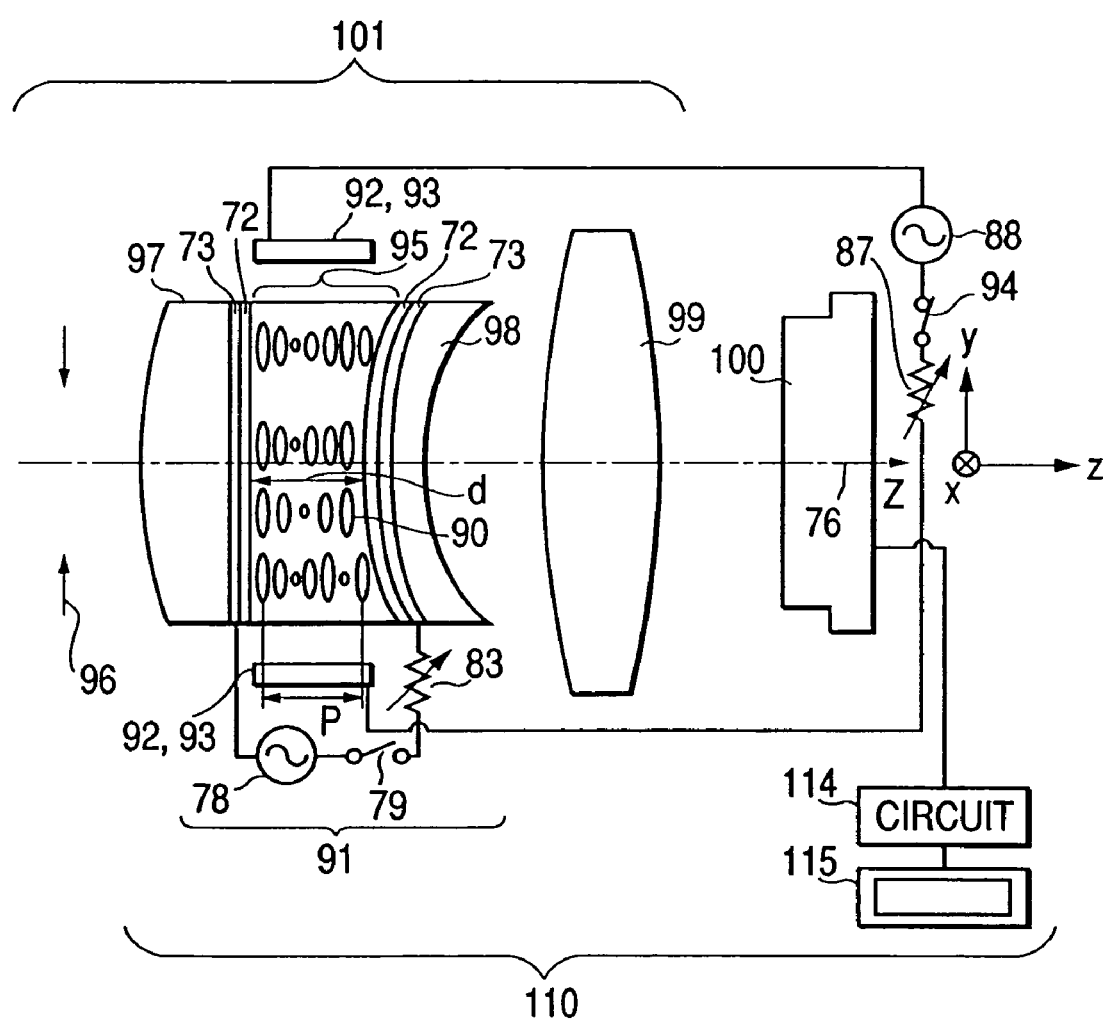
FIG. 47 is a view showing an imaging device using the liquid crystal lens of the present invention.

In the embodiment shown in FIG. 47, a variable focal-length lens 91, instead of the liquid crystal molecules 84 shown in FIG. 43, uses a nematic liquid crystal 90 having a positive anisotropy of refractive index and a dielectric anisotropy. Thus, Condition (68) is established.

In FIG. 47, an imaging device for digital cameras using the variable focal-length lens 91 is shown. The molecules of the liquid crystal 90 are helically oriented at the pitch P. The variable focal-length lens 91 is such that the direction of one molecule of the liquid crystal 90 is nearly parallel to the x-y plane. If the value of the pitch P of the liquid crystal molecules is less than 20-60 times the wavelength $\lambda$ of light used in the variable focal-length lens 91, the liquid crystal 90 can be practically thought of as an isotropic medium.

Now, it is assumed that the pitch P is smaller than the wavelength $\lambda$, that is, satisfies the following condition:

$$P<\lambda \tag{69}$$

In this case, the liquid crystal approaches the isotropic medium. The explanation of the reason for this is the same as that relative to Conditions and Equations (1)-(20) in the case where FIG. 5 is replaced by FIG. 47.

Since $P/\lambda<<1$, the variable focal-length lens 91 shown in FIG. 47 functions as a lens with the refractive index n' and produces an image with no blurring.

Figure 49:
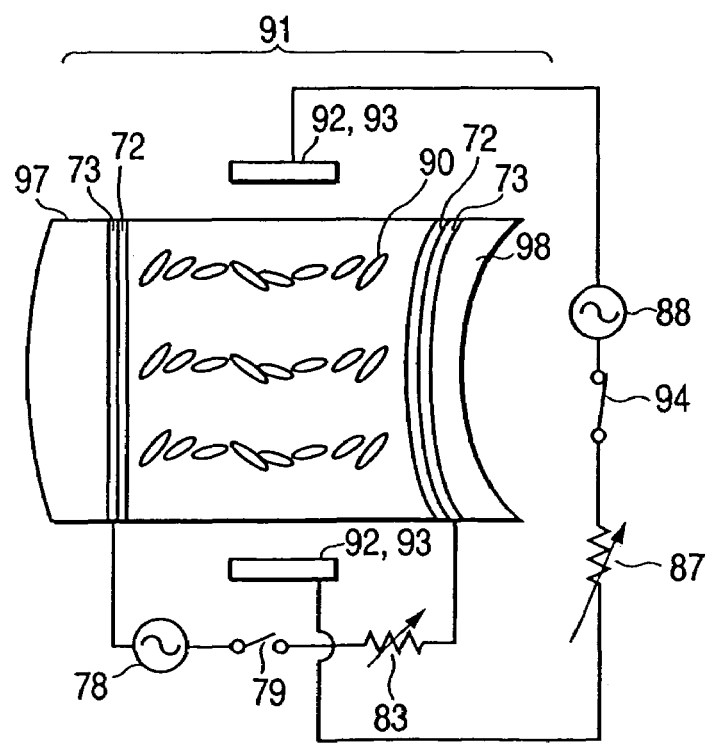
FIG. 49 is a view showing a variable focal-length optical system using the variable optical-property element of the present invention.

Even where the liquid crystal has a compromise orientation of molecules as shown in FIG. 49, the value of the refractive index ne is replaced by a refractive index ne' of extraordinary light which is an intermediate value between the refractive indices ne and $n_0$, and thereby it is possible to satisfy Conditions and Equations (3)-(20).

By constructing the liquid crystal lens as shown in FIG. 47, not only is the voltage applied continuously and variably, but also the voltage to be applied can be selected from among some discrete voltage values. In this case also, the variable focal-length lens is obtained.

For an actual example of the variable focal-length lens constructed as in FIG. 47, its detailed explanation is the same as that relative to Equations and Conditions (21)-(33).

Subsequently, design examples are shown below.

First Design Example
 d=15µ
 $\lambda$=0.5µ
 ne−$n_0$=0.2
 P=0.06µ then $\Gamma/2\Phi=(1/2)\cdot 0.2\times 0.06/0.5=0.012$

This satisfies Conditions (20) and (28)-(30).

Second Design Example
 d=50µ
 $\lambda$=0.6µ
 ne−$n_0$=0.25
 P=0.5µ then $\Gamma/2\Phi=(1/2)\cdot 0.5\times 0.25/0.6=0.1042$

This satisfies Conditions (26) and (28)-(30).

Third Design Example
 d=100µ
 $\lambda$=0.55µ
 ne−$n_0$=0.2
 P=3µ then $\Gamma/2\Phi=(1/2)\cdot 0.2\times 3/0.55=0.5454$

This satisfies Conditions (28) and (30).

Fourth Design Example
 d=200µ
 $\lambda$=0.95µ
 ne−$n_0$=0.2
 P=7µ then $\Gamma/2\Phi=(1/2)\cdot 0.2\times 7/0.95=0.737$

This satisfies Conditions (28) and (30).

In each of the design examples mentioned above, the chiral nematic liquid crystal is used as an example. In order to make the pitch of twist of the nematic liquid crystal smaller than the wavelength of light used, it is good practice to mix the chiral dopant with the liquid crystal.

As the chiral dopants, cholesteric liquid crystals or optically active, synthetic compounds are used. The examples of the nematic liquid crystals and the chiral dopants are as shown in chemical formulas (a)-(d) already mentioned.

In Condition (30), when an example of a typical liquid crystal is considered as ne−$n_0$=0.1 it follows that $(1/2)\times 0.1(P/\lambda)<\pi$

From this result, the following condition is obtained:

$$P<20\pi\cdot\lambda\approx 62.8\lambda \tag{0.70}$$

Similarly, substitution of ne−$n_0$=0.1 in Condition (28) gives $$P<20\lambda \tag{71}$$

Hence, if a liquid crystal is constructed to satisfy Condition (70) or (71) in accordance with a product using the liquid crystal, the variable optical-property element, such as the variable focal-length lens, with little blurring (flare) will be obtained. Conditions and Equations (1)-(30) hold for all the liquid crystals having the helical structures with the pitch P as well as for the nematic liquid crystals. As the examples of such liquid crystals, cholesteric liquid crystals, smectic liquid crystals, ferroelectric liquid crystals, and antiferroelectric liquid crystals are cited.

In order to improve the performance of the optical system, it is desirable that the value of the pitch P is small. However, when the value of the pitch P in the liquid crystal generally becomes small, the viscosity of the liquid crystal is increased and the response speed of a change of the refractive index caused by a variation of the electric field becomes slow. In view of this respect, experiments show that it is favorable that the value of the pitch P is practically larger than the wavelength λ. Moreover, in view of Conditions (28)-(30), (70), and (71), it is desirable to satisfy one of the following conditions:

$$\lambda \leq P < 20\lambda \tag{72}$$

$$\lambda \leq P \text{ and } |\Gamma/2\Phi| < \pi \tag{73}$$

In optical systems such as those used in autofocus TV cameras, a faster response speed is required. Thus, for such optical systems, it is desirable to satisfy one of the following conditions:

$$2\lambda \leq P < 20\lambda \tag{74}$$

$$2\lambda \leq P \text{ and } |\Gamma/2\Phi| < \pi \tag{75}$$

Conversely, for optical systems in which a very quick response speed is not required, for example, spectacles and diopter adjusters, it is only necessary to satisfy one of the following conditions:

$$(2/3)\lambda \leq P < 20\lambda \tag{76}$$

$$(2/3)\lambda \leq P \text{ and } |\Gamma/2\Phi| < \pi \tag{77}$$

The upper limit of the value of the pitch P in each of Conditions (72), (74), and (76) is allowable up to 60λ for an inexpensive optical system which does not require high optical, performance, for example, the finder of a camera.

Also, in a chiral nematic liquid crystal with a thickness of 9μ and a pitch of 1.1μ, a response time accommodating a change of an AC electric field is about 1-30 seconds.

In the disclosure so far, the symbol P has denoted the pitch of the liquid crystal having the helical structure. However, the conditions relative to the above-mentioned pitch P also hold for the following substances:

(A) Liquid crystals or variable refractive-index substances in which the refractive index is periodically changed at the period P in one direction.

(B) Variable refractive-index substances in which when refractive indices are averaged at the length P, the values of the refractive indices become nearly constant, although not completely periodically in one direction. They are called variable refractive-index substances with pseudo-periods P.

As the examples of item (A), ferroelectric liquid crystals such as barium titanate are cited, and as item (B), macromolecular dispersed liquid crystals and macromolecular stabilized liquid crystals in which an average diameter of liquid crystal particles is less than the length P are cited.

Also, it is further desirable that the variable refractive-index substance stated in item (A) satisfies at least one of Conditions (26), (28)-(30), and (69)-(77).

Figure 48:
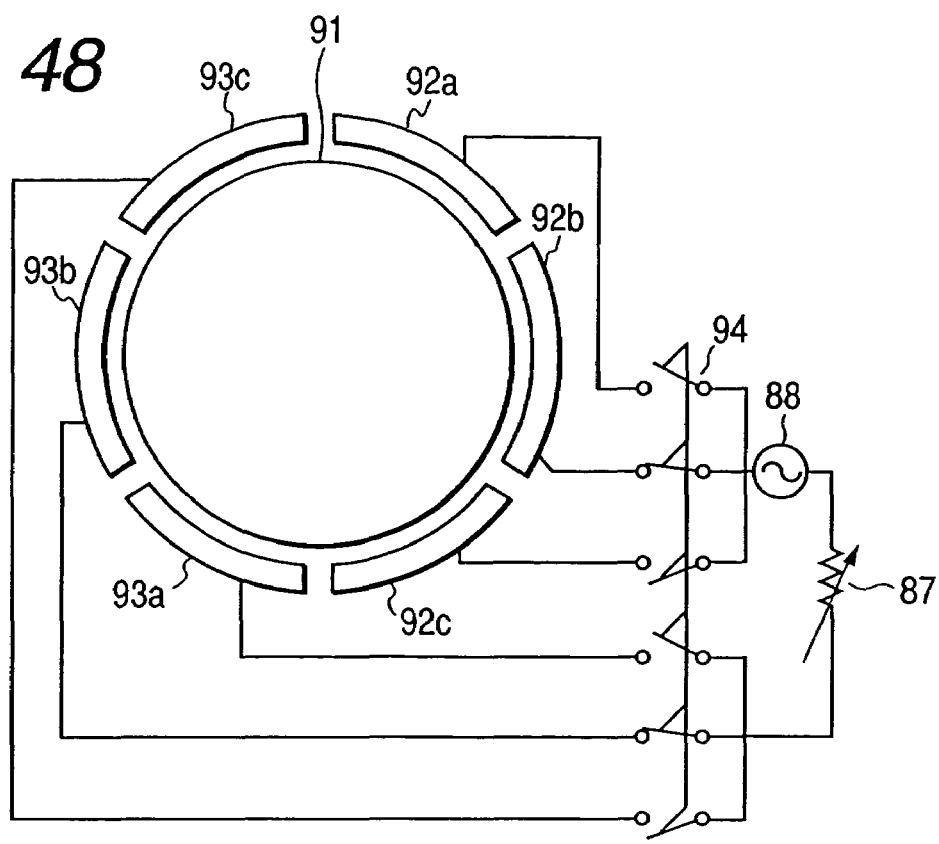
FIG. 48 is a view showing the liquid crystal lens looking at along the direction of the z axis in FIG. 47.

FIG. 48 shows the variable focal-length lens 91 used in the imaging device shown in FIG. 47, looking at from the Z direction. Electrodes 92a, 92b, 92c, 93a, 93b, and 93c divided into six pieces are placed close to the periphery of the variable focal-length lens 91 and are insulated from the transparent electrodes 73. These pairs of electrodes 92a and 93a; 92b and 93b; and 92c and 93c are such that AC voltages are applied in succession by a triple switch 94. In this way, the direction of the electric field is changed and thereby the orientation of the liquid crystal molecules becomes nearly isotropic. If the electric field is applied in only one direction, the helical structure of the liquid crystal molecules may be disrupted.

Subsequently, a description is given of the operation of the imaging device shown in FIGS. 47 and 48. When the switch 79 is turned on, the triple switch 94 is kept to an off state. Thus, the major axes of the molecules of the liquid crystal 90 become nearly parallel to the optical axis. In this case, a liquid crystal lens portion 95 becomes a negative lens with weak power.

Then, when the switch 79 is turned off and at the same time, the triple switch 94 is turned on, the electric field is applied in a lateral direction to the liquid crystal 90, and thus the orientation of the molecules of the liquid crystal 90 is shifted with high speed as shown in FIG. 47.

For a period T for switching voltages applied to three electrodes of the triple switch 94, there is the need to satisfy the following relationship. In the optical system shown in FIG. 47, when the triple switch 94 is in an off state and the switch 79 is in an on state and after some time, is turned off, the molecules of the liquid crystal 90 are naturally oriented as shown in FIG. 47 because of the orientational regulating force of the orientation films 72, even though the triple switch 94 is not turned on. Thus, when a time required to naturally orient the molecules as shown in FIG. 47 is represented by τ, it is necessary to have the following relation:

$$T \leq \tau \tag{78}$$

If the period T is so large as not to satisfy Condition (78), there is the fear that the helical structure of the molecules of the liquid crystal 90 may be disrupted and the orientation of the molecules of the liquid crystal 90 may be shifted to a homogeneous orientation parallel to the orientation films 72.

For Condition (78), it is only necessary to satisfy the following condition in practical use:

$$T \leq 10\tau \tag{79}$$

If this condition is not satisfied, much time may be required until the molecules of the liquid crystal 90 have a completely helical orientation when voltages applied to the electrodes 92 and 93 are low.

After the orientation of the molecules of the liquid crystal 90 has been returned to a state shown in FIG. 47, the triple switch 94 may be turned off discontinuously. In other words, the triple switch 94 may be kept to an on state only while the orientation of the molecules of the liquid crystal 90 changes from a homeotropic orientation in a state parallel with the optical axis 76 to the helical orientation shown in FIG. 47 caused even when the switch 79 is turned off. Consequently, an electric power can be saved, which is advantageous.

As shown in FIG. 49, the variable resistors 83 and 87 are properly adjusted so that the molecules of the liquid crystal 90 are oriented to be oblique with respect to the optical axis, and thereby the focal length of the variable focal-length lens 91 can be continuously changed. That is, this lens is convenient for use in a zoom lens system.

Figure 50:
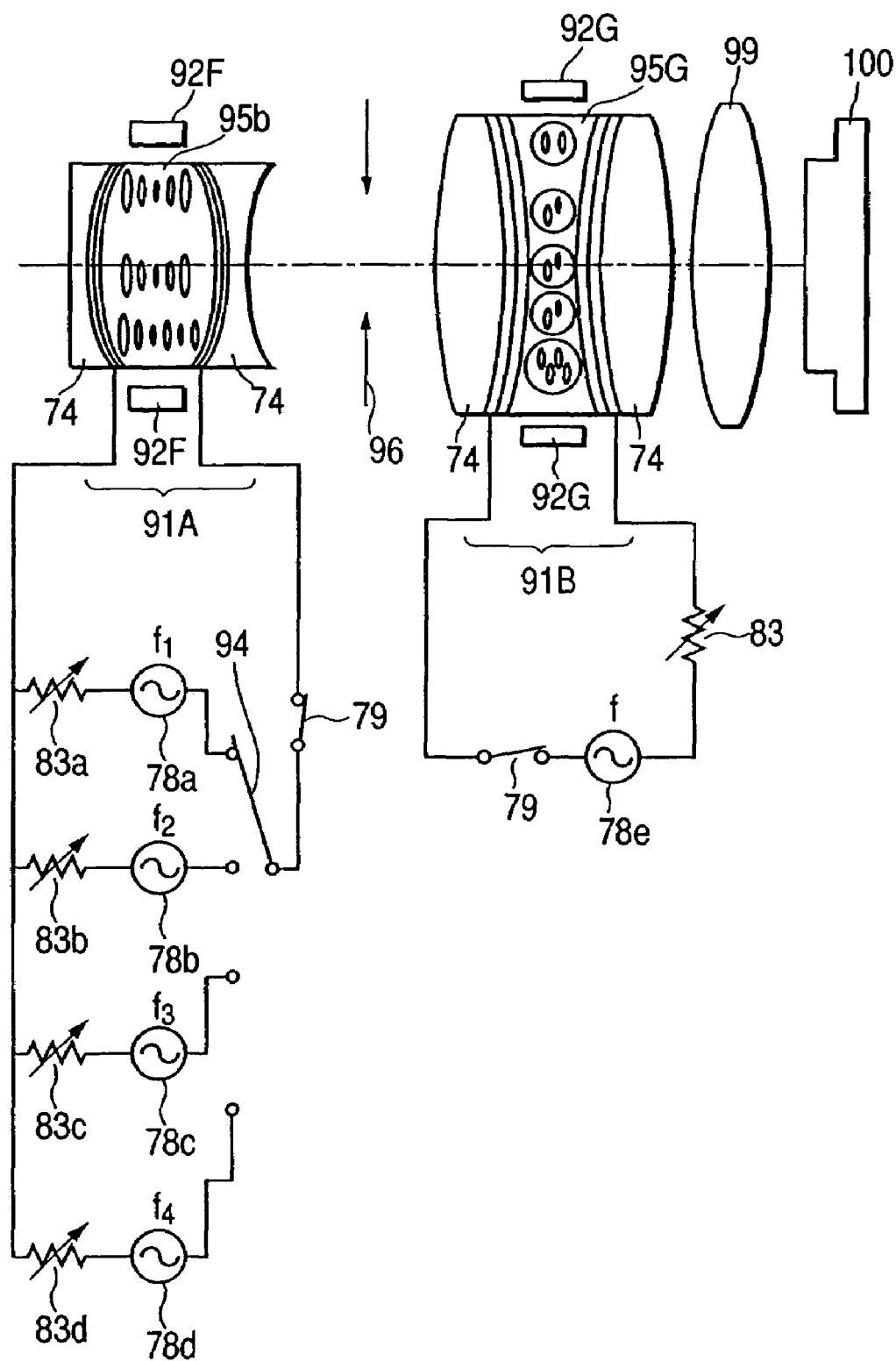
FIG. 50 is a view showing an imaging device provided with zoom lenses using the liquid crystal lenses of the present invention.

FIG. 50 shows an embodiment in which the variable focal-length lens shown in FIG. 47 or 49 is used in a zoom lens system. In this figure, each of reference numerals 91A and 91B corresponds to the variable focal-length lens 91 shown in FIG. 47. The variable focal-length lenses 91A and 91B are front and rear lens units respectively arranged before and behind a stop 96. That is, this zoom lens system includes the front lens unit with negative refracting power, composed of the variable focal-length lens 91A having a negative function and the rear lens unit with positive refracting power, as a whole, composed of the stop 96, the variable focal-length lens 91B having a positive function, and a positive lens 99. By changing the focal lengths of the variable focal-length lenses 91A and 91B without mechanically moving individual lenses, the focal length of the entire lens system and the movement of an image plane can be corrected. Likewise, the focusing operation can be performed. In this embodiment, when the variable focal-length lens 91A is energized to change the focal length, the strength of the electric field applied to a liquid crystal 95b is not changed, but the frequency of the electric field is changed to four stages of $f_1$, $f_2$, $f_3$, and $f_4$. In this way, a liquid crystal in which the sign of the dielectric anisotropy changes with the frequency is used. When the frequencies $f_1$, $f_2$, $f_3$, and $f_4$ are determined as $f_1 < f_2 < f_3 < f_4$, the dielectric anisotropies of the liquid crystal 95b are so chosen as to have signs opposite to each other at the frequencies $f_1$ and $f_4$.

In this zoom lens system, the frequency is changed by turning the switch 94. In this case, electrodes 92F may be eliminated. The frequencies $f_1$, $f_2$, $f_3$, and $f_4$, instead of being changed gradually, may be changed continuously. Moreover, when the frequency is changed, the strength of the electric field may also be changed at the same time.

Each of the liquid crystal lenses 91A and 91B may use not only the helical liquid crystal, but also the macromolecular dispersed liquid crystal in which a liquid crystal that the dielectric anisotropy varies with the frequency is dispersed among macromolecules. The variable focal-length lens 91B is an example of the variable optical-property element using the macromolecular dispersed liquid crystal.

An AC power supply 78e capable of continuously changing the frequency is connected to the two electrodes 73. The frequency of the AC power supply is varied and thereby the focal length of the optical element can be changed.

By associating the liquid crystal lens 91A with the liquid crystal lens 91B, the zooming operation can be performed. In addition, if only the liquid crystal lens 91B is energized, the focusing operation can be performed.

Electrodes 92G need not necessarily be used, or voltages applied to the electrodes 92G may be changed in association with a change of a frequency f of the AC power supply 78e.

In the imaging device shown in FIG. 47, the liquid crystal lens, instead of using the liquid crystal 90, may use the chiral cholesteric liquid crystal, chiral smectic liquid crystal, ferroelectric liquid crystal, antiferroelectric liquid crystal, liquid crystal with the negative anisotropy of refractive index, ferroelectric macromolecular dispersed liquid crystal, etc. Conditions (26), (28)-(30), and (69)-(79) also hold for the case where each of these liquid crystals is used.

Figure 51:
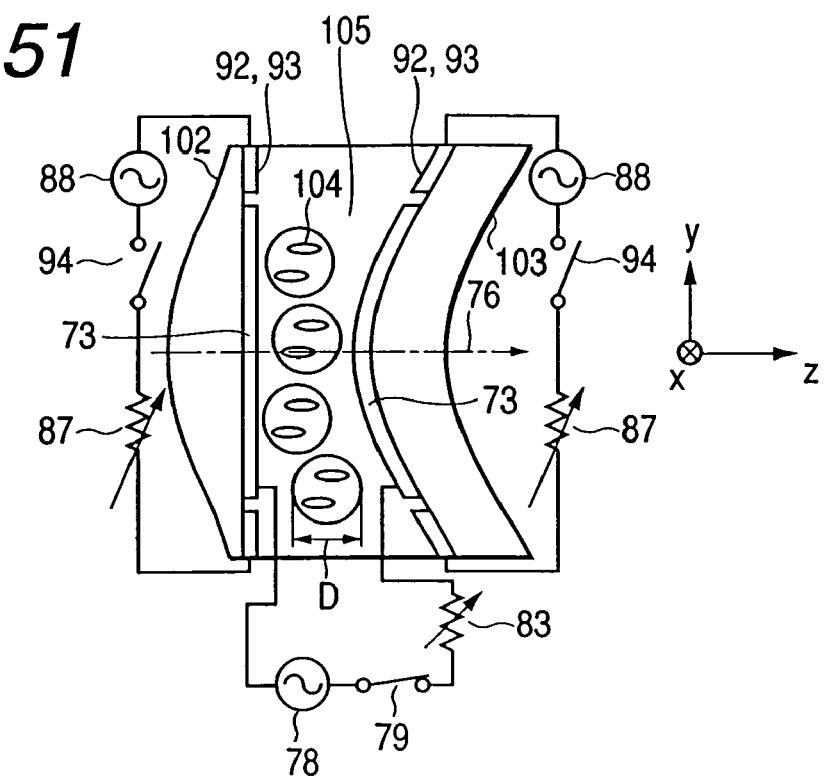
FIG. 51 is a view showing a liquid crystal lens using a polymer.

An optical system shown in FIG. 51 is such that, instead of the liquid crystal 90 of FIG. 47, cells with the average diameter D including nematic liquid crystal molecules 104 are arranged granularly in a polymer. In this embodiment, the divided electrodes 92 and 93 are actuated as in FIG. 47, but are arranged on the peripheries of lenses 102 and 103 so that they are insulated from the transparent electrodes 73. The operation of the triple switch 94 is the same as in the optical system of FIG. 47.

Figure 52:
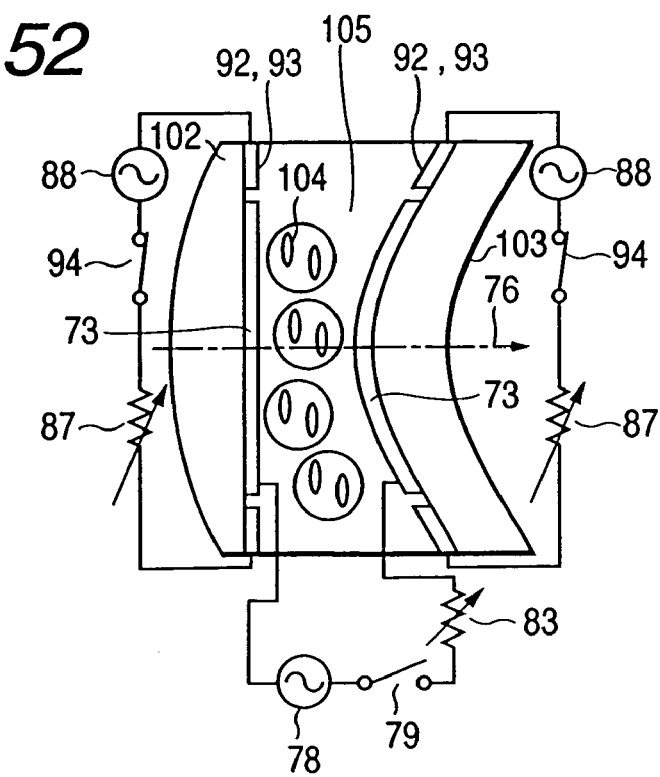
FIG. 52 is a view showing a state where an electric field is applied to the liquid crystal of FIG. 51.

In the optical system shown in FIG. 51, when the switch 79 is in an on state, the liquid crystal molecules 104 hold an homeotropic orientation, while when the switch 79 is turned off and the triple switch 94 is on, the electric field is applied to the liquid crystal molecules 104 in a lateral direction, and the liquid crystal molecules 104, although somewhat random, are oriented parallel to the x-y plane with high speed as shown in FIG. 52. Conditions (78) and (79) also hold for the optical system shown in FIGS. 51 and 52.

As mentioned above, the liquid crystal molecules 104, as in FIG. 52, are oriented nearly perpendicular to the optical axis, and thus this liquid crystal lens excels in bringing about a greater change of the refractive index of a liquid crystal 105.

Here, if the average diameter D of the liquid crystal molecules 104 satisfies the following condition, the scattering of light can be prevented, which is favorable:

$$D < \lambda/5 \qquad (80)$$

Where the thickness of the liquid crystal 105 is relatively small, there is no problem in practical use if the diameter satisfies the following condition, instead of Condition (80):

$$D < 2\lambda \qquad (81)$$

Now, the ratio in volume between the liquid crystal 105 and the liquid crystal molecules 104 is represented by ff". In order to bring about a sufficient effect as the variable focal-length lens, it is desirable to satisfy the following condition:

$$0.5 < ff'' < 0.999 \qquad (82)$$

If the value of the ratio ff" exceeds the upper limit of Condition (82), the amount of polymer will be so reduced that the fine cells of the liquid crystal molecules 104 cease to be formable. Below the lower limit, the effect of the variable focal-length, namely the amount of change of the focal length is reduced.

In an attempt to increase the amount of polymer so that the liquid crystal 105 approaches a solid phase, it is desirable to satisfy the following condition, instead of Condition (82):

$$0.1 < ff'' < 0.5 \qquad (83)$$

The variable optical-property element using the macromolecular stabilized liquid crystal already mentioned also satisfies at least one of Conditions (80)-(83).

Figure 53:
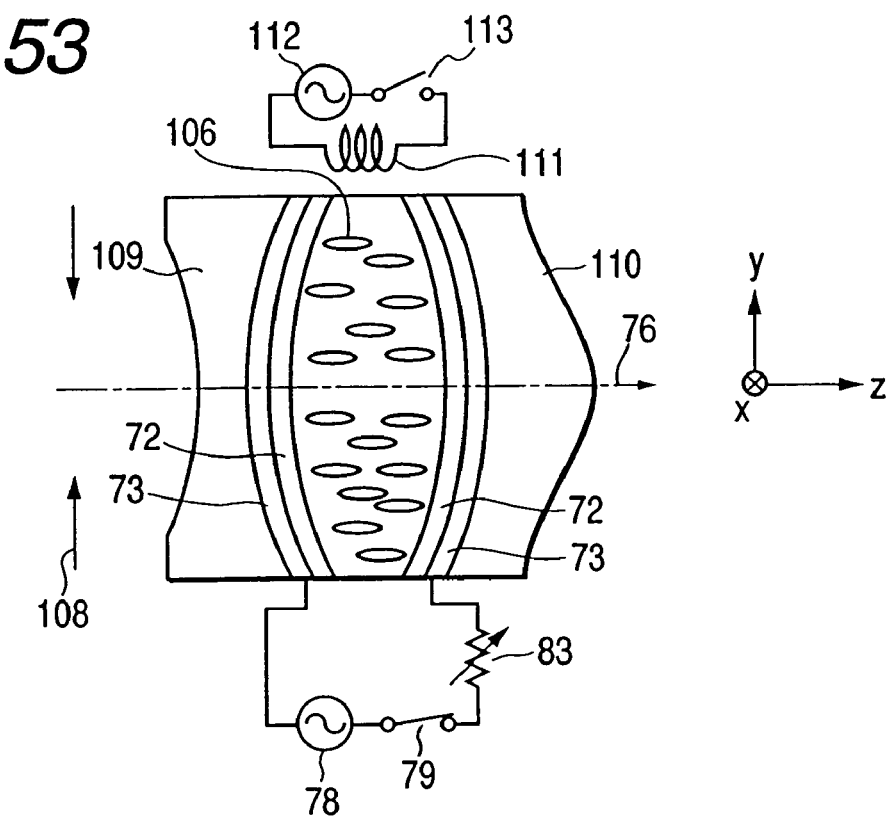
FIG. 53 is a view showing a liquid crystal lens provided with a heater.

FIG. 53 shows the embodiment of an optical system in which the refractive index of a liquid crystal is changed by temperature in the present invention. At a transition temperature Tc or less, a nematic liquid crystal 106 having a positive anisotropy of refractive index, as illustrated in FIG. 53, shows the homeotropic orientation in which the major axes of molecules point in the z direction and lies in a state of the refractive index $n_0$ which is relatively low. In this case, the switch 79 is in an on state.

Figure 54:
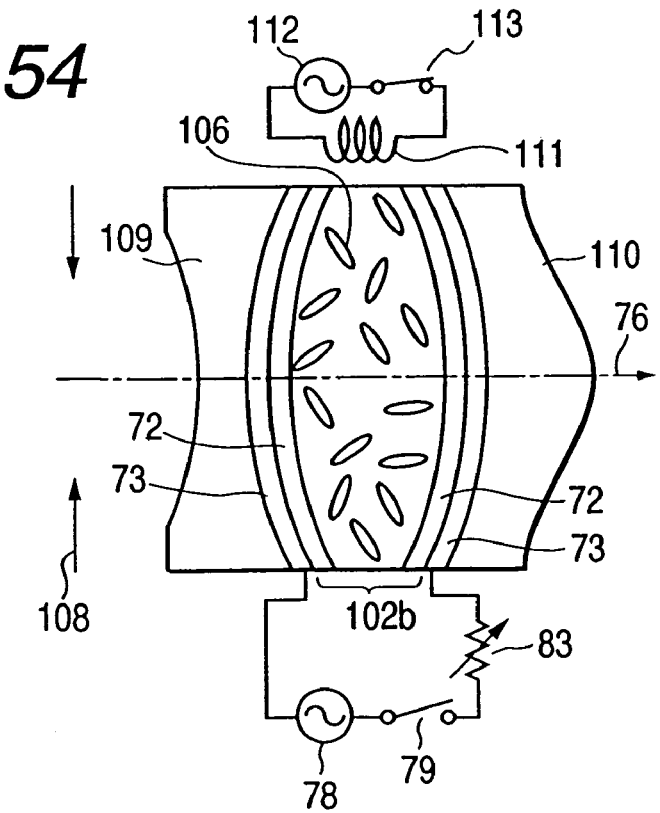
FIG. 54 is a view showing a change of the orientation of liquid crystal molecules caused by heating of the heater in FIG. 53.

When a switch 113 of a heater 111 is turned on and the liquid crystal 106 is heated by the heater 111 so that the temperature of the molecules of the liquid crystal 106 becomes higher than the transition temperature Tc, as shown in FIG. 54, the liquid crystal 106 changes to a transparent liquid in which the molecules of the liquid crystal 106 move randomly. In this case, the switch 79 is kept in an off state. In a state of FIG. 54, the refractive index n of the liquid crystal 106 is given by $$n = (2n_0 + ne)/3 \qquad (84)$$

In other words, the refractive index of the liquid crystal becomes higher and consequently, the refracting power of a positive lens 102b is strengthened.

In a state of FIG. 53, if the orientational regulating force by the orientation films 72 is sufficient, the switch 79 may be turned off. However, when the switch 79 is turned on, the molecules of the liquid crystal 106 are regularly arranged, and thus the scattering of light caused by the molecules of the liquid crystal 106 can be prevented, which is favorable.

In order to cause a liquid phase transition to the liquid crystal, the optical system uses the heater 111 for heating, but the frequency of the AC power supply may be increased to thereby heighten vibrations of the molecules of the liquid crystal 106 so that the temperature is raised and the phase transition is made.

The variable optical-property element of the present invention stated above is constructed so that the strength and direction of the electric field are mainly varied to thereby change the orientation of the molecules of the liquid crystal constituting the optical element. However, the orientation of the liquid crystal can be shifted not only by varying the strength of the electric field, but also by changing the frequency of the electric or magnetic field. Moreover, the orientation of the molecules of the liquid crystal can also be shifted by changing the strength of the magnetic field.

Techniques of shifting the orientation of the molecules of the liquid crystal by changing the frequency of the electric field applied to the liquid crystal and of changing the strength of the magnetic field applied to the liquid crystal as mentioned above are applicable to the optical systems cited as examples in FIGS. 36, 38, 43, 44, 47, 50, 51, and 54, and FIG. 55 described below.

In the technique of shifting the orientation of the molecules of the liquid crystal by changing the frequency of the electric field, the use of a liquid crystal in which the positive sign of the anisotropy of refractive index is replaced with the negative sign is particularly advantageous because the orientation of the molecules of the liquid crystal can be shifted with high speed in accordance with the change of the frequency of the electric field.

Figure 55:
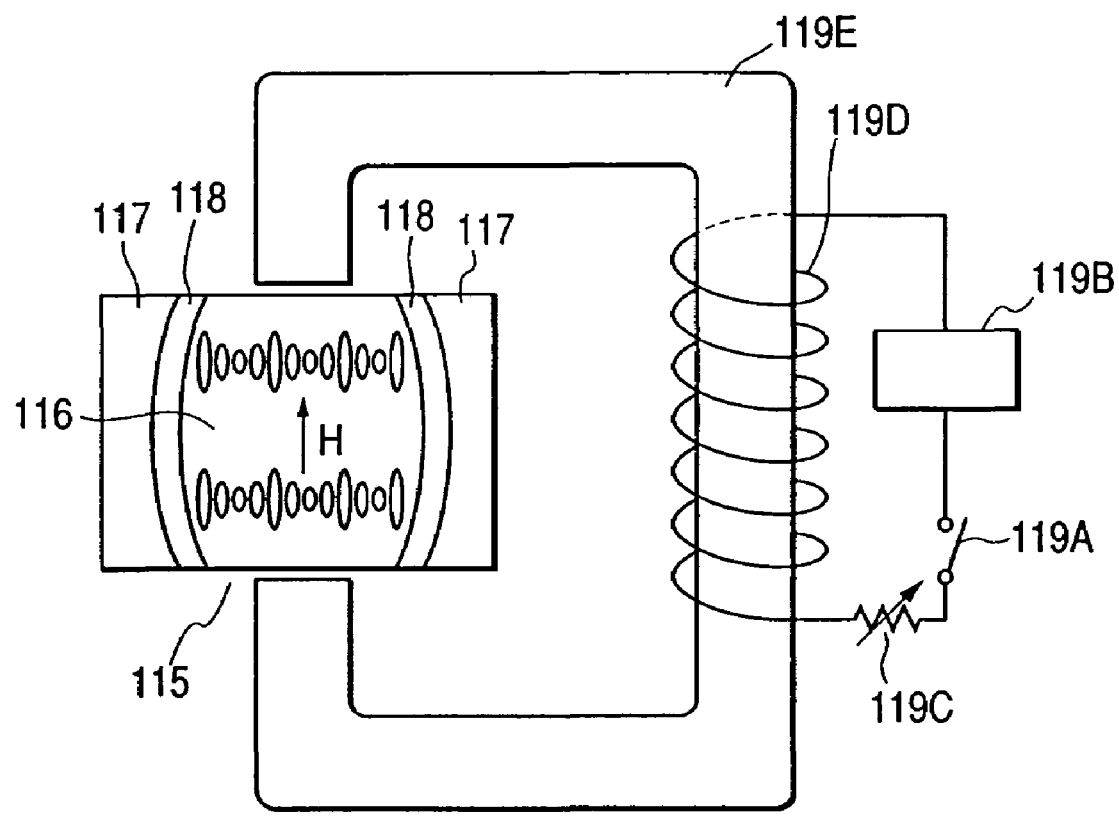
FIG. 55 is a view showing an example in which the orientation of liquid crystal molecules is changed by a magnetic field.

FIG. 55 shows a lens in which the refractive index is changed by the magnetic field H. In this figure, reference numeral 115 denotes a lens; 116, a substance possessing a magnetrooptical effect; 117, substrates; 118, orientation films; 119A, a switch; 119B, an AC power supply; 119C, a variable resistor; 119D, a coil; and 119E, an iron core.

As an example of the substance 116, lead glass, quartz, or a liquid crystal is cited. In the case of the liquid crystal, it is favorable to use the orientation films 118.

In order to shift the orientation of the molecules of the liquid crystal with high speed, it is desirable to previously applying some degree of voltage instead of removing the voltage. In this way, where the orientation is changed, the voltage is made higher and thereby the orientation can be changed with high speed.

The embodiment shown in FIG. 47, which is the imaging device for digital cameras of the present invention using the variable optical-property element, will be described in more detail below.

In FIG. 47, an optical system 101 is placed which is constructed with the variable focal-length liquid crystal 91 including the liquid crystal lens portion 95 and a negative lens 98 and a positive lens 99 behind the stop 96. The positive lens 99 is provided for the purpose of rendering a chief ray incident perpendicular or nearly perpendicular to a solid-state image sensor 100, for example, at an angle of 90±20° with the light-receiving surface of the image sensor.

The negative lens 98 is provided the purpose of improving the Petzval sum to correct curvature of field. A positive lens 97 situated on the side of the stop 96 (the entrance side) is such that its object-side surface is convex and thereby spherical aberration is favorably corrected. The liquid crystal lens portion 95 assumes the shape of a negative lens to correct chromatic aberration. One of the surfaces of the lenses 97, 98, and 99 is configured to be aspherical and thereby aberrations can be more favorably corrected. It is desirable that the liquid crystal lens portion 95 is located close to the stop 96 because the effective diameter of the liquid crystal lens portion 95 can be diminished and the thickness can be reduced.

When the orientation of the molecules of the liquid crystal 90 in the liquid crystal lens portion 95 is shifted, the aberration of the optical system 101 including the positive lens 97, the liquid crystal lens portion 95, the negative lens 98, and the positive lens 99 fluctuates, and the scattering of light caused by the liquid crystal lens portion 95 varies, thereby changing the MTF of the optical system 101.

The imaging device shown in FIG. 47 is designed so that the change of the MTF caused by the fluctuation of the aberration and the variation of the scattering of light is compensated by an electronic circuit. That is, the compensation for the change of the MTF caused when the focal length of the liquid crystal lens 91 is change to perform the focusing operation due to a shift of the position of an object is made by varying an enhance circuit or an image processing circuit in a circuit system 114. Specifically, it is only necessary to use a means of changing the characteristics of a digital filter like a Wiener filter or changing the amount of edge enhance of the enhance circuit. Here, the change of the MTF may be derived from the design data of the optical system 101 or the amount of compensation of the MTF may be changed by actually measuring each camera.

Figure 56:
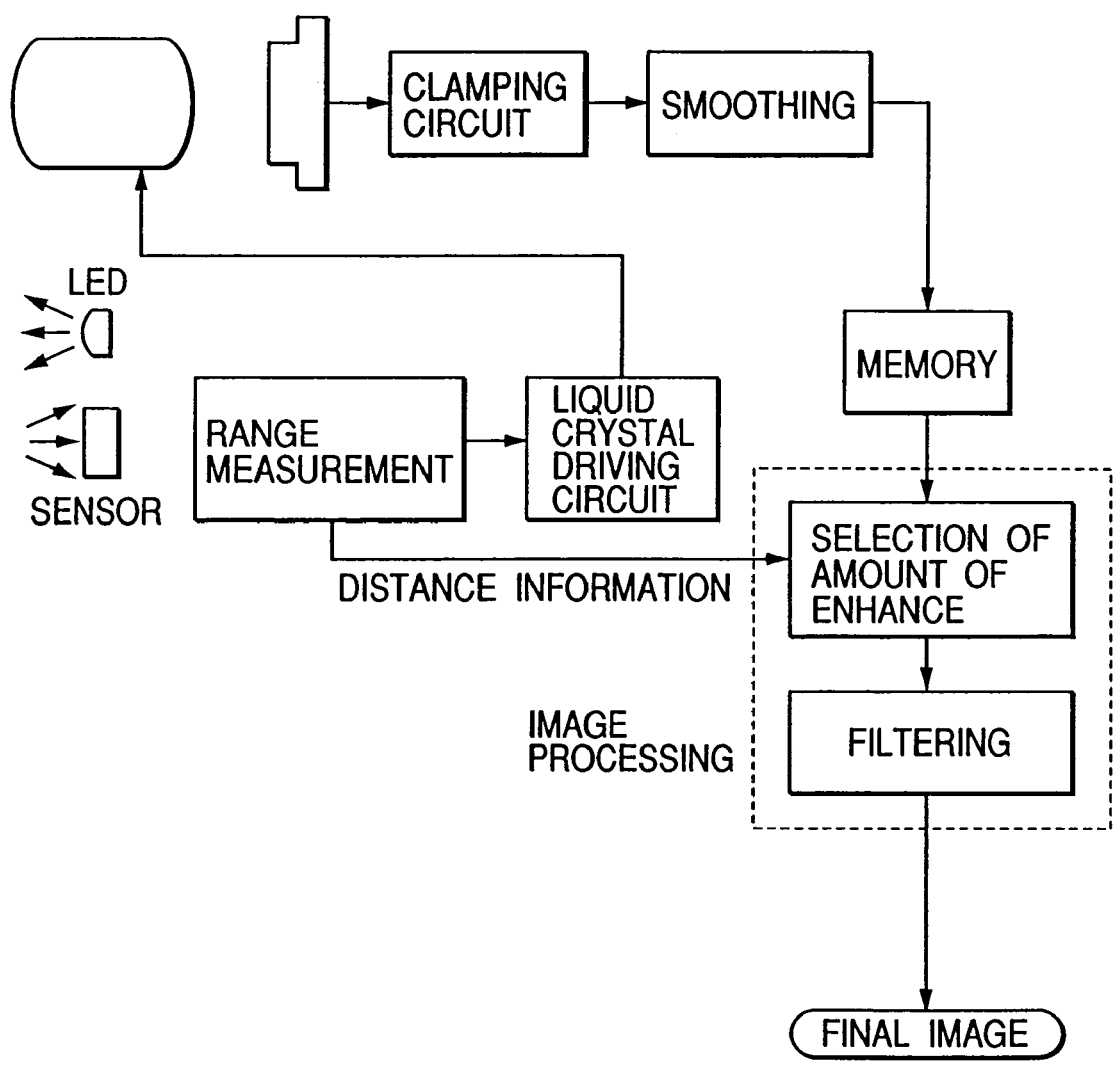
FIG. 56 is a diagram showing an electronic circuit for correcting an image derived from the imaging device of the present invention.

FIG. 56 shows a diagram in which a range measurement on an infrared projecting, active range finding technique is made with respect to the compensation by the electronic circuit. On distance information derived here, the amount of enhance is selected to compensate the change of the MTF of the liquid crystal lens. Subsequently, the digital filter is used and the final image is obtained.

Figure 57:
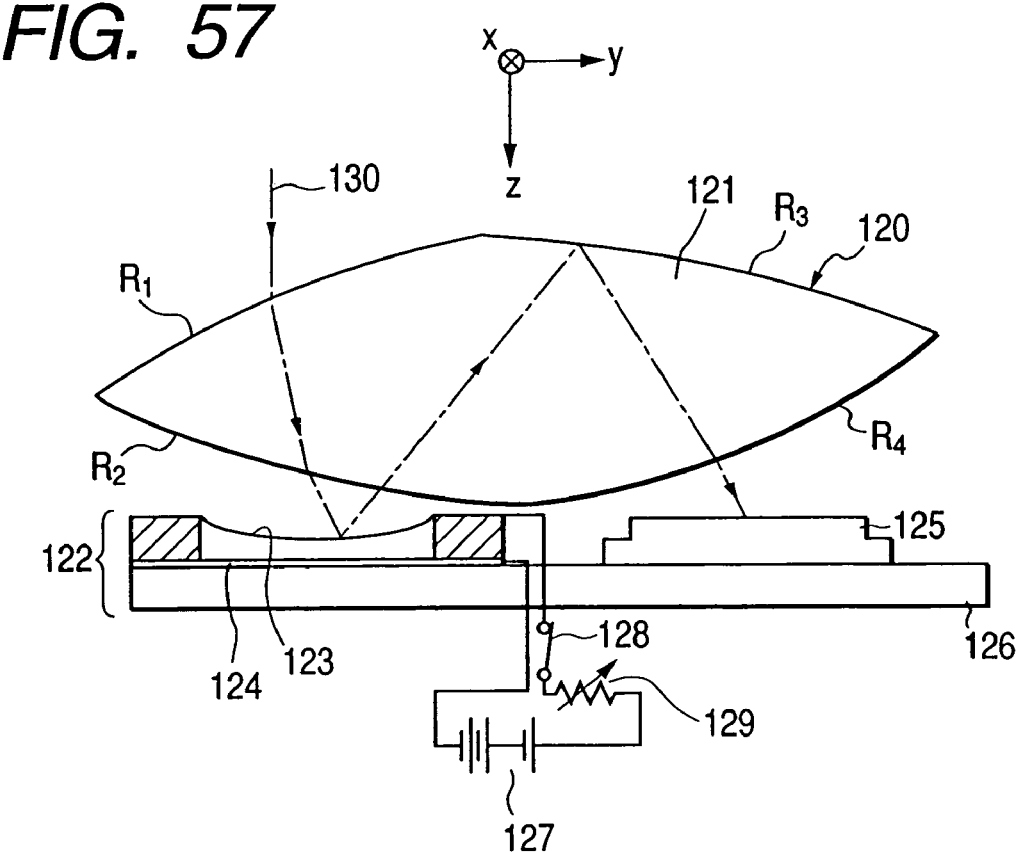
FIG. 57 is a view showing an imaging device using a variable focal-length mirror.

FIG. 57 shows a digital camera 120 using a free-formed surface prism 121 (a prism having irrotational symmetric surfaces) in the present invention. Reference numeral 122 represents a variable focal-length mirror; 123, a thin film coated with aluminum; 124, an electrode; 125, a solid-state image sensor; 126, a substrate; 127, a power supply; 128, a switch; and 129, a variable resistor.

As an example of the variable focal-length mirror 122, a membrane mirror is cited which is set forth in "Optics Communications", Vol. 140, pp. 187-190, 1997. When a voltage is applied across the electrode 124, the thin film 123 is deformed by an electrostatic force and the focal length of a reflecting mirror is changed. In this way, a focusing adjustment can be made. Light 130 from an object is refracted by surfaces $R_1$ and $R_2$, and after being reflected by the reflecting mirror (thin film) 123 and a surface $R_3$ of the free-formed surface prism 121, is refracted by a surface $R_4$ and falls on the solid-state image sensor 125.

Thus, this device constructs an imaging optical system with the free-formed surfaces $R_1$, $R_2$, $R_3$, and $R_4$ and the reflecting mirror 123. In particular, by optimizing the shapes of the free-formed surfaces $R_1$, $R_2$, $R_3$, and $R_4$, aberration of an object image is reduced to a minimum.

In the imaging device of FIG. 57, in order to correct astigmatism, it is desirable that the aperture of the reflecting mirror is shaped into an elliptic form which has its major axis along the direction of the y axis, that is, of a line that a plane including incident light on the reflecting mirror 122 and emergent light therefrom crosses the reflecting mirror 122. In this figure, the reflecting mirror 122, the thin film 123, and the solid-state image sensor 125 are constructed to be independent of one another and placed on the substrate 126. Since, however, the reflecting mirror 122 and the thin film 123 can also be fabricated through a silicon lithography process, the substrate 126 may be constructed of silicon so that at least one part of the reflecting mirror 122 is fabricated, together with the solid-state image sensor 125, on the substrate 126 by the lithography process.

In this way, the reflecting mirror 122 is integrated with the image sensor 125, and this is advantageous for compactness and a reduction in cost. Moreover, the reflecting mirror 122 may be constructed with a fixed-focus mirror. In this case also, the reflecting mirror 122 can be made through the lithography process.

A reflection type liquid crystal display or a transmission type liquid crystal display, although not shown in the figure, may be constructed integrally with the substrate 126 through the lithography process. The substrate 126 may be made of glass, and it is only necessary to construct the solid-state image sensor and the liquid crystal display on this glass substrate through the technique, for example, of a thin film transistor. The free-formed surface prism 121 is configured with plastic or glass molding and thereby curved surfaces of any desired shape can be easily configured and fabrication is simplified.

Figure 58:
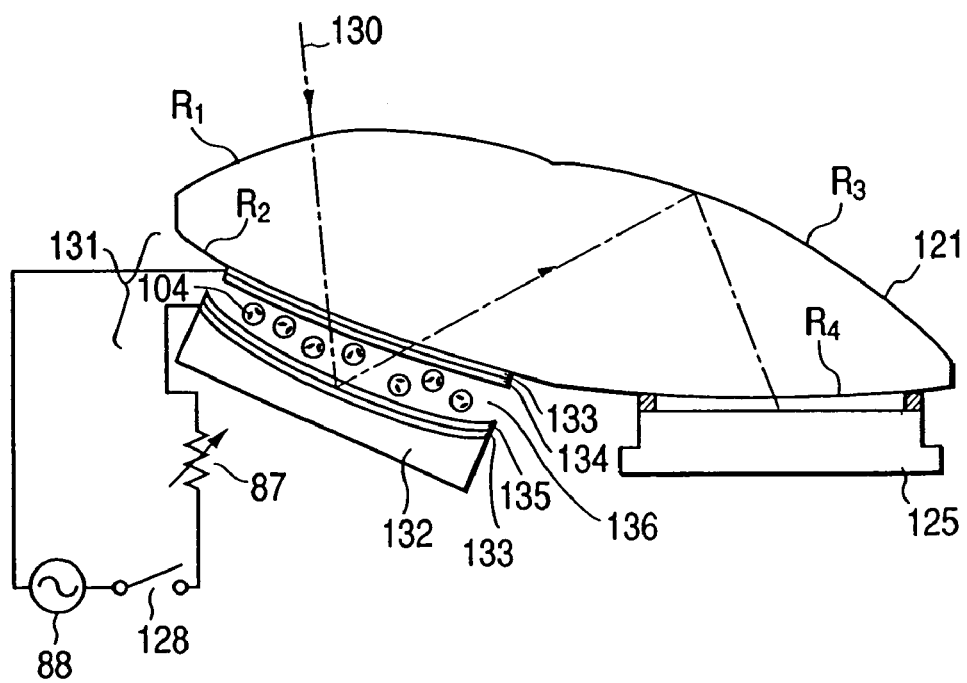
FIG. 58 is a view showing one modification example of the mirror of FIG. 57.

FIG. 58 shows another digital camera using the free-formed surface prism 121. This digital camera, instead of using the reflecting mirror 122 of the digital camera in FIG. 57, uses a variable focal-length mirror 131. The variable focal-length mirror 131 is provided integrally with the free-formed surface prism 121 on the surface $R_2$ of the prism 121. The variable focal-length mirror 131 is comprised of a reflecting mirror 132, transparent electrodes 133, one of which is provided on the surface $R_2$ of the prism 121, and orientation films 134 and 135 and has a liquid crystal 136 between the orientation films 134 and 135. Here, the variable focal-length mirror 131 may be constructed to be independent of the free-formed surface prism 121 so that both are cemented or the electrode 133 and the orientation film 134 may be provided on the surface $R_2$ of the prism 121.

The light 130 incident on the digital camera from the object, as in FIG. 57, is refracted by the surfaces $R_1$ and $R_2$ and after being reflected by the reflecting mirror 132, passes through the orientation film 135, the liquid crystal 136, the orientation film 134, and the transparent electrode 133 to enter the free-formed surface prism 121. After reflection by the surface $R_3$ and emergence from the surface $R_4$, the light falls on the light-receiving surface of the solid-state image sensor 125. Here, when the voltage applied to the variable focal-length mirror 131 is varied, the focal length of the mirror 131 is changed and thus the focusing adjustment can be made.

The macromolecular dispersed liquid crystal is used for the liquid crystal 136 of the variable focal-length mirror 131. As described in connection with FIGS. 50-52, the electric field applied to the liquid crystal 104 is changed and thereby the situation is changed, for example, from FIG. 51 to FIG. 52. Consequently, the refractive index of the liquid crystal is changed and the focal length of the variable focal-length mirror is varied.

The digital camera shown in FIG. 58 has the same function as a digital camera using the liquid crystal lens of FIG. 51 even though the electrodes 92 and 93 of FIG. 51 are not used. Specifically, in FIG. 58, when the switch 128 is turned off, the molecules of the liquid crystal are oriented randomly in a state of high refractive index. Hence, the variable focal-length mirror 131 has a strong function of converging the light. Here, when the switch is turned on, the molecules are oriented in one direction, and thus the refractive index becomes lower, reducing the function of converging the light. In this way, the focusing adjustment of the variable focal-length mirror 131 is performed. If at least two variable focal-length mirrors 131 are used in the free-formed surface prism 121, this device can be used as a zoom lens system.

The variable focal-length mirror 122 shown in FIG. 57 may be replaced with the variable focal-length mirror 131 of FIG. 58. In this case, the orientation films 134 and 135 need not necessarily be used. In addition, the transparent electrode 133 may be substituted by the reflecting mirror 132 also used as an electrode which is constructed as the liquid crystal optical element of the variable focal-length mirror 131. Instead of the macromolecular dispersed liquid crystal 136, the nematic liquid crystal of a helical orientation, as well as the cholesteric liquid crystal and the smectic liquid crystal, may be used.

Figure 59:
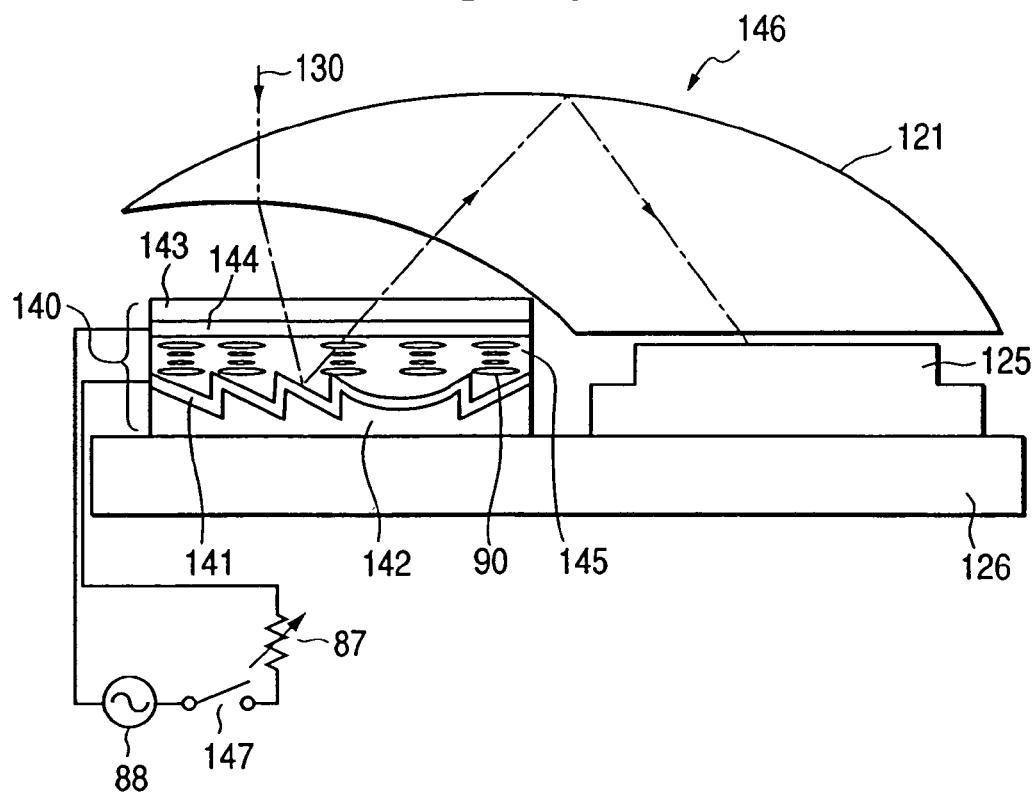
FIG. 59 is a view showing another modification example of the mirror.

FIG. 59 shows an example in which a diffraction optical element 140 is used instead of the reflecting mirror 122 or the variable focal-length mirror 131 shown in FIG. 57 or 58. The diffraction optical element 140 is constructed with a diffraction surface 141 configured on a reflecting mirror 142, a transparent electrode 143, an orientation film 144, and a liquid crystal 145.

In a digital camera 146 shown in FIG. 59, the light 130 from the object, as in the above embodiment, is incident on the free-formed surface prism 121, and after being transmitted through the prism 121, enters the diffraction optical element 140. The light, after being diffracted by the diffraction surface 141, leaves the diffraction optical element 130 and is again incident on the free-formed surface prism 121. By being reflected as shown in the figure, the light emerges from the prism 121 and falls on the solid-state image sensor 125.

Here, when a switch 147 is turned on, the orientation of the molecules of the liquid crystal 90 is shifted so that the molecules are oriented in a vertical direction, and the order of diffraction of the diffraction optical element 140 is changed. In this way, the focal length is varied and the focusing operation can be performed. In this case, the pitch of the molecules of the liquid crystal 90, as in FIG. 47, satisfies Condition (69). In this embodiment, the diffraction surface 141 is configured as a reflecting surface, and a reflection type diffraction optical element is presented.

Figure 60:
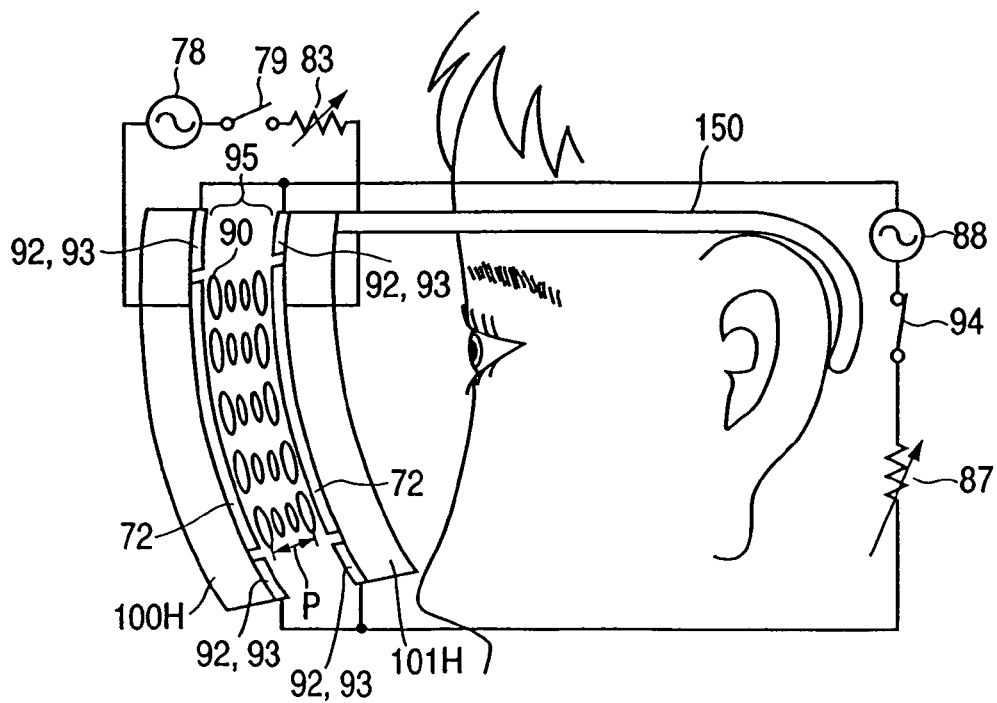
FIG. 60 is a view showing variable focal-length spectacles.

FIG. 60 illustrates variable focal-length spectacles, each having the variable focal-length lens. The variable focal-length lens is used as an eyeglass lens. The variable focal-length lens including lenses 100H and 101H, the orientation films 72 (not shown), and the electrodes (whose part is not shown) is attached to a frame 150 of the spectacles.

In this variable focal-length lens, the electrodes 92 and 93, as in FIG. 51, are provided on the peripheries of the lenses 100H and 101H. When the electrodes 92 and 93 are configured as transparent electrodes, the periphery of the visual field of the spectacles becomes bright, which is favorable.

In the embodiments mentioned above, the variable focal-length lens is used as the variable optical-property element, but a diffraction optical element, Fresnel lens, prism, or lenticular lens may be used as the variable optical-property element. It is merely necessary that a portion subjected to the diffraction or reflection of light, constituting each element, is replaced by a variable refractive-index substance, that is, a liquid crystal, ferroelectric, or substance possessing an electrooptic effect. In order to shift the orientation of the molecules of the liquid crystal, the frequency of an electric or magnetic field may be changed.

The optical system using the variable optical-property element of the present invention stated above can be employed in a photographing device in which an object image is formed and received by an image sensor, such as a CCD or a silver halide film, for photography, notably a camera or an endoscope. Furthermore, the optical system can also be used as an observation device for observing an object image through an eyepiece, and in particular, as an objective optical system which is a part of the finder of a camera. The embodiments of such optical systems are described below.

Figure 61:
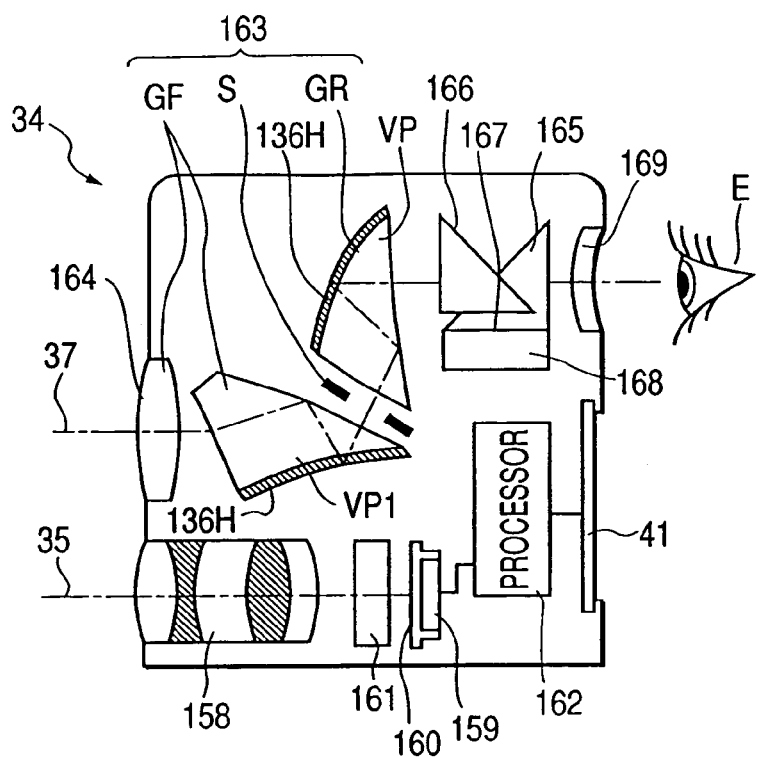
FIG. 61 is a view showing the interior arrangement of an electronic camera to which the present invention is applied.

In FIGS. 28, 29, and 61, the electronic camera 34 includes the photographing optical system 36 having a photographing optical path 35, the finder optical system 38 having the finder optical path 37, the release 39, the flash lamp 40, and the liquid crystal display monitor 41. When the release 39 provided on the upper side of the camera 34 is pushed, photography is performed through a photographing objective optical system 158 in association with the operation of the release 39. The photographing objective optical system 158 is provided with a plurality of transmission type variable optical-property elements (using liquid crystals here, indicated by hatching portions in the figure) to perform the zooming and focusing operations. An object image formed by the objective optical system 158 falls on an imaging surface 160 of a CCD 159 through a filter 161 such as a low-pass filter or an infrared cutoff filter. The object image received by the CCD 159 is displayed as an electronic image, through a processing means 162, on the liquid crystal display monitor 41 provided on the back side of the camera 34. The processing means 162 has a memory and is also capable of recording the electronic image photographed. Also, this memory may be provided to be independent of the processing means 162 or may be designed to electronically execute record/write with a floppy disk. The camera may be constructed as a silver halide film camera provided with a silver halide film instead of the CCD 159.

Moreover, on the finder optical path 37, an imaging optical system provided with reflection type variable optical-property elements 136H is placed as a finder objective optical system 163. A cover lens 164 with positive power is provided as a cover member to enlarge an angle of view. The cover lens 164 and a prism VP1 situated on the object side of a stop S of the imaging optical system constitute a front lens unit GF of the finder objective optical system 163, while a prism VP situated on the image side of the stop S constitutes a rear lens unit GR thereof. The variable optical-property elements 136H are arranged respectively in the front and rear lens units GF and GR sandwiching the stop S therebetween, and thereby the zooming and focusing operations are performed. This optical system uses the reflection type variable optical-property elements, each of which is constructed integrally with a reflecting prism. The liquid crystals 136H are used in these elements, and the zooming and focusing operations are performed by changing the optical property as mentioned above. The control of the properties of each liquid crystal is made by the processing means in association with the zooming and focusing operations of the photographing objective optical system. An object image formed by the finder objective optical system 163 is placed on a field frame 167 of a Porro prism 165 which is an image erecting member. The field frame 167 separates a first reflecting surface 166 of the Porro prism 165 from a second reflecting surface 168, and is interposed between them. An eyepiece optical system 165 which introduces an erect image into an observer's eye E is placed behind the Porro prism 165. In the camera 34 designed as mentioned above, the finder objective optical system 163 can be constructed with a small number of optical members, and high performance and compactness are achieved. Furthermore, since the optical path of the objective optical system 163 can be bent, the number of degrees of freedom of layout in the camera is increased, and this is advantageous for design.

Figure 62:
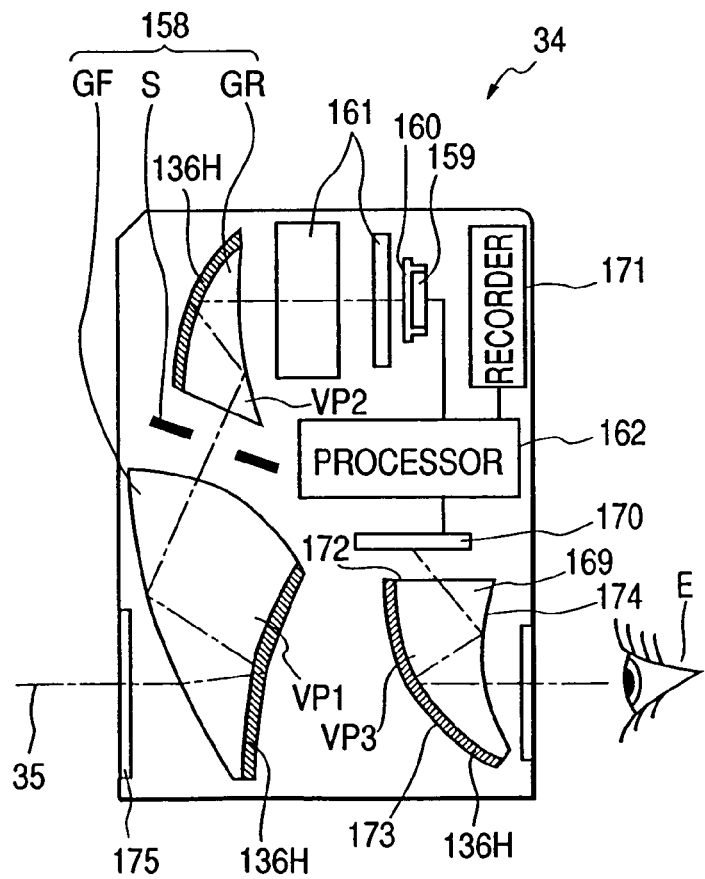
FIG. 62 is a view showing one modification example of FIG. 61.

FIG. 62 shows a case where the imaging optical system of the present invention is incorporated in the objective optical system 158 of the photographing section of the electronic camera 34. In this case, the photographing objective optical system 158 situated on the photographing optical path 35 is an imaging optical system using the reflection type variable optical-property elements. An object image formed by the photographing objective optical system 158 falls on the imaging surface 160 of the CCD 159 through the filters 161 such as a low-pass filer and an infrared cutoff filter. The object image received by the CCD 159 is displayed as an electronic image, through the processing means 162, on a liquid crystal display (LCD) 170. The processing means 162 also controls a recording means 171 which records the object image obtained by the CCD 159 as electronic information. The object image displayed on the LCD 170 is introduced through an eyepiece optical system 169 into the observer's eye E. The eyepiece optical system 169 includes a decentered prism VP3 provided with the variable optical-property element 136H which has the same aspect as those used in the imaging optical system of the present invention. By controlling the properties of the element 136H, the depth of a virtual image in the LCD 170 can be adjusted in accordance with the diopter of the observer. The prism VP3 includes an entrance surface 172, a reflecting surface 173, and a surface 174 used for both reflection and refraction. At least one of the surfaces 173 and 174 having two reflecting functions, preferably both, are constructed with symmetrical free-formed surfaces, each of which provides a light beam with power and has only one symmetrical surface for correcting decentered aberration. Such symmetrical surfaces are situated on nearly the same plane as those of the symmetrical free-formed surfaces of the decentered prisms VP1 and VP2 which are arranged in the front and rear lens unit GF and GR of the photographing objective optical system 158.

Figure 63:
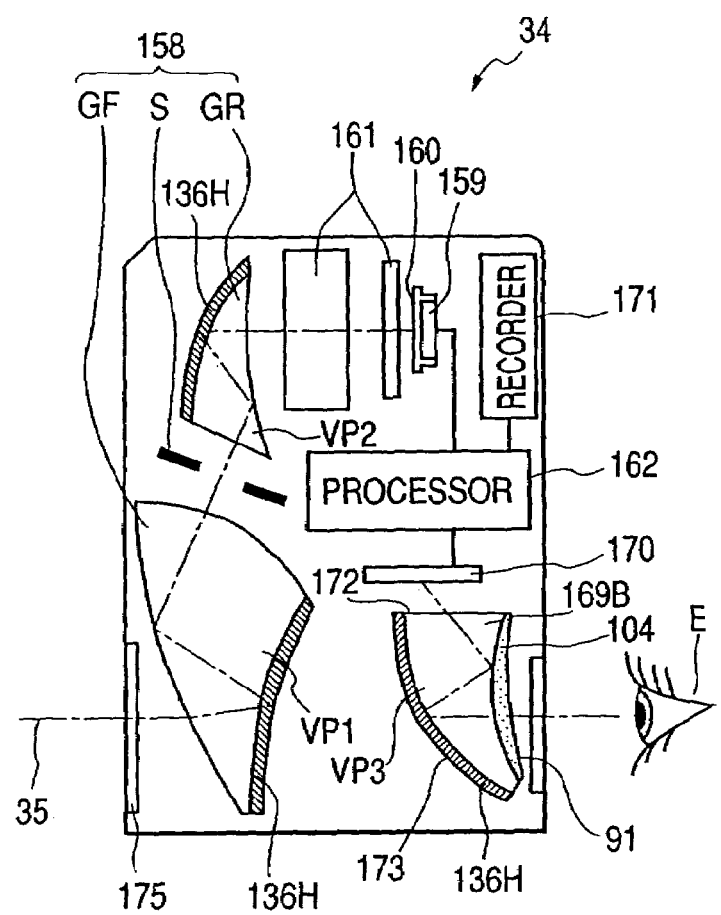
FIG. 63 is a view showing another modification example of FIG. 61.

FIG. 63 shows another case where the imaging optical system of the present invention, as in FIG. 62, is incorporated in the objective optical system 158 of the photographing section of the electronic camera 34. In this case, an eyepiece optical system 169B is different from that of FIG. 62. Specifically, the electronic camera shown in FIG. 63 is provided with the variable focal-length lens 91, such as that shown in FIG. 47, in the proximity of the exit surface 174 of the decentered prism VP3 in the eyepiece optical system 169 of FIG. 62. In this way, the decentered prism VP3 is combined with the variable focal-length lens 91, and thereby both the conversion of diopter by the decentered prism and the change of magnification by the variable focal-length lens can be carried out.

In the camera 34 designed as mentioned above, the photographing objective optical system 158 can be constructed with a small number of optical members, and high performance and compactness are achieved. In addition, since the entire optical system is placed in the same plane, the thickness of the camera in a direction perpendicular to this plane can be reduced.

Figure 64:
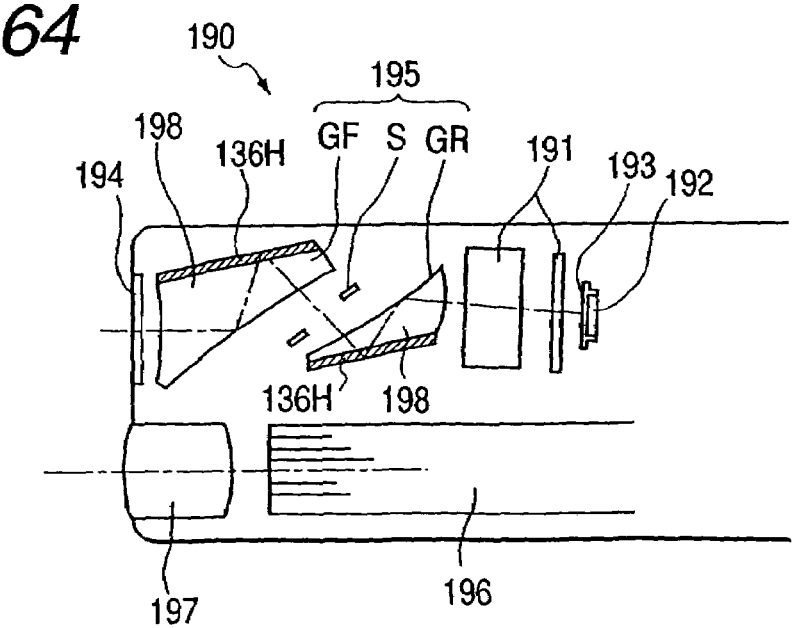
FIG. 64 is a view showing the interior arrangement of the distal end of the endoscope of FIG. 32 in which the variable optical-property element of the present invention is incorporated.

FIG. 64 shows an optical system 190 of an electronic endoscope in which the variable optical-property element of the present invention is incorporated. In this case, an objective optical system 195 for observation uses an imaging optical system provided with reflection type variable optical-property elements 198 for performing the zooming and focusing operations. The reflection type variable optical-property elements 198 employ the liquid crystals 136H. The electronic endoscope is constructed like the electronic endoscope 53 shown in FIG. 32. The distal end 61 of the inserting section 60 of the electronic endoscope 53 is constructed as shown in FIG. 64. An illumination light beam from the light source device 54 passes through a light guide fiber bundle 196 and illuminates a part to be observed, through an objective optical system 197 for illumination. Light from the part to be observed is such that an object image is formed through a cover member 194 by the objective optical system 195 for observation. The object image falls on an imaging surface 193 of a CCD 192 through filters 191 such as a low-pass filter and an infrared cutoff filter. Subsequently, the object image is converted into an image signal by the CCD 192. This image signal is displayed directly on the monitor 56 by the video processor 55 shown in FIG. 32, and is recorded in the VTR deck 57 and the video disk 58 and printed out as an image by the video printer 59. The endoscope designed in this way can be constructed with a small number of optical members, irrespective of the fact that zooming and focusing functions are retained, and is capable of achieving high performance and compactness.

Each of the decentered prisms provided in the front and rear lens units of the imaging optical system is of a two-internal-reflection type, including three optical surfaces, one of which has the functions of total reflection and of refraction. However, the decentered prism used in the present invention is not limited to such a structure. Also, in the present invention, instead of the free-formed surface prism, a free-formed surface reflecting mirror may be used.

In the imaging device of the present invention described above, the imaging device shown in FIG. 57, for example, is provided with the optical system including the free-formed surfaces and the variable focal-length mirror. However, these free-formed surfaces can also be used in the optical systems of other imaging devices using the variable optical-property elements. It is possible to use such free-formed surfaces, for example, in the optical system of the imaging device using the variable focal-length lens depicted in FIG. 47. In other words, the free-formed surfaces are applicable to optical systems, imaging optical systems, optical devices, and observation devices which use variable optical-property elements in addition to variable optical-property reflecting mirrors.

The optical system of the present invention is used as an eyepiece optical system, a finder optical system, the lens system of an electronic imaging device (in FIG. 50, for example), and the lens system of a digital camera imaging device.

Figure 65:
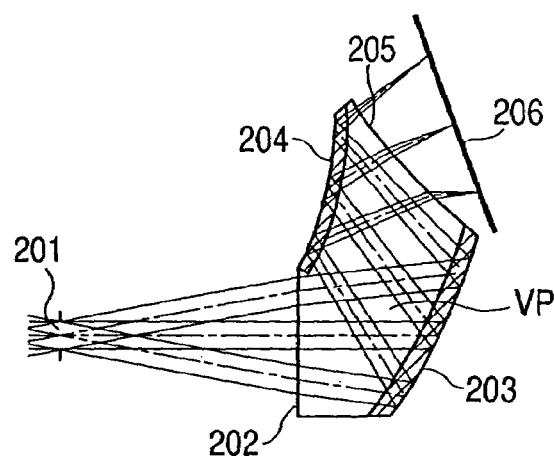
FIGS. 65-67 are views showing examples of decentered prisms applicable in the present invention.
Figure 66:
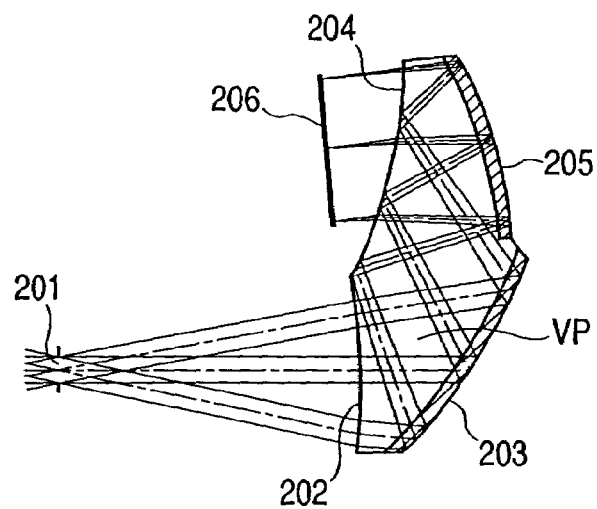
Figure 67:
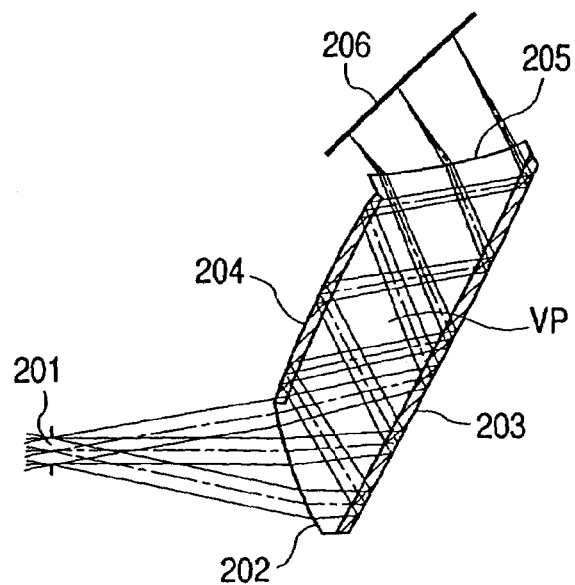

A few examples of the variable focal-length prisms which can be used in the present invention are shown in FIGS. 65-67. Although in any case the prism VP forming an image on an image plane 206 is depicted in the figure, the prism VP can also be used in such a way that the direction of the optical path is reversed, that is, rays of light from an object are rendered incident from the side of the image plane 206 to form the image on the side of a pupil 201. The prism VP may be designed to construct an imaging optical system or an observation optical system by itself. Which of the surfaces of the prism should be used for the variable optical-property element may be determined in accordance with the application of the prism.

In FIG. 65, the prism VP includes a first surface 202, a second surface 203, a third surface 204, and a fourth surface 205. Light passing through the entrance pupil 201, after being refracted by the first surface 202 to enter the prism VP, is internally reflected by the second surface 203 and enters the third surface 204 for internal reflection. The light is then incident on the fourth surface 205 and is refracted there to form an image on the image plane 206. The variable optical-property elements are provided on the second and third surfaces 203 and 204, and thereby zooming and focusing become possible.

In FIG. 66, the prism VP includes the first surface 202, the second surface 203, the third surface 204, and the fourth surface 205. Light passing through the entrance pupil 201, after being refracted by the first surface 202 to enter the prism VP, is internally reflected by the second surface 203 and enters the third surface 204 for total reflection. The light is then incident on the fourth surface 205 and is internally reflected there. Finally, the light is incident again on the third surface 204 and is refracted there to form an image on the image plane 206. In this case, the variable optical-property elements are used for the second and fourth surfaces 203 and 205.

In FIG. 67, the prism VP includes the first surface 202, the second surface 203, the third surface 204, and the fourth surface 205. Light passing through the entrance pupil 201, after being refracted by the first surface 202 to enter the prism VP, is internally reflected by the second surface 203 and enters the third surface 204 for internal reflection. The light is then incident again on the second surface 203 and is internally reflected there. Finally, the light is incident on the fourth surface 205 and is refracted there to form an image on the image plane 206. In this case, the variable optical-property elements are used for the second and third surfaces 203 and 204.

Figure 68:
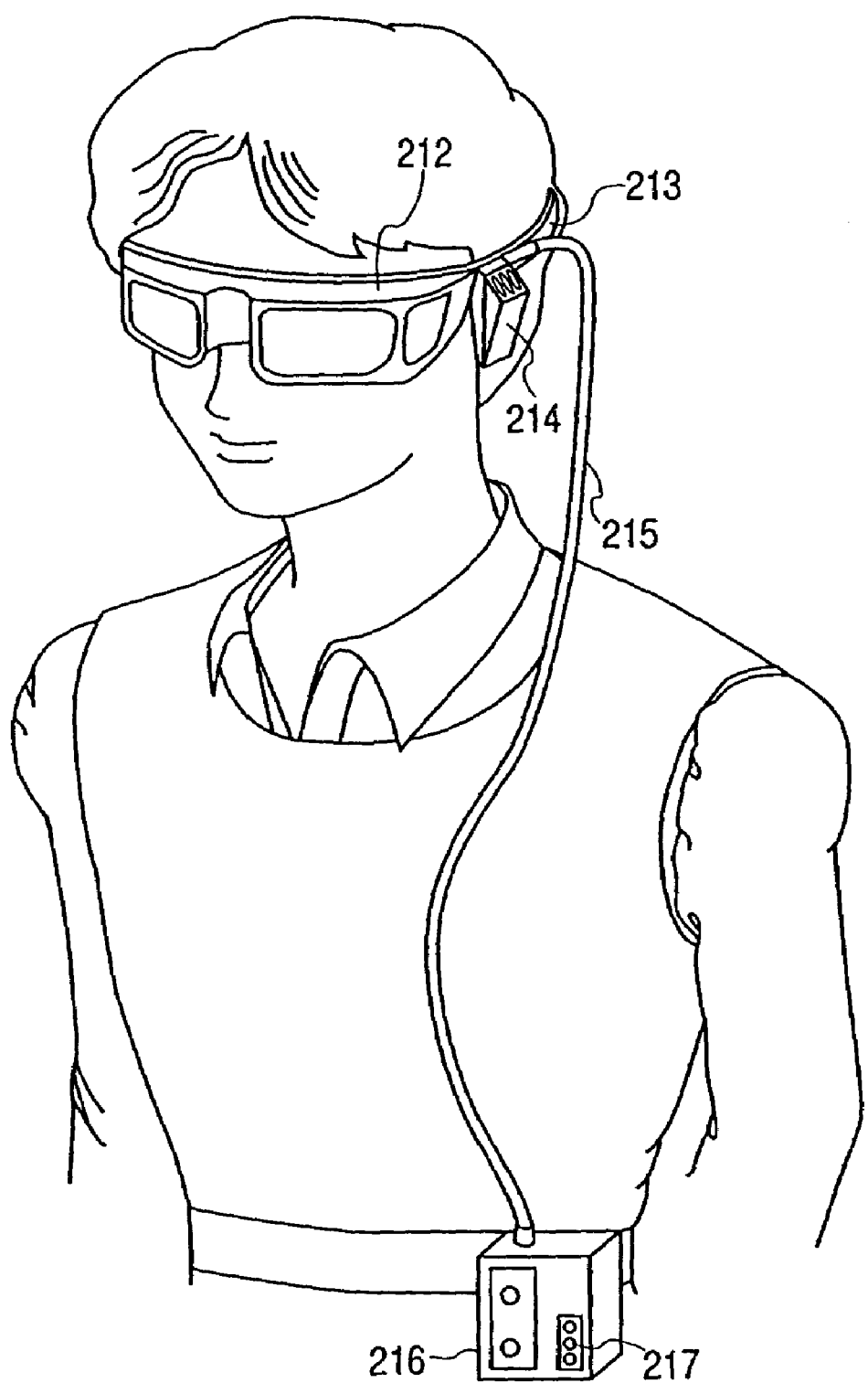
FIG. 68 is a view showing an image display device using variable optical-property elements in the present invention.
Figure 69:
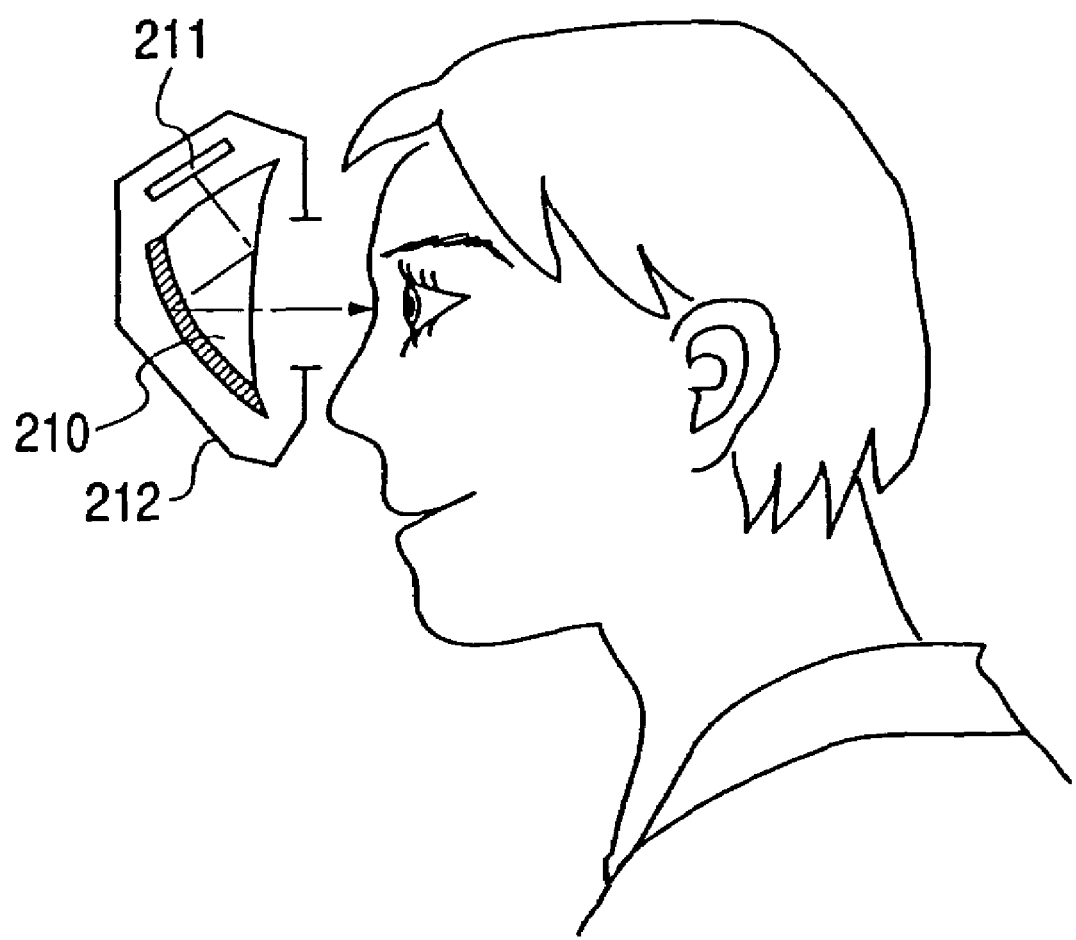
FIG. 69 is a sectional view showing the image display device of FIG. 68.

The variable optical-property element of the present invention can be utilized for an image display. In FIGS. 68 and 69, a decentered prism optical system in which the reflection type variable optical-property element of the present invention is used for diopter adjustment, as shown in FIG. 69, is used as an eyepiece optical system 210. A pair of combinations, each including the eyepiece optical system 210 and an image display element 211, is provided so that the combinations are separated by an interpupillary distance and supported, thereby constructing a portable image display 212 such as a stationary or head mounted image display which is observable with the eyes.

Specifically, the display body 212 is provided with a pair of eyepiece optical systems 210 for the eyes and, opposite thereto, has the image display elements 211, such as liquid crystal display elements, at the position of the image plane. Moreover, the display body 212, as shown in FIG. 68, has a temple frame 213 which extends continuously on both sides so that the display body 212 can be retained before an observer's eyes.

A speaker 214 is attached to the temple frame 213 so that an observer can enjoy not only an image observation, but also a stereoscopic sound. In this way, since the display body 212 having the speaker 214 is connected through an image sound transmitting cord 215 to a video reproducing device 216 such as a portable video cassette, the observer, as shown in the figure, is capable of holding the reproducing device 216 at any position of his belt to enjoy an image sound. In FIG. 68, reference numeral 217 represents a control section for the switch and volume of the reproducing device 216. Also, electronic parts such as image and sound processing circuits are housed in the display body 212.

The cord 215 may be designed so that its tip as a jack can be attached to the existing video deck. Moreover, it may be connected to a tuner for TV electric wave reception to watch TV, or may also be connected to a computer so as to receive the image of computer graphics or a message image from the computer. To remove a cord which is obstructive to the operation, an antenna may be provided to receive a signal from the outside through the electric wave.

As is true of the whole of the present invention, each of the eyepiece optical system, the finder optical system, the lens system of the electronic imaging device (in FIG. 50, for example), and the lens system of the digital camera imaging device is cited as an example of the imaging optical system.

In general, the present invention has the following features.

1. A variable optical-property element includes a liquid crystal in which the pitch of twist is less than 60 times the wavelength of light used, so that a spatially uneven electric or magnetic field or temperature is applied to the liquid crystal to thereby form an index distribution; and so that the electric or magnetic field or the temperature is changed to thereby alter the index distribution.

2. A variable optical-property element includes a macromolecular dispersed liquid crystal so that a spatially uneven electric or magnetic field or temperature is applied to the liquid crystal to thereby form an index distribution, and so that the electric or magnetic field or the temperature is changed to thereby alter the index distribution.

3. A variable optical-property element includes a combination of at least two liquid crystal lenses with positive and negative powers.

4. In item 1, the variable optical-property element uses the wavelength of light within the wavelength region of visible light.

5. A variable focal-length lens which includes the variable optical-property element stated in item 1 is used.

6. In item 1, the variable optical-property element satisfies at least one of Conditions (28)-(30), (35)-(37), and (39).

7. A variable optical-property element includes a molecular dispersed liquid crystal in which the average diameter of the particles of the liquid crystal is less than 500 times the wavelength of light used and more than 7 nm, to which a spatially uneven electric or magnetic field or temperature is applied to thereby form an index distribution, so that the electric or magnetic field or the temperature is changed to alter the index distribution.

8. A variable optical-property element includes a molecular dispersed liquid crystal in which the average diameter of the particles of the liquid crystal is smaller than the wavelength of light used and larger than the molecule of the liquid crystal, to which a spatially uneven electric or magnetic field or temperature is applied to thereby form an index distribution, so that the electric or magnetic field or the temperature is changed to alter the index distribution.

9. In item 2, the variable optical-property element satisfies at least one of Conditions (53), (54), (57), and (59)-(61).

10. A variable optical-property element includes a liquid crystal to which an electric field is applied through at least two electrodes having different shapes.

11. In item 1 or 2, the variable optical-property element includes a liquid crystal to which an electric field is applied through at least two electrodes having different shapes.

12. A variable optical-property element includes a macromolecular dispersed liquid crystal having a single substrate.

13. A variable optical-property element includes a macromolecular dispersed liquid crystal using a ferroelectric liquid crystal or an antiferroelectric liquid crystal is used.

14. A variable optical-property element includes a liquid crystal in which a medium with an Abbe's number of 50 or less is used for the substrate thereof.

15. In item 3, the variable optical-property element is such that the Abbe's number of the liquid crystal of a positive liquid crystal lens is larger than that of a negative liquid crystal lens in the predetermined range of refractive indices of the liquid crystals.

16. In item 3, the variable optical-property element satisfies Condition (63).

17. In item 16, the variable optical-property element uses a tran-base liquid crystal as the liquid crystal of the liquid crystal lens.

18. In any one of items 3 and 15-17, the variable optical-property element uses a liquid crystal with an Abbe's number of 50 or less.

19. A variable optical-property element uses a tran-base liquid crystal.

20. In any one of items 1-15, the variable optical-property element uses a substance having an electrooptical, magnetrooptical, or thermooptical effect, instead of the liquid crystal.

21. An imaging device has an irrotational symmetric surface, a surface with no symmetric axis in either an inner or outer surface, a surface with no rotational symmetric axis with respect to an optical function surface, or a surface with a single symmetric surface in either an inner or outer surface and a variable optical-property element.

22. In any one of items 1-20, an optical apparatus includes the variable optical-property element.

23. A variable focal-length imaging device or an optical apparatus is provided with a free-formed surface and the variable optical-property element stated in any one of items 1-20.

24. A variable focal-length imaging device or an optical apparatus is provided with an inhomogeneous lens, a diffraction optical element, or an aspherical lens and the variable optical-property element stated in any one of items 1-20.

25. An autofocus device uses the variable optical-property element stated in any one of items 1-20.

26. A diopter adjusting device uses the variable optical-property element stated in any one of items 1-20.

27. Variable focal-length spectacles use the variable optical-property element stated in any one of items 1-20.

28. A variable optical-property element uses a liquid crystal in which the anisotropy of refractive index is negative, to which an electric or magnetic field or temperature is applied to thereby change the refractive index and optical properties.

29. A variable optical-property element uses a substance possessing an electrooptical effect such that the orientation of molecules is almost uniform in a plane nearly perpendicular to the optical axis of incidence.

30. A variable optical-property element has a liquid crystal provided with a liquid crystal element and members for applying an electric field in a direction nearly perpendicular to the optical axis of the liquid crystal element.

31. A variable optical-property element uses a substance possessing an electrooptical or magnetooptical effect in which the anisotropy of refractive index is negative, to which an electric or magnetic field is applied to thereby change the refractive index and optical properties of the substance.

32. A variable optical-property element has a liquid crystal in which the orientation of liquid crystal molecules in a plane nearly perpendicular to the optical axis of incidence is almost uniform, to which an electric or magnetic field or temperature is applied to thereby change the refractive index and optical properties of the liquid crystal.

33. A variable focal-length lens uses the variable optical-property element stated in item 28 or 31.

34. A variable optical-property element uses a substance possessing an electrooptical effect in which the orientation of the substance in a plane nearly perpendicular to the optical axis of incidence is almost uniform, so that the refractive index of the substance is changed and thereby optical properties are varied.

35. In item 28, 29, or 32, the variable optical-property element is provided with a member for controlling the orientation of liquid crystal molecules, the member being fabricated by photoresist exposure and etching or lithographic technology.

36. A variable optical-property element is provided with a member for controlling the orientation of a substance possessing an electrooptical or magnetooptical effect, the member being fabricated by photoresist exposure and etching or lithographic technology.

37. In item 35 or 36, the variable optical-property element is such that the member satisfies Condition (67).

38. In item 30, the variable optical-property element has the liquid crystal in which the anisotropy of refractive index is negative.

39. A variable optical-property element is provided with a liquid crystal element and members for applying an electric field in a direction nearly perpendicular to the optical axis of the liquid crystal element, the electric field being applied so that its direction changes with time.

40. A variable optical-property element is provided with a liquid crystal element, members for applying one electric field in a direction nearly parallel to the optical axis of the liquid crystal element, and members for applying another electric field in a direction nearly perpendicular to the optical axis.

41. In any one of items 30 and 37-40, the variable optical-property element satisfies Condition (78).

42. In item 41, the variable optical-property element, instead of satisfying Condition (78), satisfies Condition (79).

43. In any one of items 3 and 37-42, the variable optical-property element has the liquid crystal whose molecules are oriented in helical fashion.

44. In item 43, the variable optical-property element satisfies at least one of Conditions (28)-(30) and (69)-(71).

45. In any one of items 30 and 37-42, the variable optical-property element uses a macromolecular dispersed liquid crystal element as the liquid crystal element.

46. A variable optical-property element uses a macromolecular dispersed liquid crystal, satisfying at least one of Conditions (80)-(83).

47. In item 45, the variable optical-property element satisfies at least one of Conditions (81) and (83).

48. A variable optical-property element has a liquid crystal that the transfer from a liquid crystal phase to a liquid phase is produced by temperature change to vary its refractive index.

49. In any one of items 28-47, the variable optical-property element includes a liquid crystal that a variable strength magnetic field is applied to control the orientation of the molecules of the liquid crystal.

50. In any one of items 28-47, the variable optical-property element includes a liquid crystal that the strength or frequency of an electric field is changed to thereby control the orientation of the molecules of the liquid crystal.

51. In any one of items 28-47, the variable optical-property element uses a liquid crystal element that a dielectric anisotropy changes with the frequency of an electric field.

52. In any one of items 28-51, the variable optical-property element, instead of using a liquid crystal, uses one of a substance possessing an electrooptical effect, a substance possessing a magnetooptical effect, and a ferroelectric.

53. An imaging device is provided with the variable optical-property element stated in any one of items 28-52.

54. Variable focal-length spectacles are provided with the variable optical-property element stated in any one of items 28-52.

55. An optical apparatus is provided with variable optical-property element stated in any one of items 28-52.

56. An imaging device is provided with an optical system comprising a stop, a front lens unit including a variable optical-property element possessing the function of a negative lens, placed close to the stop, and a rear lens unit including at least one concave surface and one convex surface, placed behind the front lens unit.

57. An imaging device is provided with an optical system comprising a stop, a front lens unit including a variable optical-property element placed close to the stop, and a rear lens unit including at least one concave surface and one convex surface, placed behind the front lens unit.

58. In item 56 or 57, the imaging device has at least one aspherical surface.

59. In item 56, 57, or 58, the imaging device has an image sensor whose imaging surface is located at the image plane of the optical system so that an angle of a chief ray of light incident on the imaging surface is within a range of 90±200 with respect to the imaging surface.

60. A variable optical-property element is such that the frequency of an electric field applied to a liquid crystal is changed to thereby vary its optical properties.

61. In item 23, the variable optical-property element is provided with the liquid crystal having a helical structure, satisfying any one of Conditions (26), (28)-(30), and (69)-(77).

62. In item 60 or 61, the variable optical-property element uses the liquid crystal having a positive anisotropy of refractive index.

63. An imaging device is provided with the variable optical-property element stated in item 60, 61, or 62.

64. Variable focal-length spectacles are provided with the variable optical-property element stated in item 60, 61, or 62.

65. An optical apparatus is provided with the variable optical-property element stated in item 60, 61, or 62.

66. A variable optical-property element includes a liquid crystal having a helical structure so that the orientation of the molecules of the liquid crystal is changed to thereby vary its optical properties.

67. In item 66, the variable optical-property element satisfies any one of Conditions (26), (28)-(30), and (69)-(77).

68. An imaging device is provided with the variable optical-property element stated in item 67.

69. An observing device is provided with the variable optical-property element stated in item 67.

70. A display device is provided with the variable optical-property element stated in item 67.

71. Spectacles are provided with the variable optical-property element stated in item 67.

72. In item 68, the imaging device is provided with an optical system comprising a stop, a front lens unit including the variable optical-property element possessing the function of a negative lens, placed close to the stop, and a rear lens unit including at least one concave surface and one convex surface, placed behind the front lens unit.

73. In item 68, the imaging device is provided with an optical system comprising a stop, a front lens unit including the variable optical-property element placed close to the stop, and a rear lens unit including at least one concave surface and one convex surface, placed behind the front lens unit.

74. In item 72 or 73, the imaging device has at least one aspherical surface.

75. In item 72, 73, or 74, the imaging device has an image sensor whose imaging surface is located at the image plane of the optical system so that an angle of a chief ray of light incident on the imaging surface is within a range of 90±200 with respect to the imaging surface.

76. An imaging device has a variable optical-property element to change the MTF characteristics of an electronic circuit or an image processing technique in accordance with changes of properties of the variable optical-property element.

77. An imaging device has a variable optical-property element to change the MTF characteristics of an electronic circuit or an image processing technique in accordance with changes of properties of the variable optical-property element caused by a focus adjustment.

78. An imaging device has a variable optical-property element to change the MTF characteristics of an electronic circuit or an image processing technique in accordance with changes of properties of the variable optical-property element caused by a zooming operation.

79. An imaging device has the variable optical-property element stated in any one of items 31-52, to change the MTF characteristics of an electronic circuit or an image processing technique in accordance with changes of properties of the variable optical-property element.

80. An imaging device has the variable optical-property element stated in any one of items 31-52, to change the MTF characteristics of an electronic circuit or an image processing technique in accordance with changes of properties of the variable optical-property element caused by a focus adjustment.

81. An imaging device has the variable optical-property element stated in any one of items 31-52, to change the MTF characteristics of an electronic circuit or an image processing technique in accordance with changes of properties of the variable optical-property element caused by a zooming operation.

82. An optical system is provided with an irrotational symmetric surface and a variable optical-property reflecting mirror.

83. An imaging device includes an optical element having irrotational symmetric surfaces, a variable optical-property reflecting mirror, and an image sensor, so that the reflecting mirror and the image sensor are placed on the same substrate, and the reflecting mirror and the optical system having the irrotational symmetric surfaces constitute the whole or a part of an optical system.

84. An imaging device includes an optical element having irrotational symmetric surfaces and a variable optical-property reflecting mirror, so that the reflecting mirror is placed close to one surface of the optical element.

85. In item 82, the optical system uses a membrane mirror as the variable optical-property reflecting mirror.

86. In item 83 or 84, the imaging device uses a membrane mirror as the variable optical-property reflecting mirror.

87. In item 83, 84, or 86, the imaging device is such that the variable optical-property reflecting mirror and the optical element are made by the use of a lithography process.

88. In item 84, the imaging device has the variable optical-property reflecting mirror placed on at least one surface of the optical element having the irrotational symmetric surfaces and an image sensor placed on another surface.

89. In item 83, the imaging device has the variable optical-property reflecting mirror including a liquid crystal in which the anisotropy of refractive index is negative, so that an electric or magnetic field or temperature is applied to the liquid crystal, and thereby the refractive index is changed to vary its optical properties.

90. In item 83, the imaging device has the variable optical-property reflecting mirror including a liquid crystal in which the orientation of the molecules of the liquid crystal is almost uniform in a plane perpendicular to the optical axis of incidence.

91. In item 83, the imaging device has the variable optical-property reflecting mirror including a substance possessing an electrooptical effect such that the orientation of molecules is almost uniform in a plane nearly perpendicular to the optical axis of incidence.

92. In item 83, the imaging device has the variable optical-property reflecting mirror including a liquid crystal element so that an electric field is applied in a direction nearly perpendicular to the optical axis of the liquid crystal element to thereby change its optical properties.

93. In item 83, the imaging device has the variable optical-property reflecting mirror including a substance possessing an electrooptical or magnetrooptical effect in which the anisotropy of refractive index is negative, to which an electric or magnetic field is applied to thereby change the refractive index and optical properties of the substance.

94. In item 83, the imaging device has the variable optical-property reflecting mirror including a liquid crystal in which the orientation of the molecules of the liquid crystal is almost uniform in a plane nearly perpendicular to the optical axis of incidence, so that an electric or magnetic field or temperature is applied to the liquid crystal, and thereby the refractive index is changed to vary its optical properties.

95. In item 83, the imaging device has the variable optical-property reflecting mirror including a liquid crystal element and is provided with members for applying an electric field in a direction nearly perpendicular to the optical axis of the liquid crystal element, the electric field being applied so that its direction changes with time.

96. In item 83, the imaging device has the variable optical-property reflecting mirror including a liquid crystal element and is provided with members for applying one electric field in a direction as nearly parallel to the optical axis of the liquid crystal element, and members for applying another electric field in a direction nearly perpendicular to the optical axis.

97. In item 83, the imaging device has the variable optical-property reflecting mirror including the optical element stated in item 92, 95, or 96, satisfying Condition (78).

98. In item 97, the imaging device, instead of Condition (78), satisfies Condition (79).

99. In item 83, the imaging device has the variable optical-property reflecting mirror including a liquid crystal element, the molecules of a liquid crystal used in the liquid crystal element being oriented in helical fashion.

100. In item 99, the imaging device satisfies at least one of Conditions (28)-(30) and (69)-(71).

101. In item 83, the imaging device has the variable optical-property reflecting mirror including a liquid crystal element which uses a macromolecular dispersed liquid crystal.

102. In item 101, the imaging device satisfies at least one of Conditions (80) and (82).

103. In item 101, the imaging device satisfies at least one of Conditions (81) and (83).

104. In item 83, the imaging device has the variable optical-property reflecting mirror in which the temperature of the liquid crystal element is changed and thereby its optical properties are varied.

105. In item 102 or 103, the imaging device includes a liquid crystal that a variable strength magnetic field is applied to control the orientation of the molecules of the liquid crystal.

106. In item 83, the imaging device has the variable optical-property reflecting mirror including a liquid crystal that the strength or frequency of an electric field is changed to thereby control the orientation of the molecules of the liquid crystal.

107. In item 83, the imaging device has the variable optical-property reflecting mirror including a liquid crystal element that a dielectric anisotropy changes with the frequency of an electric field.

108. In item 82, the imaging device includes the optical system in which the irrotational symmetric surface is formed with only one symmetric surface.

109. An imaging device includes an optical element having irrotational symmetric surfaces, a reflecting mirror, and an image sensor, the reflecting mirror and the image sensor being placed on the same substrate.

110. An optical system includes an optical element having irrotational symmetric surfaces, a reflecting mirror, and an image sensor, the reflecting mirror and the image sensor being placed on the same substrate.

111. In item 82, the optical system has the variable optical-property reflecting mirror including a liquid crystal in which the anisotropy of refractive index is negative, to which an electric or magnetic field or temperature is applied so that the refractive index is changed to vary its optical properties.

112. In item 82, the optical system has the variable optical-property reflecting mirror including a liquid crystal in which the orientation of the molecules of the liquid crystal is almost uniform in a plane perpendicular to the optical axis of incidence.

113. In item 82, the optical system has the variable optical-property reflecting mirror including a substance possessing an electrooptical effect such that the orientation of molecules is almost uniform in a plane nearly perpendicular to the optical axis of incidence.

114. In item 82, the optical system has the variable optical-property reflecting mirror including a liquid crystal element so that an electric field is applied in a direction nearly perpendicular to the optical axis of the liquid crystal element to thereby change its optical properties.

115. In item 82, the optical system has the variable optical-property reflecting mirror including a substance possessing an electrooptical or magnetrooptical effect in which the anisotropy of refractive index is negative, to which an electric or magnetic field is applied to thereby change the refractive index and optical properties of the substance.

116. In item 82, the optical system has the variable optical-property reflecting mirror including a liquid crystal in which the orientation of the molecules of the liquid crystal is almost uniform in a plane nearly perpendicular to the optical axis of incidence, so that an electric or magnetic field or temperature is applied to the liquid crystal, and thereby the refractive index is changed to vary its optical properties.

117. In item 82, the optical system has the variable optical-property reflecting mirror including a liquid crystal element and is provided with members for applying an electric field in a direction nearly perpendicular to the optical axis of the liquid crystal element, the electric field being applied so that its direction changes with time.

118. In item 82, the optical system has the variable optical-property reflecting mirror including a liquid crystal element and is provided with members for applying one electric field in a direction nearly parallel to the optical axis of the liquid crystal element, and members for applying another electric field in a direction nearly perpendicular to the optical axis.

119. In item 114, 117, or 118, the optical system satisfies Condition (78).

120. In item 119, the optical system, instead of satisfying Condition (78), satisfies Condition (79).

121. In item 82, the optical system has the variable optical-property reflecting mirror including a liquid crystal element, the molecules of a liquid crystal used in the liquid crystal element being oriented in helical fashion.

122. In item 121, the optical system satisfies at least one of Conditions (28)-(30) and (69)-(71).

123. In item 82, the optical system has the variable optical-property reflecting mirror including a liquid crystal element which uses a macromolecular dispersed liquid crystal.

124. In item 123, the optical system satisfies at least one of Conditions (80) and (82).

125. In item 124, the optical system satisfies at least one of Conditions (81) and (83).

126. In item 82, the optical system has the variable optical-property reflecting mirror in which the temperature of the liquid crystal element is changed and thereby its optical properties are varied.

127. In item 124 or 125, the optical system includes a liquid crystal that a variable strength magnetic field is applied to control the orientation of the molecules of the liquid crystal.

128. In item 82, the optical system has the variable optical-property reflecting mirror including a liquid crystal that the strength or frequency of an electric field is changed to thereby control the orientation of the molecules of the liquid crystal.

129. In item 82, the optical system has the variable optical-property reflecting mirror including a liquid crystal element that a dielectric anisotropy changes with the frequency of an electric field.

130. An optical apparatus is provided with optical elements having irrotational symmetric surfaces, variable optical-property reflecting mirrors, and displays.

131. An observing device is provided with an optical element having irrotational symmetric surfaces and a variable optical-property reflecting mirror.

132. An optical system is provided with irrotational symmetric surfaces and a variable optical-property element.

133. An imaging optical system is provided with irrotational symmetric surfaces and a variable optical-property element.

134. An optical apparatus is provided with irrotational symmetric surfaces and a variable optical-property element.

135. An observing device is provided with irrotational symmetric surfaces and a variable optical-property element.

What is claimed is:

1. An optical apparatus comprising an optical system that forms a two-dimensional image,
the optical system comprising:
a variable optical-property mirror, and
a driving circuit that drives the variable optical-property mirror,
wherein the variable optical-property mirror is arranged to be decentered from a light-incident-side optical axis,
wherein the variable optical-property mirror has a reflecting surface that is deformable, and
wherein the reflecting surface is a free-formed surface having only one plane of symmetry.

2. An optical apparatus according to claim 1, further comprising an image sensor.

3. An optical apparatus according to claim 1,
wherein the optical system forms an image surface on an exit side thereof, and
wherein the optical system further comprises an optical element arranged between the image surface and the reflecting surface of the variable optical-property mirror.

4. An optical apparatus according to claim 1, wherein the optical system further comprises an optical element having a rotationally asymmetric optical surface.

5. An optical apparatus according to claim 1,
wherein the optical system further comprises a rotationally asymmetric reflecting surface, and
wherein the rotationally asymmetric reflecting surface is arranged to be tilted in reference to an optical axis of the optical system.

6. An optical apparatus according to claim 5, wherein the rotationally asymmetric reflecting surface defines only one plane of symmetry or no plane of symmetry.

7. An optical apparatus according to claim 1, wherein the optical system further comprises an optical element that has a plurality of rotationally asymmetric optical surfaces.

8. An optical system comprising:
a variable optical-property element; and
a plurality of rotationally asymmetric curved surfaces,
wherein the variable optical-property element and the plurality of rotationally asymmetric curved surfaces are arranged along a single traveling path of rays at positions different from one another,
wherein the variable optical-property element is arranged to be decentered from an optical axis of the optical system, and
wherein the variable optical-property element is arranged between the plurality of rotationally asymmetric curved surfaces.

9. An optical system according to claim 8, wherein the plurality of rotationally asymmetric curved surfaces are provided on a single optical element.

10. An optical system according to claim 9, further comprising an image sensor.

11. An optical system according to 10, wherein each of the variable optical-property element and the image sensor is disposed on a surface of the optical element provided with the plurality of rotationally asymmetric curved surfaces.

12. An optical system according to claim 8, wherein the rotationally asymmetric curved surfaces of the optical element are reflecting surfaces and are arranged to be decentered from the optical axis of the optical system.

13. An optical system comprising:
a variable optical-property mirror;
a driving circuit that drives the variable optical-property mirror; and
an optical element having a light-deflecting function and disposed before or after the variable optical-property mirror in a single traveling path of rays, wherein a shape of a reflecting surface of the variable optical-property mirror is deformable, wherein the variable optical-property mirror is arranged to be decentered from a light-incident-side optical axis, and wherein the optical element has a rotationally asymmetric surface having a shape that defines only one plane of symmetry or no plane of symmetry.

14. An optical device comprising:

a variable optical-property element having a light-deflecting function;

a driving circuit that drives the variable optical-property element; and a free-formed-surface optical element having a rotationally asymmetric reflecting surface and a free-formed transmission surface having only one plane of symmetry, wherein the rotationally asymmetric reflecting surface defines only one plane of symmetry or no plane of symmetry, wherein the variable optical-property element and the rotationally asymmetric reflecting surface are arranged to be decentered from one another, and wherein a positional relation between an image surface, the free-formed-surface optical element, and the variable optical-property element remains unchanged during focusing.

15. An optical device according to claim 14, wherein the variable optical-property element is a reflection-type element.

16. An optical system comprising:

a plurality of variable optical-property elements each having a variable optical power; and an optical element having a rotationally asymmetric optical surface, wherein the plurality of variable optical-property elements and the optical element are arranged along a single traveling path of rays, wherein the variable optical-property elements and the optical element are decentered from one another, wherein the rotationally asymmetric optical surface is a smooth surface directed toward a light-incident side, and wherein the variable optical-property elements are arranged to be decentered from one another.

17. An optical unit comprising:

a transparent optical element having an entrance surface and an exit surface that is different from the entrance surface; and a reflection-type variable optical-property element having a variable optical power, the reflection-type variable optical-property element being arranged integrally with the transparent optical element, wherein the transparent optical element and the reflection-type variable optical-property element are configured such that light enters the optical element through the entrance surface, is reflected at the reflection-type variable optical-property element, and then exits out of the transparent optical element through the exit surface, and wherein at least one of the entrance surface and the exit surface of the transparent optical element is a curved surface.

\* \* \* \* \*